US011801364B2

(12) United States Patent
Maguire et al.

(10) Patent No.: US 11,801,364 B2
(45) Date of Patent: Oct. 31, 2023

(54) ELECTROSPRAY CATHETER

(71) Applicant: Avectas Limited, Kildare (IE)

(72) Inventors: Michael Maguire, Dublin (IE); Shane Finnegan, Dublin (IE)

(73) Assignee: Avectas Limited, County Kildare (IE)

(*) Notice: Subject to any disclaimer, the term of this patent is extended or adjusted under 35 U.S.C. 154(b) by 34 days.

(21) Appl. No.: 16/624,986

(22) PCT Filed: Jun. 29, 2018

(86) PCT No.: PCT/IB2018/000831

§ 371 (c)(1),
(2) Date: Dec. 20, 2019

(87) PCT Pub. No.: WO2019/002942

PCT Pub. Date: Jan. 3, 2019

(65) Prior Publication Data

US 2020/0215307 A1 Jul. 9, 2020

Related U.S. Application Data

(60) Provisional application No. 62/527,989, filed on Jun. 30, 2017.

(51) Int. Cl.
*A61M 25/01* (2006.01)
*A61M 25/00* (2006.01)
(Continued)

(52) U.S. Cl.
CPC .... *A61M 25/0122* (2013.01); *A61M 25/0043* (2013.01); *A61M 25/0068* (2013.01);
(Continued)

(58) Field of Classification Search
CPC .............. A61M 25/00; A61M 25/0043; A61M 25/0045; A61M 25/0067; A61M 25/0068;
(Continued)

(56) References Cited

U.S. PATENT DOCUMENTS 5,759,191 A * 6/1998 Barbere .............. A61M 25/104 604/103.1
6,689,103 B1 * 2/2004 Palasis .............. A61M 25/0084 606/186

(Continued)

FOREIGN PATENT DOCUMENTS

WO 9856894 A1 12/1998
WO 2009130187 A1 10/2009

OTHER PUBLICATIONS

Rigel Medical. "A Practical Guide to IEC 60601-1." Published Jun. 2007. (Year: 2007).*

(Continued)

*Primary Examiner* — Kami A Bosworth
(74) *Attorney, Agent, or Firm* — Mintz Levin Cohn Ferris Glovsky and Popeo, P.C.

(57) ABSTRACT

An apparatus includes a catheter, and an electrode and methods of delivering molecules to eukaryotic cells using such an apparatus. The catheter defines a fluidic channel and has a distal opening. The electrode is within the fluidic channel and is spaced a distance from the distal opening of the catheter. The catheter is arranged to prevent direct contact between any electrode of the apparatus and tissue. Related apparatus, systems, techniques and articles are also described.

8 Claims, 40 Drawing Sheets

(51) Int. Cl.

| | |
|---|---|
| ***B05B 5/00*** | (2006.01) |
| ***B05B 5/16*** | (2006.01) |
| *A61M 25/06* | (2006.01) |
| *A61M 25/09* | (2006.01) |

(52) U.S. Cl.
CPC ......... *A61M 25/0074* (2013.01); *B05B 5/007* (2013.01); *B05B 5/165* (2013.01); *A61M 2025/0057* (2013.01); *A61M 2025/0166* (2013.01); *A61M 2025/0681* (2013.01); *A61M 2025/09133* (2013.01); *A61M 2205/0233* (2013.01); *A61M 2205/3334* (2013.01); *A61M 2210/1039* (2013.01)

(58) Field of Classification Search
CPC ...... A61M 25/0074; A61M 2025/0004; A61M 2025/0006; A61M 2025/0057; A61M 2025/0073; A61M 2025/0293; A61M 2025/0681; A61M 2025/1047; A61M 2205/0233; A61M 2205/0238; A61M 2205/75; A61M 2206/00; A61M 2206/10; A61M 2206/14; A61M 2206/20; A61M 2210/1039; A61M 15/02; A61M 11/001; A61M 11/003; A61M 11/004; A61M 2205/7527; A61M 2205/7536; A61M 25/007; A61M 25/0082; A61M 2025/0085; A61M 37/00; A61M 2037/0053; A61M 11/00; A61M 11/042; A61M 11/044; B05B 5/005; B05B 5/007; B05B 5/057; B05B 5/1608; B05B 5/1616; B05B 5/165; B05B 5/1658; B05B 1/02; B05B 1/06; B05B 1/04; B05B 1/042; B05B 1/044; B05B 1/046; B05B 1/048; B05B 5/00–06; B05B 5/16–1691
See application file for complete search history.

(56) References Cited

U.S. PATENT DOCUMENTS

| | | | | | |
|---|---|---|---|---|---|
| 8,260,411 | B1 * | 9/2012 | Odland | A61N 1/306 | 604/21 |
| 2007/0048452 | A1 * | 3/2007 | Feng | B05B 5/0533 | 427/458 |
| 2007/0073249 | A1 * | 3/2007 | Zambaux | A61M 5/329 | 604/272 |
| 2009/0088700 | A1 * | 4/2009 | Imbayashi | A61M 11/007 | 604/181 |
| 2010/0155496 | A1 * | 6/2010 | Stark | H05K 3/1241 | 239/3 |
| 2014/0039456 | A1 * | 2/2014 | Lerner | A61F 9/007 | 604/506 |
| 2015/0251201 | A1 * | 9/2015 | Hradetzky | B05B 5/1691 | 239/690 |
| 2015/0352297 | A1 * | 12/2015 | Stedman | A61M 15/0033 | 128/200.14 |

OTHER PUBLICATIONS

PCT Search Report and Written Opinion issued in connection with corresponding PCT Application No. PCT/WO/2019/002942 dated Mar. 1, 2019.

* cited by examiner

220

(A)

(B)

0.031%w/v @ 2.5μl/min

| Methodology | Toxicity | In Vivo | In Vitro | Targeted Delivery | Safety | Efficacy |
|---|---|---|---|---|---|---|
| Lipids | High | Yes | Yes | No | Poor | High |
| Viruses | Immunogenic in vivo | Yes | Yes | No | Poor | High |
| Aerosols | Low | Yes | No | No | Good | Low |
| Gene Gun (Bio Rad) | Potentially (gold particulate) | No | Yes | Poor | Poor, pitting damage to cells | Low |
| Electroporation | Non-specific take up | Recently | Yes | Yes | Unknown | High |
| Nanoparticle generator | Low | No | Yes | Yes | Good | High |
| Endoscopic spray catheter | Low | Yes | Yes | Yes | Good | Low |
| Electrospray | Low | Yes | Yes | Yes | Good | Low |

*FIG. 6*

A
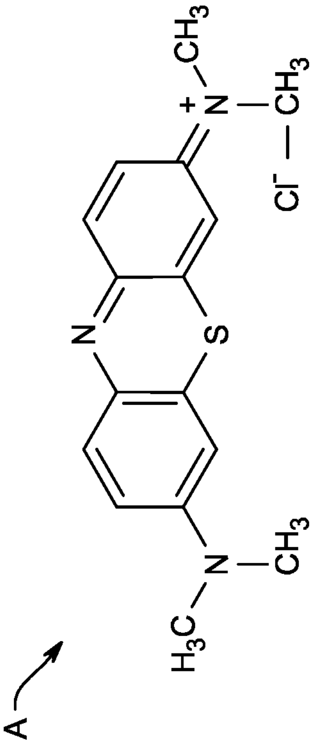
B
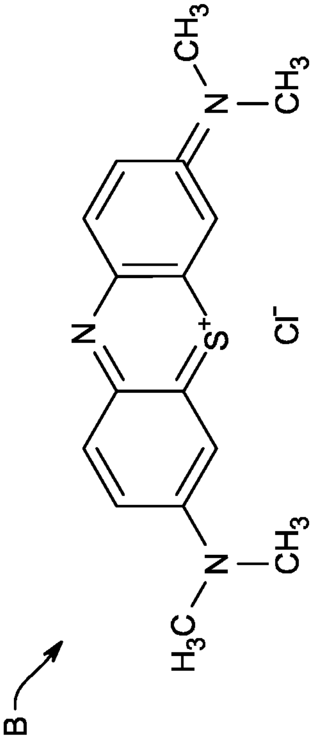
FIG. 11

DNA delivery explant (A)

| Voltage | Flow Rate | Needle gauge | Spray Mode |
|---|---|---|---|
| 3 kV | 60 | 22 | Drip |
| | | 32 | Fast drip |
| | 30 | 22 | Drip |
| | | 23 | Drip |
| 4 kV | 60 | 22 | Drip |
| | | 32 | Spray |
| | 30 | 22 | Drip |
| | | 32 | Spray |
| 5 kV | 60 | 22 | Drip/Spray |
| | | 32 | Spray |
| | 30 | 22 | Drip/Spray |
| | | 32 | Spray |
| 6 kV | 60 | 22 | Spray |
| | | 32 | Spray |
| | 30 | 22 | Spray |
| | | 32 | Spray |

FIG. 27

- Tip-to-plate distance = 26 mm
- 77% ethanol

Tip-to-plate distance = 26 mm

Tip-to-plate distance = 6 mm

No spray

100% ethanol 0.25% methylene blue + 1% ethanol (b)

(a)

ELECTROSPRAY CATHETER

CROSS-REFERENCES TO RELATED APPLICATIONS

This application is a national stage application filed under 35 U.S.C. § 371, of International Patent Application No. PCT/IB2018/000831 filed Jun. 29, 2018 which claims the benefit of and priority under 35 U.S.C. § 119(e) to U.S. Provisional Application No. 62/527,989 filed on Jun. 30, 2017, the entire contents of each of which are hereby expressly incorporated herein by reference in its entirety.

TECHNICAL FIELD

The subject matter described herein relates to an electrospray catheter and targeted delivery of fluids using the electrospray catheter.

BACKGROUND

Lung cancer is accountable for the highest number of cancer deaths worldwide, with poor survival rates despite advances in chemotherapy over recent years. The most effective method to substantially improve survival figures would be diagnosing lung cancer at an earlier stage, when therapy may be more effective.

Lung cancer has still a very poor prognosis compared to other types of cancer. Three studies have been reported to date with mixed findings regarding the efficacy of methylene blue staining for identification of malignant and premalignant lesions in a prospective manner. In these studies, relatively large volumes of methylene blue were delivered into the airways using conventional spray catheters. The first study by Ovchinnikov (Ovvhinnikov A A, Dianov V V, Lukomosky G I. Chromobronchoscopy in the Diagnosis of Bronchial Tumours. Endoscopy. 1980; 12:147-150) delivered 2 ml of 0.2-0.4% methylene blue using a bronchoscopic atomizer and reported successful differential staining of metaplasia/tumors versus normal tissue. The second study by Varoli (Varoli F, Mariani C, Fasceanella A, Cosentino F, Vital Staining in Fibreoptic Bronchoscopy. Endoscopy. 1986; 18:142-143) delivered 0.7% methylene blue (the volume was not reported) using a spray catheter and reported that normal bronchial mucosa did not stain while malignant neoplastic tissue stained darkly and areas of squamous metaplasia stained lightly. The third more recent study by Zirlik (Zirlik S, Hildner K M, Neurath M F, Fuchs F S. Methylene blue-aided in vivo staining of central airways during flexible bronchoscopy. Scientific World Journal. 2012; 2012:625867. doi:10.1100/2012/625867) delivered 10 ml of 0.1% methylene blue using a spray catheter. They reported that while methylene blue was an appropriate dye for chromobronchoscopy and that there were sufficient experiences on topical pulmonary application, the technique they used was not helpful for early detection of malignant or premalignant lesions of the bronchial system. It is hypothesized that the large volumes of methylene blue used in these studies, along with the use of spray catheters, which do not allow controlled, targeted delivery, contributed significantly to irreproducibility.

SUMMARY

In an aspect, an apparatus includes a catheter, and an electrode. The catheter defines a fluidic channel and has a distal opening. The electrode is within the fluidic channel and is spaced a distance from the distal opening of the catheter. The catheter is arranged to prevent direct contact between any electrode of the apparatus and tissue.

One or more of the following features can be included in any feasible combination. For example, a conductive sheath can be included on an exterior of the catheter and can be configured to couple to a ground. The catheter can separate the fluidic channel and the conductive sheath. A biocompatible cover enclosing the conductive sheath between the biocompatible cover and the catheter can be included. The biocompatible cover can extend less than an entire length of the catheter, and a distal end of the catheter can be exposed. The catheter can have an inner diameter of about 0.5 mm and an outer diameter of about 1.4 mm. The distance between the electrode and the distal opening can be about 100 mm. The biocompatible cover can have an exterior diameter of about 2.05 mm. The catheter can extend about 50 mm beyond the biocompatible cover at the distal end.

A wire extending through a portion of a length of the catheter and within the fluidic channel can be included. The wire can include an insulation layer and an exposed distal portion. The exposed distal portion can form the electrode. The electrode, when carrying a charge, can impart the charge to fluid traveling through the fluidic channel. The charge can be imparted within the fluidic channel so that, when charged fluid reaches a fluid/air interface near the distal opening of the catheter, the charged fluid forms charged droplets that disperse.

The catheter can include a porous tip disposed within the fluidic channel. The porous tip can include a felt material and/or a fibrous material. The porous tip can include a cone shape geometry. The catheter can include a protrusion disposed near the distal opening of the catheter and surrounding an outer surface of the catheter; and a thermoplastic wrap that encloses the protrusion to provide sealing and electrical isolation.

In another aspect, a system can include a pump, a power supply, a catheter, and an electrode. The catheter is coupled to the pump, defines a fluidic channel, and has a distal opening. The electrode is electrically coupled to the power supply, within the fluidic channel, and spaced a distance from the distal opening of the catheter. The catheter prevents direct contact between any electrode of the system and tissue.

One or more of the following features can be included in any feasible combination. For example, the pump can meter between 1 and 10 microliters of fluid to the fluidic channel per actuation of the pump. The pump can meter between 5 and 500 microliters of fluid to the fluidic channel per actuation of the pump. The power supply charges the electrode to between 3 kilovolts and 10 kilovolts. The power supply can supply charge to the electrode at greater than 160 nanoamps and less than 25 microamps.

A conductive sheath can be included on an exterior of the catheter and can be configured to couple to a ground. The catheter can separate the fluidic channel and the conductive sheath. A biocompatible cover enclosing the conductive sheath between the biocompatible cover and the catheter can be included. The biocompatible cover can extend less than an entire length of the catheter, and a distal end of the catheter can be exposed. The catheter can have an inner diameter of about 0.5 mm and an outer diameter of about 1.4 mm. The distance between the electrode and the distal opening can be about 100 mm. The biocompatible cover can have an exterior diameter of about 2.05 mm. The catheter can extend about 50 mm beyond the biocompatible cover at the distal end.

A wire extending through a portion of a length of the catheter and within the fluidic channel can be included. The wire can include an insulation layer and an exposed distal portion. The exposed distal portion can form the electrode. The electrode, when carrying a charge, can impart the charge to fluid traveling through the fluidic channel. The charge can be imparted within the fluidic channel so that, when charged fluid reaches a fluid/air interface near the distal opening of the catheter, the charged fluid forms charged droplets that disperse.

In yet another aspect, an electrode within a fluidic channel defined by a catheter having a distal opening is charged. The electrode is spaced from the distal opening by a distance. The catheter is arranged to prevent direct contact between any electrode and tissue. A metered volume of fluid is supplied to the fluidic channel to deliver fluid to a target.

One or more of the following features can be included in any feasible combination. The electrode, when carrying a charge, can impart the charge to fluid traveling through the fluidic channel, the charge imparted within the fluidic channel so that, when charged fluid reaches a fluid/air interface near the distal opening of the catheter, the charged fluid forms charged droplets that disperse. The fluid can include Methylene Blue. The catheter can be inserted into an airway of a patient for delivering the fluid to target lung tissue. The catheter can be inserted into one or more of: gastrointestinal tract, oral cavity, central airway, proximal airway, small intestine, and colon. The fluid can be delivered to the target, the target including a portion of one or more of: bowel tissue, parathyroid gland, sentinel node, melanoma, oral tissue, and small intestine tissue. The catheter can be inserted into a bronchealscope.

The fluid can contain Deoxyribonucleic acid (DNA), messenger Ribonucleic acid (mRNA), small interfering Ribonucleic acid (siRNA), and/or protein, which are delivered to the target. The fluid can contain messenger Ribonucleic acid (mRNA).

A conductive sheath can be included on an exterior of the catheter and can be configured to couple to a ground. The catheter can separate the fluidic channel and the conductive sheath. A biocompatible cover enclosing the conductive sheath between the biocompatible cover and the catheter can be included. The biocompatible cover can extend less than an entire length of the catheter, and a distal end of the catheter can be exposed. The catheter can have an inner diameter of about 0.5 mm and an outer diameter of about 1.4 mm. The distance between the electrode and the distal opening can be about 100 mm. The biocompatible cover can have an exterior diameter of about 2.05 mm. The catheter can extend about 50 mm beyond the biocompatible cover at the distal end.

A wire extending through a portion of a length of the catheter and within the fluidic channel can be included. The wire can include an insulation layer and an exposed distal portion. The exposed distal portion can form the electrode. The electrode, when carrying a charge, can impart the charge to fluid traveling through the fluidic channel. The charge can be imparted within the fluidic channel so that, when charged fluid reaches a fluid/air interface near the distal opening of the catheter, the charged fluid forms charged droplets that disperse.

The fluid can contain ethanol at greater than 5% concentration. The fluid can contain ethanol at a concentration between 5 and 75%. The fluid can contain ethanol at about 5, 10, 15, 20, 25, 30, 25, 40, 45, 50, 55, 60, 65, 70, or 75 percent. About can be within 10%, 5%, 4% 3%, 2%, or 1%. For example, the ethanol concentration in the delivery fluid is greater than 5% and less than 80, 75, 70, 65, 60, 55, 50, 45, 40, 35, 30, or 25% ethanol. An exemplary delivery fluid contains ethanol, a physiologically-acceptable buffer solution, and a molecule of interest to be delivered into a viable mammalian cell, e.g., a human cell. The molecule to be delivered comprises a nucleic acid such as a messenger RNA or Small (or short) interfering RNA (siRNA) or a protein.

A distal end of the catheter can be positioned about 15 mm from a surface of tissue.

Delivery of fluid to the target can be performed for between 0.1 second and 10 minutes. The delivery of fluid to the target can be performed for about 0.1 seconds, 0.2 seconds, 1 second, 10 seconds, 1 minute, 2 minutes, 3 minutes, 4 minutes, or 10 minutes. Delivery of fluid to the target can be performed by a single spray. Delivery of fluid to the target can be performed with a flow rate of about 0.1 μl per minute, 3 μl per minute, 4.8 μl per minute 10 μl per minute, 100 μl per minute, or 1 ml per minute.

The charging can be to a voltage between 3 kV and 5 kV. The charging can be to a voltage of about 3 kV, wherein about is within 10%. The distal opening can be 22, 23, 25, 27, 30, or 32 gauge. The distal opening can be 32 gauge. Positive mode electrospray can be utilized.

The current subject matter includes a platform for targeted delivery of diagnostic and therapeutic agents to anatomical locations or organs comprising a lumen, e.g., a lumen through which a catheter is passed. Examples include the pulmonary tissues (including the lung, bronchi and bronchioles), esophagus, urinary bladder (including urethra), stomach, intestines, cardiovascular tissues as well other tissues. In some aspects, the current subject matter includes spray delivery platform technology enabling delivery of diagnostic and therapeutic molecules directly to sites in the body in a targeted and controllable manner. The volume of fluid delivered can be small as compared to some exiting catheters and the fluid can be delivered with a diverse spray.

By way of illustration, in vivo experiments in pigs were performed and are described herein, which supported the efficacy and safety of the current subject matter. Furthermore, experiments using ex vivo lung cancer tissue to show a differential uptake of methylene blue dye in cancer compared to healthy tissue were also performed and are described herein. The ex vivo models described herein represent art-recognized models for in vivo applications and therapy.

In an example implementation, the platform includes an ‘electrospray’ catheter device designed for use in the lungs in vivo, enabling delivery of diagnostic and therapeutic molecules directly to tissues in vivo. The catheter can be deployed using a conventional flexible endoscope. Physicians working in cancer, targeted drug delivery, gene therapy, and diagnostics can use the catheter. The rationale underlying this spray catheter approach is that a targeted, physical mode of delivery can empower clinicians to enhance patient care by (A) enabling novel diagnostic approaches, (B) delivering agents that cannot easily be delivered by existing delivery modes and (C) circumventing problems and limitations associated with aerosol mediated, viral and liposome vector delivery.

The subject matter described herein provides many technical advantages. For example, the current subject matter can deliver small amount of fluid (e.g., between 1 and 10 micro liters), which can cover a microscopically visible area in vivo. Controlled delivery allows for better targeting of tissue for delivery, reduced trauma to tissue, little or no localized pressure on tissue or enclosed area (e.g., vessel or lumen). Improved localized delivery allows for targeting specific tissue such as lesion, with minimal collateral damage while delivering more payload to the target. The current subject matter limits exposure of the patient and target tissue to electrical charge so that only the only charge exposed to the patient and/or tissue is through the fluid, which causes the fluid to disperse when it exits the catheter distal end.

In some implementations, vector-free delivery of molecules can be achieved. The molecules can be delivered not only onto, but into tissues.

The current subject matter can differentially stain lung cancer compared to normal "healthy" tissue in humans. This allows for improved targeting of lung biopsies during bronchoscopy. This improves the sensitivity of biopsies in providing an earlier lung cancer diagnosis and avoiding the need for the patient to progress to further, more invasive, procedures to confirm a diagnosis.

The platform can enhance patient care, offering clinicians an additional strategy for the diagnosis and treatment of lung disease complimenting existing intravenous and nebulized therapy. In particular, the current subject matter can enable clinicians to deliver molecules, such as DNA and siRNA, in the setting of lung disease and to address a broad range of other disease processes outside of the lung.

Molecules to be delivered to eukaryotic cells, e.g., mammalian cells such as human cells are purified. As used herein, an "isolated" or "purified" nucleotide or polypeptide (e.g., a nucleotide or polypeptide) is substantially free of other nucleotides and polypeptides with which the cargo molecule exists in nature. Purified nucleotides and polypeptides are also free of cellular material or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified nucleotides and polypeptides, e.g., a chemoattractant, cytokine, or chemokine is one that is at least 90%, 91%, 92%, 93%, 94%, 95%, 98%, 99%, or 100% (w/w) of the desired oligosaccharide by weight. Purity is measured by any appropriate standard method, for example, by column chromatography, thin layer chromatography, or high-performance liquid chromatography (HPLC) analysis. The nucleotides and polypeptides to be delivered to eukaryotic cells are purified and used in delivery to humans as well as animals, such as companion animals (dogs, cats) as well as livestock (bovine, equine, ovine, caprine, or porcine animals, as well as poultry). "Purified" also defines a degree of sterility that is safe for administration to a human subject, e.g., lacking infectious or toxic agents.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

FIG. 6 is a table comparing properties of vectors for delivering molecules, such as DNA, siRNA, and proteins.

FIG. 11 illustrates proposed structures for methylene blue.

FIG. 27 is a table showing the effects of varying parameters such as voltage, flow rate, needle gauge on the spray mode observed by eye.

FIG. 36 illustrates electrospray formation using an example porous tip with 0.25% methylene blue and 0.01% ammonium acetate, comparing the foot-switch latched off and on.

Like reference symbols in the various drawings indicate like elements.

DETAILED DESCRIPTION

The current subject matter utilizes electrically charged spray or "electrospraying" to deliver fluid, such as dye, to tissue in vivo. The delivery platform can include a catheter with an electrode or charging element positioned within the catheter near a distal opening of the catheter. As precise volumes of fluid meter through the catheter, the electrode imparts charge to the fluid. When charged fluid reaches a fluid/air interface at the distal opening of the catheter, a fine electrospray of fluid is generated. Because the electrode is recessed within the catheter, the electrode is shielded from tissue to prevent electrical hazard to the patient and/or target tissue. Some implementations of the current subject matter can deliver small amount of fluid (e.g., between 1 and 10 micro liters), which can cover a microscopically visible area in vivo. Controlled delivery allows for better targeting of tissue for delivery, reduced trauma to tissue, and little or no localized pressure on tissue or enclosed area (e.g., vessel or lumen).

The term "electrospray" refers to a process where tiny, controlled and safe quantities of electrical charge transfer to a fluid in order to generate a very fine electrospray of the fluid. Unlike an aerosol, which a gas mechanically and externally drives, repulsion forces internally drive electrospray on similarly charged spray colloids. Electrospray is also finer and significantly faster than an aerosol. In some implementations, the device further employs a fluid-charging approach to prevent electrical hazards to the targeted tissue by shielding any and all electrodes of the delivery platform from the target tissue and/or patient. An objective of electrospray delivery of a dye may include differentiating between cancer cells and normal cells in vivo such that the technic may be used to detect early lung cancerous changes within the tracheobronchial tree by staining early neoplastic epithelial changes following electrospray.

Figure 1:
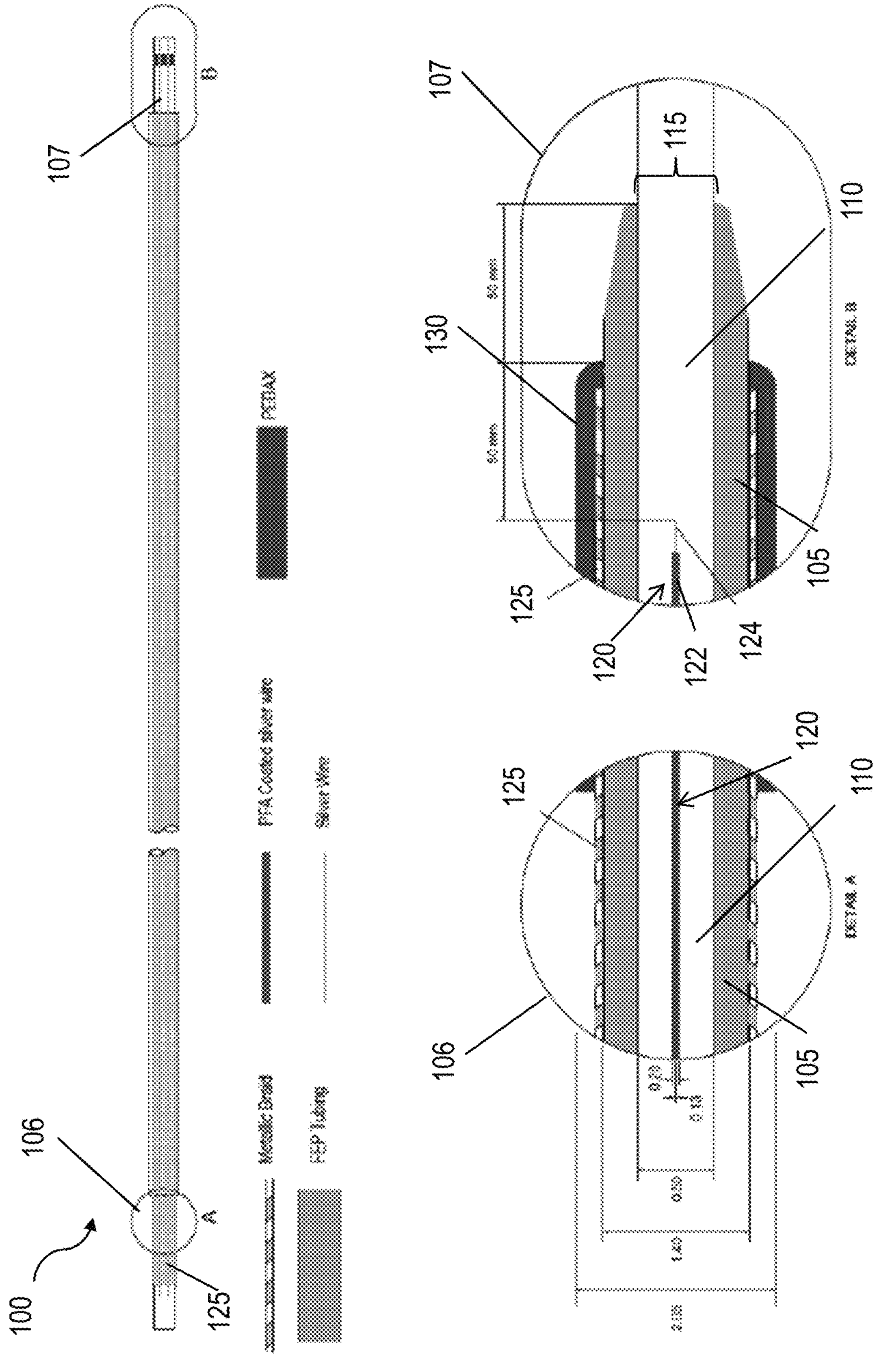
FIG. 1 is a cross-sectional diagram of a delivery platform according to an example implementation.

FIG. 1 is a cross-sectional diagram of a delivery platform 100 according to an example implementation. The dimensions and materials shown in FIG. 1 are exemplary. The delivery platform 100 includes a catheter 105 having a proximal end 106 and distal end 107. The proximal end 106 and distal end 107 are illustrated in an expanded view in FIG. 1. The catheter 105 has an inner diameter defining a fluidic channel 110. At distal end 107 of the catheter 105 is a distal opening 115. A wire 120 extends through the length of the catheter 105 and within the fluidic channel 110. The wire 120 includes an insulation layer 122 and an electrode 124 (e.g., an exposed portion of wire, also referred to as a charging element). The electrode 124 (e.g., exposed portion or charging element) is near the distal opening 115 but spaced a distance from the opening 115 to prevent direct contact between the electrode 124 and target tissue and/or patient thus preventing electrical hazard to the target tissue and/or patient. The insulation layer may be made of nylon.

A conductive sheath 125 surrounds the exterior of catheter 105 and may couple to ground, for example, at the proximal end. The conductive sheath 125 can be grounded and can act as a shield between the electrode 124 and the patient and/or tissue. The conductive sheath 125 can include a metallic braid, as illustrated in FIG. 1.

Surrounding and enclosing at least a portion of the conductive sheath 125 is a biocompatible cover 130. The biocompatible cover 130 can be smooth and lubricious for easy passage through lumens, such as a bronchoscope tool channel. Biocompatible cover 130 may be formed of a biocompatible material such as, for example, polyether block amide (PEBA).

As illustrated in FIG. 1, the biocompatible cover 130 extends less than the entire length of the catheter. In particular, the distal end of the catheter 105 exposes and extends beyond the biocompatible cover 130. It is also contemplated that the conductive sheath 125 can extend down the length of catheter 105 further than the wire 120, but less than the catheter 107 at the distal end of the delivery platform 100. Such a configuration shields the patient from electrical hazard while preventing grounding of charged fluid, which would hinder or prevent formation of a Taylor cone. Thus, the energy used within the delivery platform 100 is substantially or entirely used to comminute a fluid column within the delivery platform 100. There is no significant change in the energy input and output of the delivery platform 100 because energy is not intended to be conducted to the body for the device to function.

Figure 2:
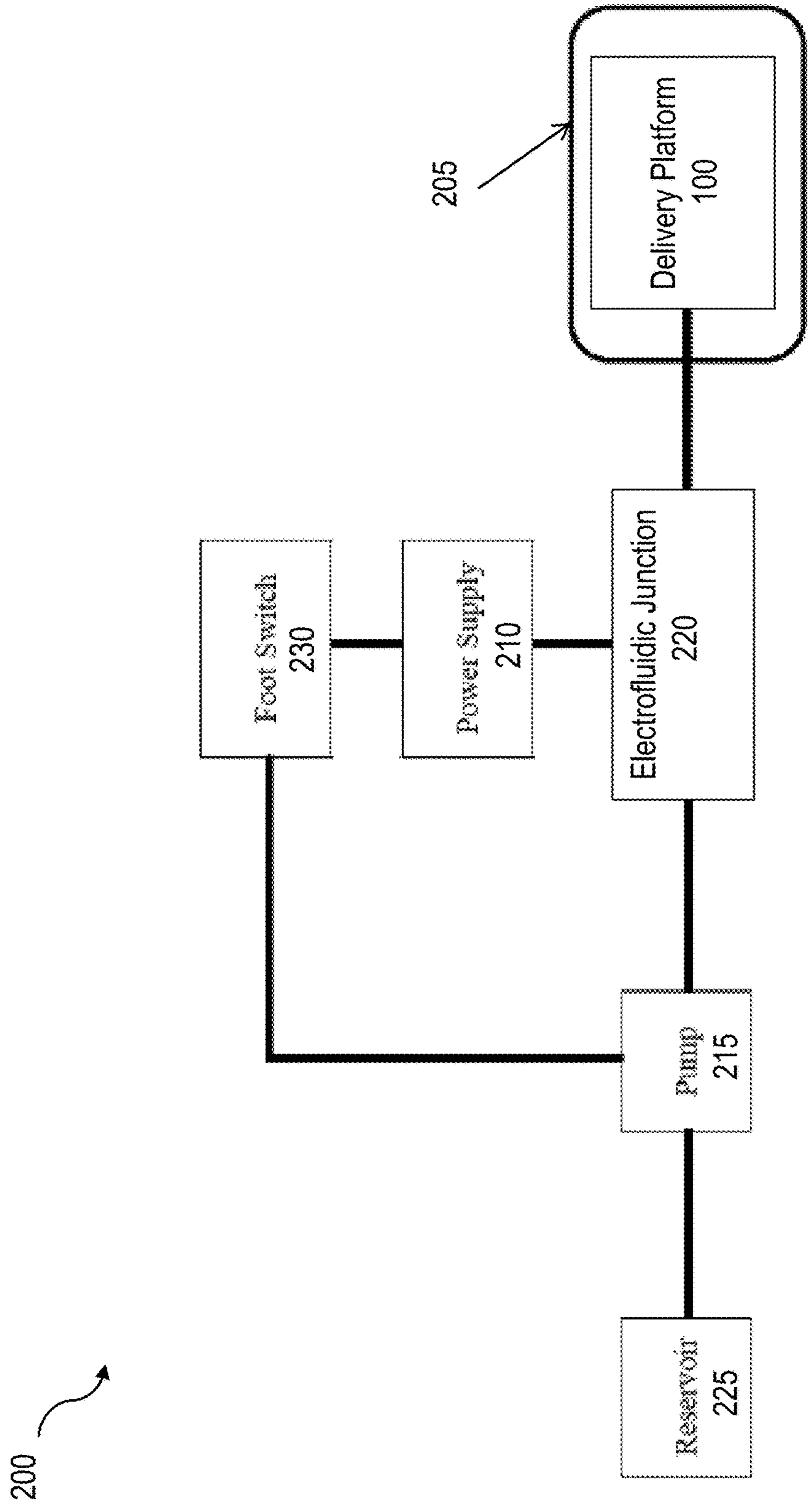
FIG. 2 is a system block diagram illustrating a delivery system including delivery platform for targeting delivery of fluid, such a dye, to tissue in vivo.
Figure 3:
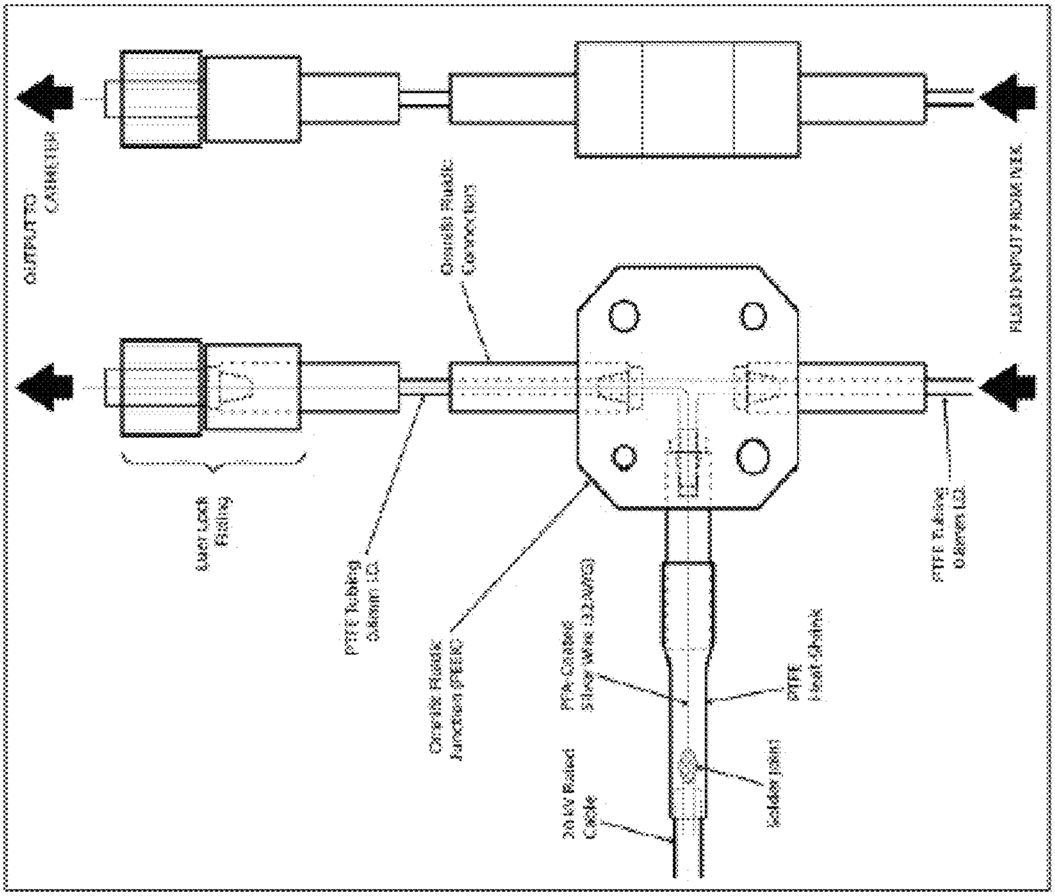
FIG. 3 is a cross sectional diagram illustrating an example electro-fluidic junction.

FIG. 2 is a system block diagram illustrating a delivery system 200 including delivery platform 100 for targeting delivery of fluid, such a dye, to tissue in vivo. The delivery system 200 includes delivery platform 100, which can insert into a bronchoscope 205. The bronchoscope 205 may insert into a patient's airway or other lumen during a medical procedure. The delivery platform 100 connects to a power supply 210 and pump 215 via an electro-fluidic junction 220. Fluid, including delivery materials, such as a dye, may be supplied to pump 215 from a reservoir 225. A switch, such as foot switch 230, may actuate power supply 210 and pump 215 contemporaneously. FIG. 3 is a cross sectional diagram illustrating an example electro-fluidic junction 220.

Referring again to FIG. 2, pump 215 is a metered fluid supply able to move a precise volume of liquid in a specified time providing an accurate flow rate. (Delivery of fluids in precise adjustable flow rates may be referred to as metering.) In an example implementation, pump 215 may supply between 1 and 500 micro liters of fluid per actuation. For example, pump 215 may supply 1 to 10 micro liters or 5 to 500 micro liters of fluid per actuation. In some implementations, the pump 215 provides 4 microliters of fluid per actuation. Pump 215 couples (directly or indirectly) to catheter 105 so that fluid travels from pump 215 to and through fluidic channel 110. In some implementations, pump 215 can have a high switching time, that is, quickly reaches steady state flow and quickly terminates flow.

Power source 210 is a high-voltage low-current supply. Power source 210 can electrically couple, directly or indirectly, to the electrode 124 via wire 120. The power source 210 may also provide a ground and electrically couple, directly or indirectly, to the conductive sheath 125, although, in some implementations, conductive sheath 125 may couple to ground via another connection. In some implementations, power source 210 is capable of providing between 3 and 10 kilovolts with a maximum current supply of less than 25 micro amps but greater than 160 nanoamps.

In operation, the fluidic channel may be primed with fluid. Bronchoscope 205 may be inserted into a patient, for example, into a patient's airway. The delivery platform 100 may then be inserted into the bronchoscope 205 and directed towards target tissue for which a precise volume of the fluid is to be delivered. Upon actuation of switch 230, power supply 210 can charge electrode 124 (and wire 120) to between 3 and 10 kilovolts. Pump 215 can provide a metered volume of fluid to the fluidic channel 110. The electrode 124, when carrying the charge, imparts or transfers the charge to the fluid traveling through the fluidic channel 110. Due to the configuration of delivery platform 100, the charge is imparted near the distal end of catheter 105 but within the fluidic channel (as compared to imparting charge exterior to the fluidic channel) so that, when charged fluid reaches a fluid/air interface near the distal opening of the catheter 105, the charged fluid forms charged droplets that disperse and form a Taylor cone.

Thus, the fluid is charged within the fluidic channel (as compared with at the fluid/air interface) and the distal opening is kept constant (e.g., the distal opening is not a nozzle, which can mechanically adjust spray characteristics, as in an atomizer or aerosol). In addition, delivery of fluid is highly localized and may be delivered to a region approximately 5 mm to 50 mm in diameter per actuation, limiting the exposure of fluid to non-targeted tissue and reducing collateral and unwanted effects. Moreover, delivery via electrically charged sprays has been shown to possess advantageous properties over other methods, as well as improved tissue penetration and uptake of fluids and materials, such as methylene blue dye. FIG. 6 is a table comparing properties of vectors for delivering molecules, such as DNA, siRNA, and proteins.

Figure 38:
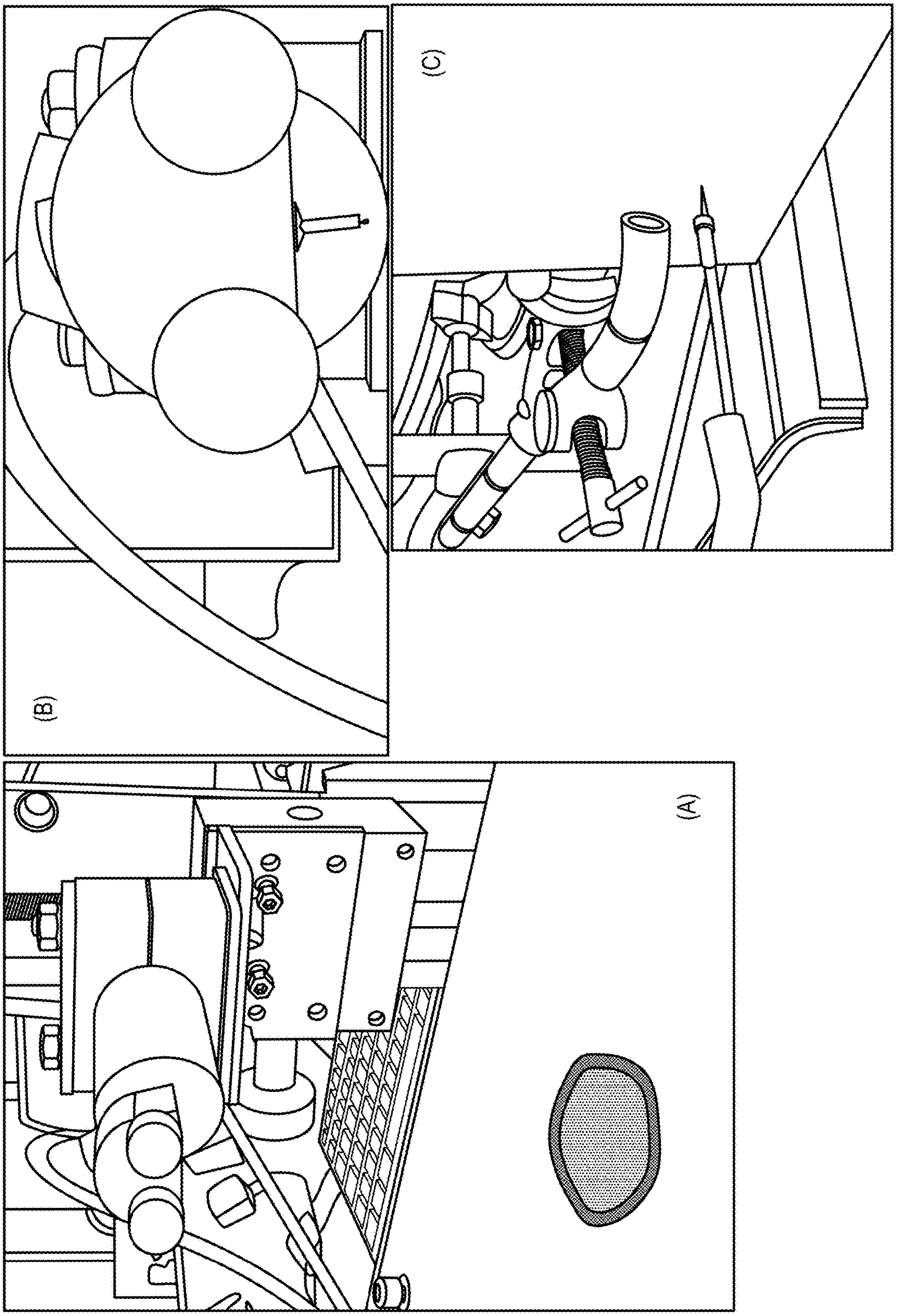
FIG. 38 illustrates a benchtop setup to test the electrospray catheter with an example porous tip. (a) a benchtop catheter setup, (b) close-up of the porous tip area, and (c) the catheter in a bronchoscope.
Figure 39:
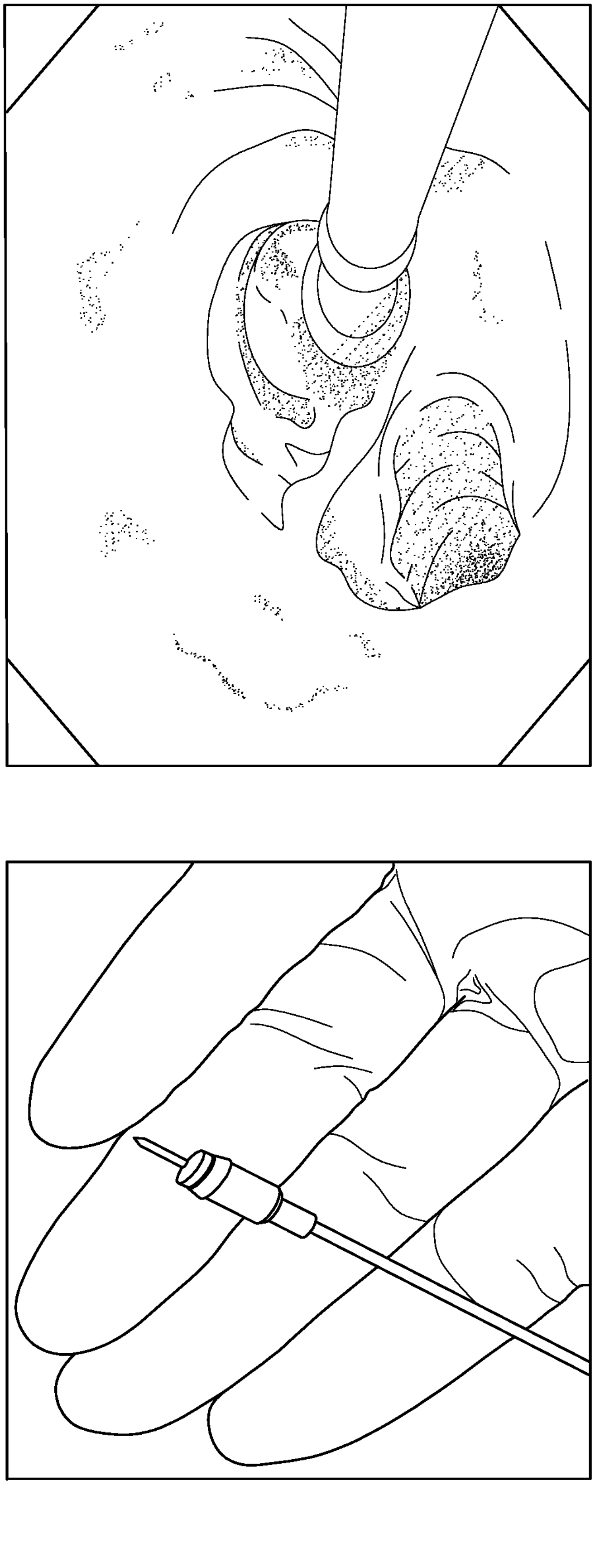
FIG. 39 illustrates (a) the electrospray catheter with an example porous tip and (b) methylene blue spray testing to ex vivo ventilated porcine lungs.

In some implementations, the electrospray apparatus may include a porous tip as in FIGS. 38 and 39 within the fluidic channel 110 at the distal end 107 of the delivery platform 100. In some implementations, the porous tip may be made of an absorbent material that can retain liquid and is porous enough to allow the retained liquid to be drawn through the porous tip by an electric field. In certain embodiments, the porosity of the porous tip can range from about 45% to about 70% on a volumetric basis. For non-limiting examples, a felt material, a fibrous material, or a filter paper formed in a cone shape can be used. The porous tip may also be made of a soft non-woven fabric that can absorb liquid and can allow the retained liquid to be drawn through it by an electric field.

As noted above, the porous tip can include material such as from synthetic fibers such as petroleum-based acrylic or acrylonitrile; or wood pulp-based rayon. Blended fibers are also possible. For example, the porous tip can be formed of one or more polymers such as polyacrylonitrile (e.g., 85% or greater acrylonitrile monomer), polyethylene, polypropylene, polystyrene, polyvinyl chloride, synthetic rubber, phenol formaldehyde resin (or Bakelite), neoprene, nylon, silicone, and the like.

The porous tip can include fibrous material in which strands of fiber have a diameter that can be sized to between 1 micron and 50 microns. For example, the porous tip can include fibrous material formed in strands having a diameter of about 1 micron, about 5 microns, about 10 microns, about 20 microns, about 30 microns, about 40 microns or about 50 microns.

Pores within the porous tip can range in size from 0.1 micron to 100 microns or more. For example, the porous tip can include fibrous material arranged to form pores including a diameter that are about 0.1 micron, about 0.5 micro, about 1 micron, about 10 micron, about 50 micron, about 75 micron, and/or about 100 micron. Other sizes are possible.

The porous tip can be formed into a number of shapes including a cone shape. In some implementations, the porous tip can be in the shape of a Taylor cone, which can improve Taylor cone formation of an electrospray. In general, the shape of the emitter head may impact the electrospraying mode. In some implementations, the porous tip can be sized between about 0.03 mm and 3 mm in diameter. For example, the diameter can be about 0.03 mm, about 0.1 mm, about 0.5 mm, about 1.0 mm, about 1.5 mm, about 2.0 mm, about 2.5 mm, or about 3.0 mm, where about is within 10%. The length of the tip and hence the total fluidic resistance presented to the sample can affect the maximum achievable flow rate for a non-continuously-fed application where fluid is drawn though the tip via the electric field. For a continuously-fed application via syringe pump or constant pressure supply, the length of the tip may have less impact, and fluid may be forced through the system rather than drawn out via the electric field. The porosity of the porous tip can be selected to be sufficient to facilitate the drawing of fluid through the tip via an applied electric field.

Figure 20:
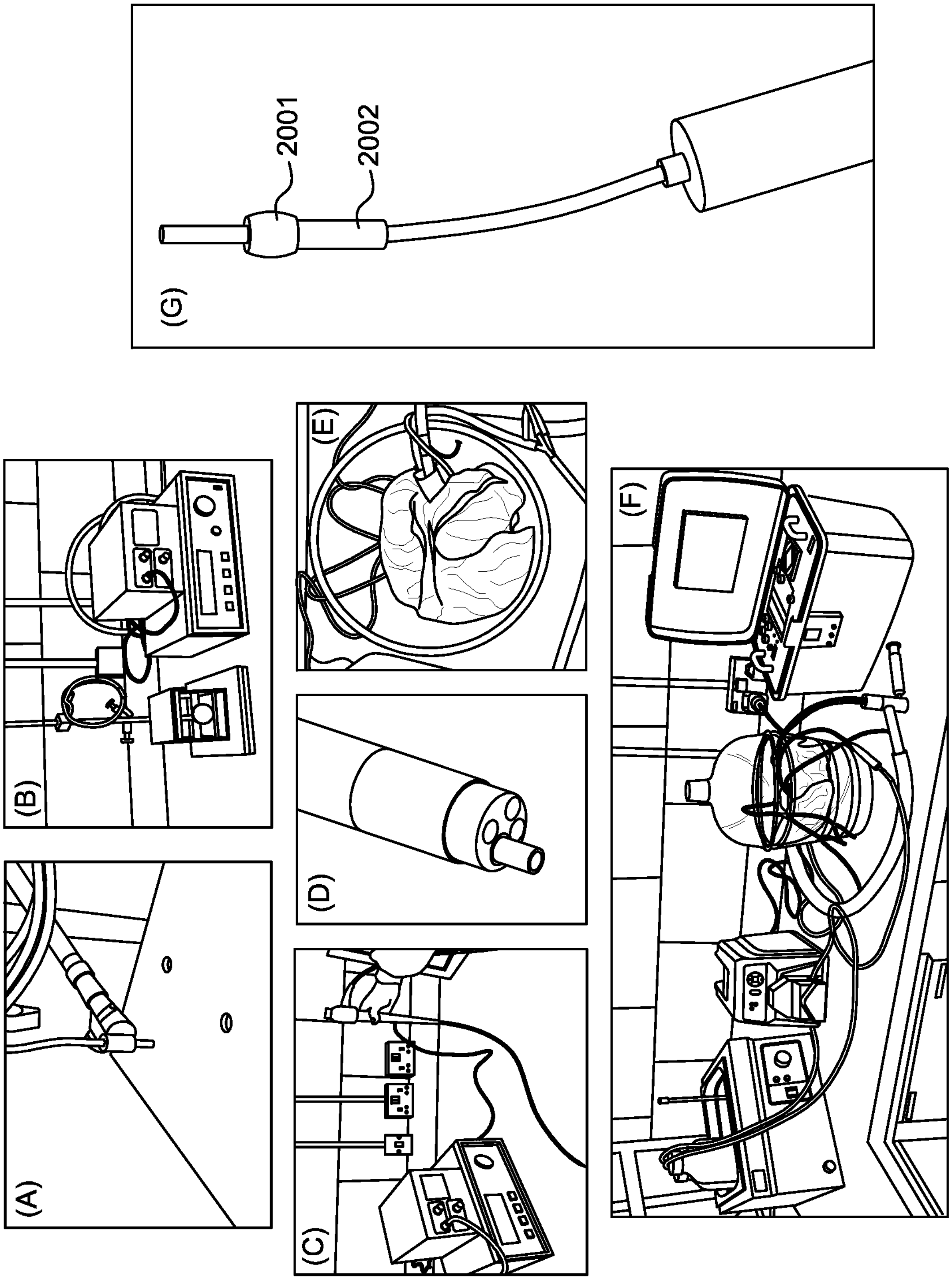
FIG. 20 illustrates bronchoscopic electrospray delivery of siRNA and mRNA to ex vivo porcine lung using an EVLP benchtop model: (a, b) electrospray apparatus; (c, d) electrospray catheter in working port of bronchoscope; (e, f) ex vivo lung perfusion circuit including a non-invasive ventilator, peristaltic pump and temperature controlled water bath; (g) electrospray catheter in working port of bronchoscope with a protrusion and thermoplastic wrap for sealing and isolation.

In operation, the porous tip may absorb fluid, provide better fluid handling, and can aid in establishing a stable cone-jet mode spray without a need for a pumping action. Further, as illustrated in FIG. 20(*g*), the electrospray apparatus may include a protrusion 2001 that is disposed near the distal opening of the catheter surrounding the outer surface of the catheter and a thermoplastic wrap 2002 that encloses the protrusion 2001. The protrusion 2001 and the thermoplastic wrap may provide sealing and insulation when the electrospray catheter is used in a working port of the bronchoscope 205.

In some implementations, a porous tip can dampen, reduce and/or eliminate the effects of peristaltic forces within the fluidic channel of the electrospray catheter that can cause fluid to move through the fluidic channel. When the electrospray catheter is moved during a procedure, peristaltic forces created by movement of the fluidic channel and connected tubing can force fluid within the fluidic channel forward, which can result in excess fluid or solution exiting the tip of the catheter unintentionally. By including a porous tip, the porous tip can act to dampen or reduce the unintentional expulsion of fluid from the electrospray catheter.

In some implementations, a porous tip can provide for greater control and/or flexibility over the operating parameters of an electrospray device. For example, adding a porous tip can allow for lower operating voltages while still creating a Taylor cone. Using lower voltages can be advantageous because a payload within the delivery solution may be sensitive to high voltages. Thus the porous tip can aid in maintaining the integrity of the payload materials. As another example, utilizing a porous tip can allow for reduced flow rates while still creating a Taylor cone. Using lower flow rates can be advantageous because limiting the amount of fluid per actuation may be clinically important for applications where the amount of fluid delivered needs to be precise (e.g., as in the case of delivering certain chemical compounds for therapeutic purposes). Moreover, lower flow rates can require lower electrical energy, e.g., voltage to form a stable spray, and lower current drawn by the process, which can be beneficial from a safety perspective. Another way to reduce the voltages can be to decrease the emitter-to-collector distance since lower distances can require lower voltages. In addition, lower distances can produce small deposition profiles, and thus a more targeted deposition can be achieved by shortening the distance between the emitter and collector.

In some implementations, the porous tip can be applied to electrospray devices and platforms that are not catheters. For example, a porous tip can be utilized within a benchtop electrospray system capable of generation of particles in the micron, sub-micron and nanoparticle ranges. As another example, a porous tip can be utilized for spraying a solution with a payload and permeabilizing agent (e.g., ethanol) to a cellular monolayer for the intracellular delivery of the payload. In another example implementation, the porous tip can be utilized within a mass spectrometry machine. Other examples include general surface coating, e.g., for printed circuit boards, and adaptive electrospraying, e.g., (Engineered Water Nano Structures) EWNS, for killing a micro-bacterial organism on fruits and vegetables.

In some implementations, the porous tip can be formed with a central, axial channel forming a coaxial electrospray tip with applications in drug or cell encapsulation. The porous tip (e.g., a fibrous cone) can include different densities with the central channel filled with a different material and/or different density of fibrous material. In some implementations, the porous tip can be utilized to electrospin, creating fibers rather than droplets. Application of such can include for local wound healing or packing in vivo delivering drugs via core—sheath fibers In some implementations, the porous tip can enable delivery of electrically conducting polymers in the form of fibers. Electrospinning same using fibrous tip to improve consistency of fibers for use in energy storage devices including capacitors and batteries. Other implementations are possible.

Although a few variations have been described in detail above, other modifications or additions are possible. For example, the fluid may include methylene blue dye (MBD). The fluid may contain DNA, siRNA, and/or proteins, which may be delivered directly to tissue. The catheter 105 may be inserted into one or more of: gastrointestinal tract, oral cavity, central airway, proximal airway, small intestine, and colon. Fluid may be delivered to a portion of one or more of: bowel tissue, parathyroid gland, sentinel node, melanoma, oral tissue, and small intestine tissue.

Other implementations are possible. By way of example and illustration, details of an example platform and uses of same are described below.

Example Implementation of Delivery Platform and System with Methylene Blue

In an example implementation, the catheter 105 is a flexible fluorinated ethylene propylene (FEP) tube 1350 mm in length, with outer diameter 1.33 mm (4 French) and an inner lumen of diameter 0.5 mm. Conductive sheath 125 is a braided shaft running the length of catheter 105 terminating 50 mm short of the distal catheter tip. The inner lumen of the catheter 105 serves as the fluidic channel 110 and houses wire 120, which is a single strand silver wire of 0.2032 mm (AWG32) coated with perfluoroalkoxy (PFA) to a final O.D. of 0.254±0.012 mm, which forms the insulation layer 122. The proximal end 106 of the catheter 105 terminates in a Luer-lock fitting for attachment to a three-way fluidic junction 220 to allow the combination of the PFA-coated wire 120 with pump 215. The coated silver conductor (e.g., electrode 124) terminates 100 mm from the distal outlet 115 of the catheter 105 and is uncoated (e.g., exposed) over the final 2 mm to allow electrical connection with fluid.

The length of the example delivery platform (1350 mm) allows unencumbered operation of the bronchoscope without excessive loose tubing and has an external diameter of 2.0 mm to allow facile insertion into bronchoscope entry ports. The minimum bend radius of the example delivery platform is 8 mm to allow manipulation during bronchoscopy procedures without damage, and the example delivery platform is not damaged by bending of this severity for more than 100 cycles. Should the example delivery platform be over-flexed and fail, any dye leak from the inner lumen is contained to prevent complications to the patient and/or operator. The example delivery platform operates between 10° C. and 60° C. without change in performance and is not intended for use in high- or low-pressure environments. The exterior of the example delivery platform is smooth and lubricious for easy passage via bronchoscope tool channel. All materials used in construction of this example delivery platform are approved for use in Class IIb medical devices by the American Food and Drug Administration.

Figure 4:
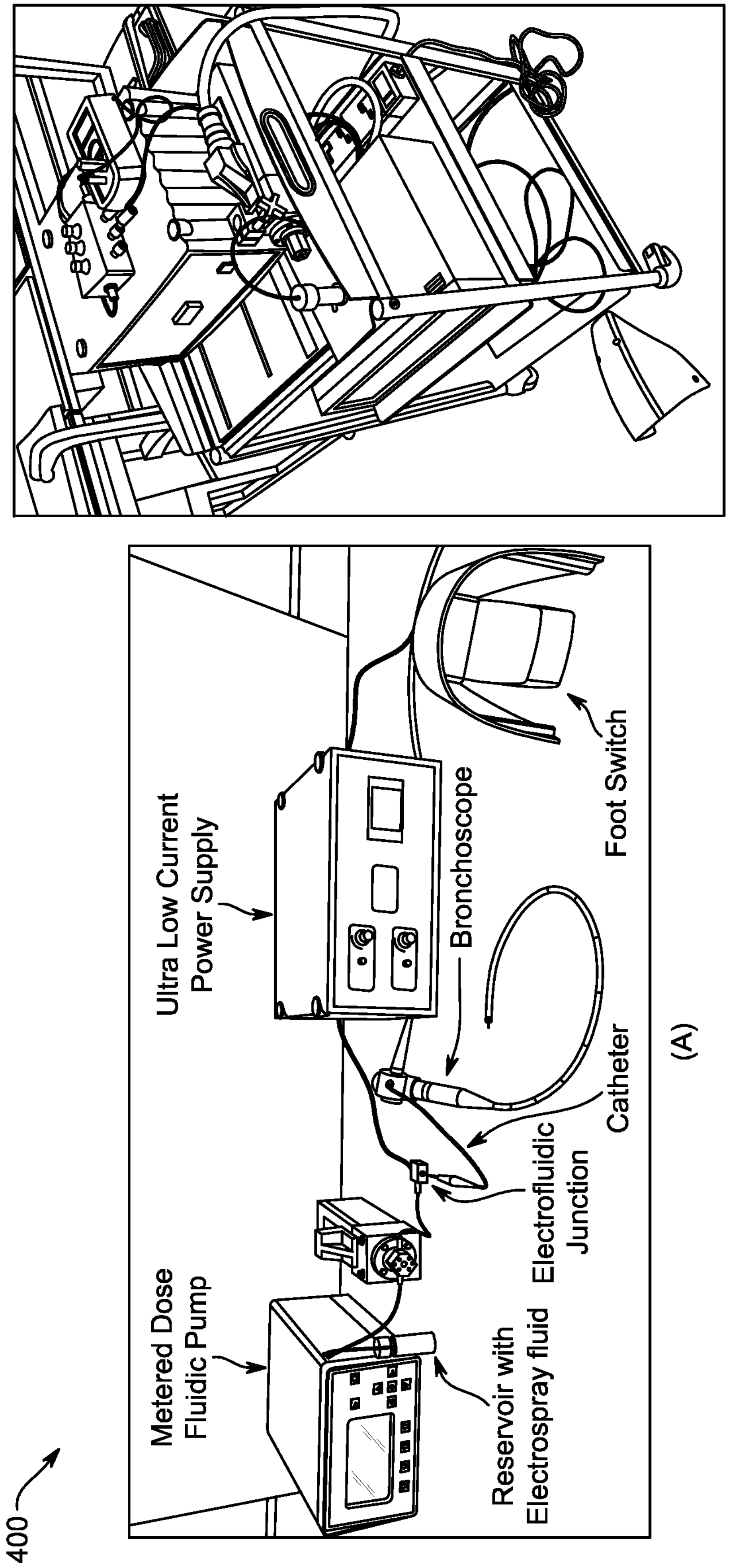
FIG. 4 is a picture illustrating an example implementation of a delivery system with the example delivery platform (a) in a benchtop setup and (b) in a medical trolley.
Figure 14:
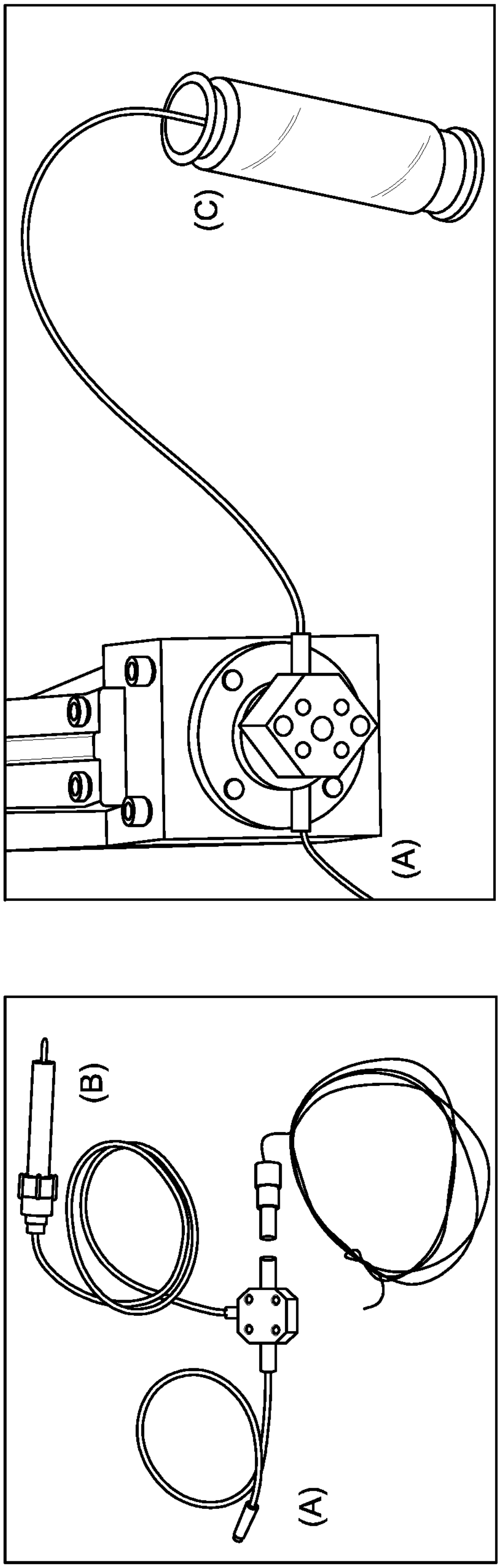
FIG. 14 includes pictures illustrating components of the example implementation shown in FIG. 4.

FIG. 4 is a picture illustrating an example implementation of a delivery system 400 with the example delivery platform. FIG. 14 are pictures illustrating components of the example implementation shown in FIG. 4. FIG. 4(*a*) shows a bench-top setup for the components and FIG. 4(*b*) shows an exemplary implementation in a medical trolley. The medical trolley may include lockable anti-static castors. The example delivery system 400 delivers an adjustable, controlled quantity of dye via an electrically charged spray to the lung. The example delivery system 400 does not impose upon either the operator or patient a risk of electric shock during use at supply voltages of between 0 and 10 kilovolts. During use, dye should not be present at the catheter tip before the charged spray is initiated or after it is terminated. The example delivery system 400 can be operated by a single user and can be activated via a single-press foot-switch device. Delay between depression of the operator's foot-switch and initiation of electrospray is minimal, and in all cases below 1 second.

The example delivery system 400 displays no hysteresis over 50 electrosprays, allowing repeated doses to be delivered accurately in a single diagnostic intervention. The example delivery platform is intended to deliver up to 50 electrosprays in a single diagnostic intervention, indwelling time lasting no more than 20 minutes. In accordance with ISO 10993 the example delivery platform is therefore classified as "limited contact (<24 hours)" or "Transient Use" in accordance with design classification Rule 5. The example delivery platform is single-use and is not intended for re-sterilization or reuse in multiple patients.

Figure 5:
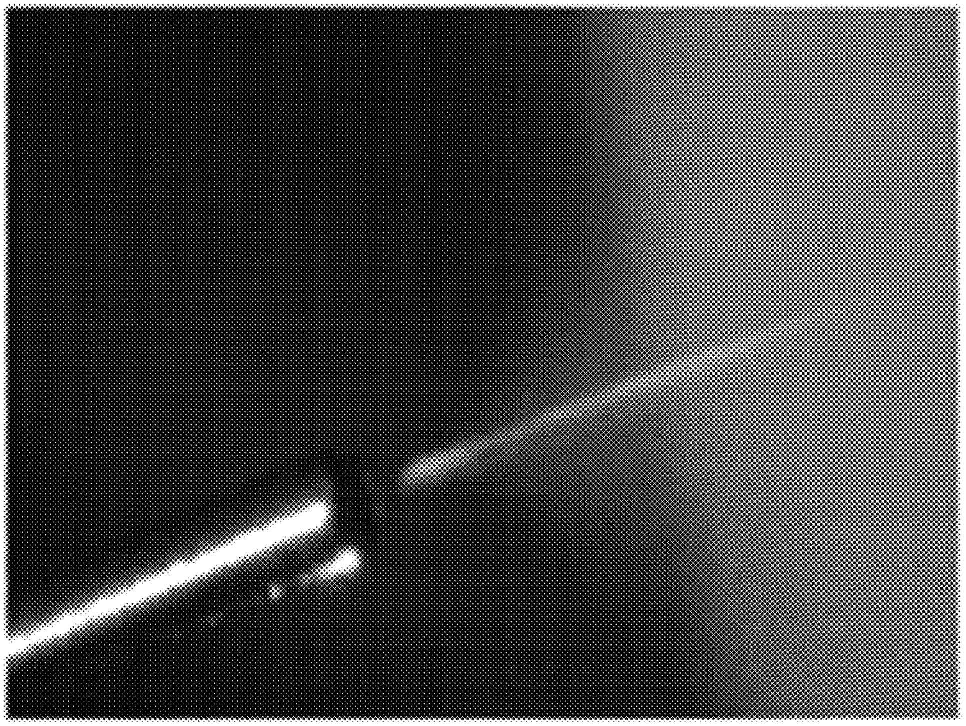
FIG. 5 is a picture illustrating plume dispersion in the example delivery platform.

When the foot-switch device is actuated, the silver wire is charged to between 3 and 10 kV via a high-voltage low current supply, which in turn charges the dye within the catheter. The charged dye delivers via a metered pump to the catheter outlet port, creating a dye/air interface at the catheter outlet. The charges within the dye migrate to this interface and repel one another, directly countering surface tension and leading to the formation of a conical distension known as a Taylor cone. Provided the dye carries a sufficient charge this Taylor cone elutes at its apex to form a spray of charged droplets, which disassociate from one another to form plume dispersion. FIG. 5 is a picture illustrating plume dispersion in the example delivery platform. This jetting and dispersion is used to deliver the dye to the lung, and is terminated by withdrawing the dye into the catheter tubing by means of reversing the metered pump used in the dispense process.

The catheter component is constructed from fluorinated ethylene propylene (FEP), which complies fully with USP Class VI and all current ISO standards, and is entirely non-cytotoxic, non-pyrogenic and non-haemolytic. Further, FEP is shown to possess excellent particle-shedding properties to minimize potential debris deposition within the lung. Voltage carrying wires within the catheter are perfluoroalkoxy (PFA)-coated Silver to maximize biocompatibility.

In the example illustrated in FIG. 4, the following components are included:

1) A metered dye dispensing system capable of accurate delivery of the dosage volumes;
   IVEK Inc. DigiSpense 3020 Actuator and Controller; or Smiths Medical Medfusion® 3500 Syringe Pump with PHARMGUARD® v5 Software;
   Beckton Dickinson—Sterile disposable syringe 60 ml Plastilok with 50 mm luer lock
2) An ultra low current, high voltage DC power supply for fluid charging;
   Spraybase/Spellman Inc.;
3) A footswitch to commence the delivery;
   Schaltgeraete GmbH & Co. KG.
4) Medical Grade Tubing;
   Smiths Medical Sterile Extension Set.

The following illustrates an example procedure for preparing a patient.

1. Verify the patient is a good candidate for bronchoscopy under moderate sedation prior to initiation.
2. Prepare the patient for bronchoscopy. Follow patient management protocols according to staffing, training, and individual institution-specific policies and guidelines for bronchoscopy.

3. Introduce the flexible bronchoscope through the nose or mouth as appropriate.
4. Navigate the bronchoscope to the targeted site and position the bronchoscope so that the targeted site is in bronchoscopic view.
5. Prepare the airway by washing with 0.9% saline (+/−mucolytic agents) and aspirate clear any mucus or secretions.

The following illustrates and example process for using the example delivery platform and system.

1. Before inserting the catheter into the bronchoscope, ensure the protective sheath has been removed from the distal end
2. Advance the Catheter through the bronchoscope until the market band on the distal tip of the Catheter shaft is in bronchoscopic view. If the device encounters significant resistance during insertion, do not apply excessive force. In especially tortuous anatomy it may be necessary to relax the bronchoscope's deflection mechanism until the device passes smoothly.
3. Advance the Catheter to the targeted site under bronchoscopic vision. Do not advance the Catheter into bronchi in which the Catheter cannot be seen under bronchoscopic vision. Advancing the catheter under such conditions may result in pneumothorax, or other injury to the patient.
4. Do not reposition the bronchoscope with the Catheter advanced beyond the distal end of the bronchoscope as this may result in harm or injury to the patient.
5. Position the Catheter in the airway near to the target area. Avoid touching bronchial wall with the catheter end as this may impair Catheter function.
6. Deliver methylene blue to target area, by pressing and releasing the footswitch once. The Control Module will deliver energy automatically according to pre-set parameters for time, voltage and current.
7. Once the procedure is complete and prior to manipulating the bronchoscope, withdraw the Catheter approximately 10 cm into the bronchoscope so the electrode array is proximal to the bend in the distal tip of the bronchoscope.
8. Once the treatment is complete, remove the Catheter from the bronchoscope. Disconnect the Catheter from the Controller, and dispose of the used Catheter per biohazard procedures.

If mucus builds up in the airways and obscures visualisation, remove the catheter from the bronchoscope, provide irrigation with sterile saline, and suction the resulting fluid from the airways. If the spray is not delivered, remove the Catheter from the bronchoscope. Clean the distal end of the catheter with a dry sterile swab. Confirm the Catheter has been primed and press footswitch to visually confirm that the Catheter is functioning properly. If it is not functioning properly, replace the Catheter and continue with the procedure.

Experiment 1—Ex Vivo and In Vivo Large Animal

Ex Vivo

Figure 7:
FIG. 7 includes two images showing pig trachea with methylene blue stain applied via dripping (left) and electrospray (right), the electrosprayed dye stains the tissue, whereas dropped on dye washes off easily showing electrospray as a viable vector for dye delivery into cells.

Preclinical studies were performed using an ex vivo model of freshly excised porcine lungs. Using the same fluid and electrical supply equipment as the Bench Studies, 0.05% methylene blue solution was delivered via electrospray to various sites within the lung including both large and small airways. FIG. 7 includes two images showing pig trachea with methylene blue stain applied via dripping (left) and electrospray (right), the electrosprayed dye stains the tissue, whereas dropped on dye washes off easily showing electrospray as a viable vector for dye delivery into cells.

Dose responses were carried out by electrospraying various concentrations of methylene blue onto normal pig lungs and dissected airway tissue. The concentration of methylene blue that gives minimal staining when electrosprayed onto dissected pig airway tissue is 0.03-0.05% methylene blue in WFI.

Criteria evaluated during animal studies were as follows; spark formation, electrosprayed droplet size, electrical sensation/shocks to operator, effect of bronchoscope/catheter fouling with mucus, effect of catheter distance from target, specificity of target area, delay of electrospray after foot switch actuation, repeatability of electrospray under identical conditions.

The primary function of the device is to comminute or atomize small volumes of fluid safely within the lung and airways via electrospray. Calculations to eliminate or mitigate risk were performed as well as to ensure an electrospray is produced. Calculations pertaining to the electrospray plume were confirmed by experimentation. Calculations pertaining to the device form factor were made relative to the requirement to use it with a standard video bronchoscope. In designing the device, some calculations were confirmed by experimentation and some experimentally obtained electrospray parameters were generalized by calculation.

(i) Calculations of the dielectric constant of the catheter materials to insulate the central conductor from the patient and the operator in all circumstances.
(ii) Calculating the length braided earth shield over the length of the catheter shaft. (1250 mm)
(iii) Calculating the minimum dead volume to determine pump priming volume (960 uL)
(iv) Calculations of the ideal kV volt values to create an electrospray from the device with the chosen fluid—normally Methylene Blue. (4.5 kV)
(v) Calculation of the ideal length of the entire catheter. (1350 mm) (vi) Calculation of minimum bend radius of catheter (8 mm)
(vii) Calculation of maximum width of catheter (2 mm) (~6 French)
(viii) The maximum current required to produce an electrospray was calculated/predicted using the Taylor/Melcher model (160 nA)
(ix) The dispense time and volume flow rate had to be calculated to deliver the dose in the minimum time. Constraints on this calculation included a max flow rate to maintain an optimized spray pattern. (200 uL/min)

In-vitro tests Aims: In-vitro tests were carried out in which freshly dissected porcine airway tissue was electro sprayed ex vivo with methylene blue. The aims of these tests were: (i) to determine the parameters under which methylene blue can be successfully electrosprayed; (ii) to carry out a dose response to observe the staining pattern produced over a range of methylene blue concentrations; and (iii) to optimize a protocol for delivery of methylene blue via electrospray onto normal airway tissue such that minimal staining occurred.

Methods: Sections of airway tissue approximately 1 $cm^2$ were cut and placed into tissue culture plates. A range of concentrations of methylene blue solution (0.008%, 0.015%, 0.031%, 0.04%, 0.05%, 0.063%) were made up and electrosprayed onto the dissected airway tissue. Voltages and flow rates were varied during the electrospray process in order to determine which set of conditions were conducive to production of stable electrosprays. The length of time that the dye was left on the tissue prior to rinsing was varied (15, 30, 60 sec). After spraying, the tissues were rinsed with a saline solution in order to observe the intensity of staining of the tissue post-spray.

Results: Parameters (voltages and flow rates) were identified at which methylene blue could be successfully electrosprayed in vitro onto pig airway tissue. The dose response study determined that 0.05% methylene blue appeared to be the lowest concentration at which a stain could be observed at the shortest incubation time of 15 sec. No staining was observed at the 15 sec time point with concentrations lower than 0.05%.

Conclusions: A wide range of methylene blue concentrations can be successfully electro sprayed by varying the voltages and flow rates used. A solution of 0.05% methylene blue appears to be the cut off level below which no staining is visible on normal airway tissue at the shortest incubation time tested here which was 15 sec. This time was deemed to be similar to the length of time in the clinic that it would take between delivery of dye and rinsing.

Mechanical and electrical tests: An electrical measurement circuit was established to perform test measurements during the design phase. Parameters tested included:

(1) Central conductor potential (4.5 kV);

(2) Potential (reverse) gradient within electrospray plume from point of elution to deposition substrate/tissue (>5 kV/mm);

(3) Current (Ionic Current+Charge on fluid colloids) (50 nA+100 nA);

(4) Insulation dielectric withstand test (PFA, FEP) (>80 kV/mm);

(5) Tests for leakage currents and effect of guarding & shielding (<<Noise Floor); and (6) Device generated currents:

a. External Offset Current (<<Noise Floor);

b. Triboelectric Effects (<<Noise Floor);

c. Piezoelectric (<<Noise Floor) and Stored Charge Effects (Energy source includes make-before-break grounding of HV yielding Stored Charge Effects ~0).

An electrometer (Keithley Model 6517B) was used perform a battery of tests to characterize the device. During energization, no leakage current could be detected along the exterior shaft of the catheter, the fluidic or electrical connections. A mechanical bend test was performed (100 cycles) on 8 mm bend radius to visually/microscopically check for mechanical wear to investigational catheter device. No wear was observed.

The investigational device was used in an ex-vivo porcine lung model. The device was used with an Olympus EVIS Exera BF-1T160 Bronchoscope and the test(s) objective was to deliver 10× repeated 20 uL sprays to different areas in the proximal porcine airways reliably.

The data was recorded on the video card on the scope and repeated administration was demonstrated. The test was repeated ~20 times including on successive days.

Performance tests. Testing of prototype device was conducted using 0.05% methylene blue solution delivered via IVEK Digispense 3020 metered delivery system, and high voltage supply was achieved via a Control Unit. The high voltage supply may be protected with a surge protector to prevent sparks, and the Control Unit may incorporate an electrometer. The catheter device was tested for electrospray formation within an Olympus EVIS Exera BF-1T160 Bronchoscope at voltages ranging from 0 to 10 kV. During testing criteria evaluated were as follows; spark formation, electrosprayed droplet size, electrical sensation/shocks to operator, effect of bronchoscope/catheter fouling with lubricant, effect of separation between catheter tip and electrospray target, delay of electrospray after foot switch actuation.

The optimal parameters for electrospray delivery of a 0.05% methylene blue solution were 6 kV voltage, 10 μl/second delivery rate and 21 mm distance from the device to the target area. The applied 6 kV voltage was the minimum voltage required to enable diffuse electrospray delivery of 10 μl methylene blue. In the tests conducted both 10 mm and 21 mm distance was evaluated and both resulted in similar electrospray using 0.05% methylene blue solution. However, 21 mm distance was determined from the large animal studies as the optimal working distance for targeted delivery of methylene blue onto the airway wall in vivo.

An evaluation of biological safety. The example delivery platform is designed to be entered into the lung during endoscopic procedures and is in contact with mucous membranes of the lung for <24 hours. Biocompatibility testing as recommended by ISO 10993 for limited contact devices is therefore recommended. The catheter component is constructed from fluorinated ethylene propylene (FEP), which complies fully with USP Class VI and all current ISO standards, and is entirely non-cytotoxic, non-pyrogenic and non-haemolytic. Further, FEP is shown to possess excellent particle-shedding properties to minimise potential debris deposition within the lung. Voltage carrying wires within the catheter are perfluoroalkoxy (PFA)-coated Silver to maximise biocompatibility.

In Vivo

Sixteen (16) normal pigs were used as an acute large animal model to substantiate the in vivo effectiveness of the device design. Each pig received 3 sprays of methylene blue with each spray lasting 1 second.

The example delivery platform was successfully used to deliver a dye—methylene blue—to pig airways in a proof of principle study. Following this, in vivo experiments were performed. These experiments involved anaesthetised pigs who underwent a bronchoscopy. This bronchoscopy allowed the investigators to inspect the surface anatomy, collect samples of bronchoalveolar fluid and electrospray methylene blue. No adverse effects were noted in either the macroscopic airway appearance or bronchoalveolar lavage results 4 days after the electrospray application of methylene blue.

Rationale for selection of the model. The aim of the broad project is to translate technology to a 'first in man' diagnosis of lung cancer. For this work, it was not possible to use large animal models of lung cancer for several reasons. In general, the incidence of spontaneous lung cancer in animals is low. The Jaagsiekte sheep retrovirus (JSRV) that is a causative agent responsible for contagious lung tumors in sheep is not found in Ireland. Consultation with veterinarians revealed that the likelihood of getting permission from dog owners to use dogs with lung cancer was extremely low. Small laboratory animal models of lung cancer induced with chemicals would not be suitable for these bronchoscopy studies. Therefore, normal pigs or sheep were options for a large animal model for this project to substantiate the in vivo safety and effectiveness of the device design. Pigs were selected as the model because, unlike sheep, young animals of specific size are available all year round to ensure consistency of the model.

Study objectives. The aims of the in vivo large animal studies were to:

(i) substantiate the practicability of the device for the clinician;

(ii) determine the effectiveness of the device to deliver dyes directly to specific sites (i.e. targeted delivery) in large animal airways in vivo;

(iii) select a dye that is suitable for use as a differential stain for tumors based on the following features in normal airways:

desired spreadability over the target area;

minimal residual staining of the target area post-rinsing;

(iv) devise a protocol that results in minimal staining of non-tumour areas;

(v) further refine the design of the device in order to optimise the protocol;

Conclusions:

substantiate the practicability of the device for the clinician the clinicians were directly involved in all studies and provided feedback that lead to refinement of the device and the protocol for delivery of dye (ii) determine the effectiveness of the device to deliver dyes directly to specific sites (i.e. targeted delivery) in large animal airways in vivo;

it was confirmed that the device was capable of delivering dyes directly to specific sites within the airways of a living and breathing large animal without encountering any difficulties due to air movement.

(iii) select a dye that is suitable for use as a differential stain for tumors based on the following features in normal airways:

desired spreadability over the target area minimal residual staining of the target area post-rinsing were confirmed (iv) devise a protocol that results in minimal staining of non-tumor areas;

a protocol was devised (v) further refine the design of the device in order to optimize the protocol;

the device was further refined in an iterative manner throughout the series of animal studies.

The refinements included:

Removal of 2.4 mm plastic sheath at distal end extending 5 mm beyond the catheter tip since this was causing pooling of dye between the internal radius at the sheath and the catheter tip. The removal of the plastic sheath resolved this problem.

Introduction of grounded braided shaft extending the length of the catheter and ending 50 mm short of the catheter tip to stiffen and protect the catheter shaft and to protect the patient from the central conductor in an insulation fault condition.

Use of a softer plastic at the catheter tip to reduce risk of local lung trauma.

Introduction of a marker band 10 mm from tip to aid the operator in locating the how far the catheter has advanced relative to the end of the scope.

Reduction of the inner fluid channel lumen from 800 microns to 500 microns in diameter. The reduced inner diameter minimises local peristaltic flow due to bronchoscope flexure. Such flow has not been evident or problematic.

Experiment 2—Ex Vivo Human Lung Tissue (Resected Human Lung Tumor)

A further study using ex vivo human lung cancer tissue was performed at the Mater Misericordiae University Hospital. It concluded that a differential methylene blue stain between normal tissue and lung cancer can be achieved. For this study, 11 patients were recruited between April 2012 and July 2013. These patients had confirmed lung cancer and underwent surgical removal of their cancer (lobectomy). Following thoracic surgery, sections of both healthy and cancerous tissue that were not required for diagnosis were evaluated. This allowed the identification of an optimal concentration range of methylene blue that would obtain a differential stain between lung cancer and normal tissue (when applied with an electrospray).

The concentration of methylene blue that gives optimal differential staining when electrosprayed onto human lung cancer tissue is 0.03-0.05% methylene blue in WFI.

Characterizing Methylene Blue in Electrospray

The electrospray technique utilized in the example delivery platform and system finds its first and widest application as a means of generating ions in mass spectrometry (Santos L S, A Brief Overview of the Mechanisms Involved in Electrospray Mass Spectrometry, in Reactive Intermediates: MS Investigations in Solution, 2009, Wiley-VCH Verlag GmbH & Co. and Le Gac S, Van Den Berg A, Miniaturization and Mass Spectrometry, S, 2008, RCS Publishing). Electrospray Ionization (ESI) is defined as a soft ionization technique because it can be applied to ionize large molecules such as polymers, proteins, peptides and nucleic acids without fragmenting them. During the ionization process, the molecules acquire enough energy to be transferred to the gas phase but the amount of energy remains low enough not to induce any fragmentation.

The dye methylene blue has been subjected to ESI in a number of studies with a number of publications reporting ESI mass spectra for methylene blue (Yang F, Xia S, Liu Z, Chen J, Lin Y, Qiu B & Chen B, Analysis of methylene blue and its metabolites in blood by capillary electrophoresis/electrospray ionization mass spectrometry, Electrophoresis 2011, 32, 659-664 and Nogueiraa F, Lopesa J H, Silvaa A C, Gonçalvesa M, Anastácioa A S, Sapagb K, Oliveira L, Reactive adsorption of methylene blue on montmorillonite via an ESI-MS study, Applied Clay Science, 2009, 43 (2), 190-195). To verify that the chemical structure of methylene blue is not altered by the electrospray technology, UV-Vis spectroscopy and 1H NMR (nuclear magnetic resonance) analyses were carried out.

UV-Vis analysis. As reported in the Merck Index, methylene blue has absorption peaks at 668 and 609 nm. The absorbance profiles of a methylene blue sample before and after electrospraying were compared. According to Beer-Lambert's law, absorbance intensity is proportional to concentration. If methylene blue was degraded by the electrospray process, its absorption profile at 668 and 609 nm would change with respect to the absorbance of the same methylene blue sample before electrospraying.

Figure 8:
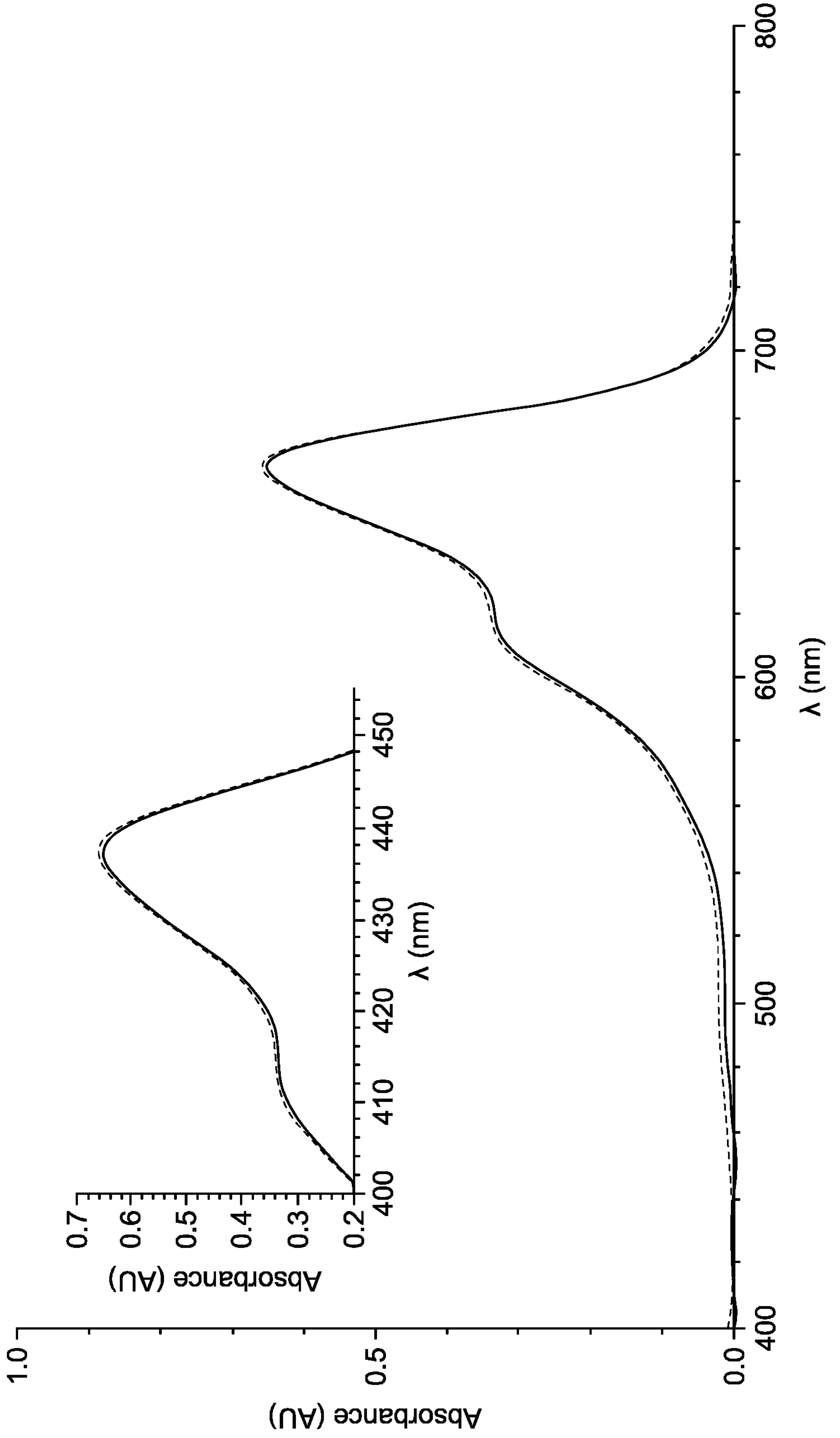
FIG. 8 illustrates a overlay of the spectra recorded for methylene blue before and after an electrospraying process, suggesting negligible or no alteration of the chemical structure of the dye.

The spectra shown in FIG. 8 demonstrate a good overlay of the spectra recorded for methylene blue before and after the electrospraying process, suggesting negligible or no alteration of the chemical structure of the dye. In FIG. 8, visible light spectra for a 0.05% methylene blue solution before (–) and after (–, –) electrospraying. Electrospray setup: 3.5 cm distance emitter-collector, 6.5 kV voltage applied to the emitter, 0.5 ml/min flow rate. The plot in the inset represents a magnification of the spectra.

For reference, a graph published on the open access online journal Scientific Reports (Liu H, Gao N, Liao M & Fang X, Hexagonal-like Nb2O5 Nanoplates-Based Photodetectors and Photocatalyst with High Performances, 12th January 2015, Scientific Reports 5:7716, DOI 10.1038/srep07716) and showing degradation of methylene blue is shown in FIG.

Figure 9:
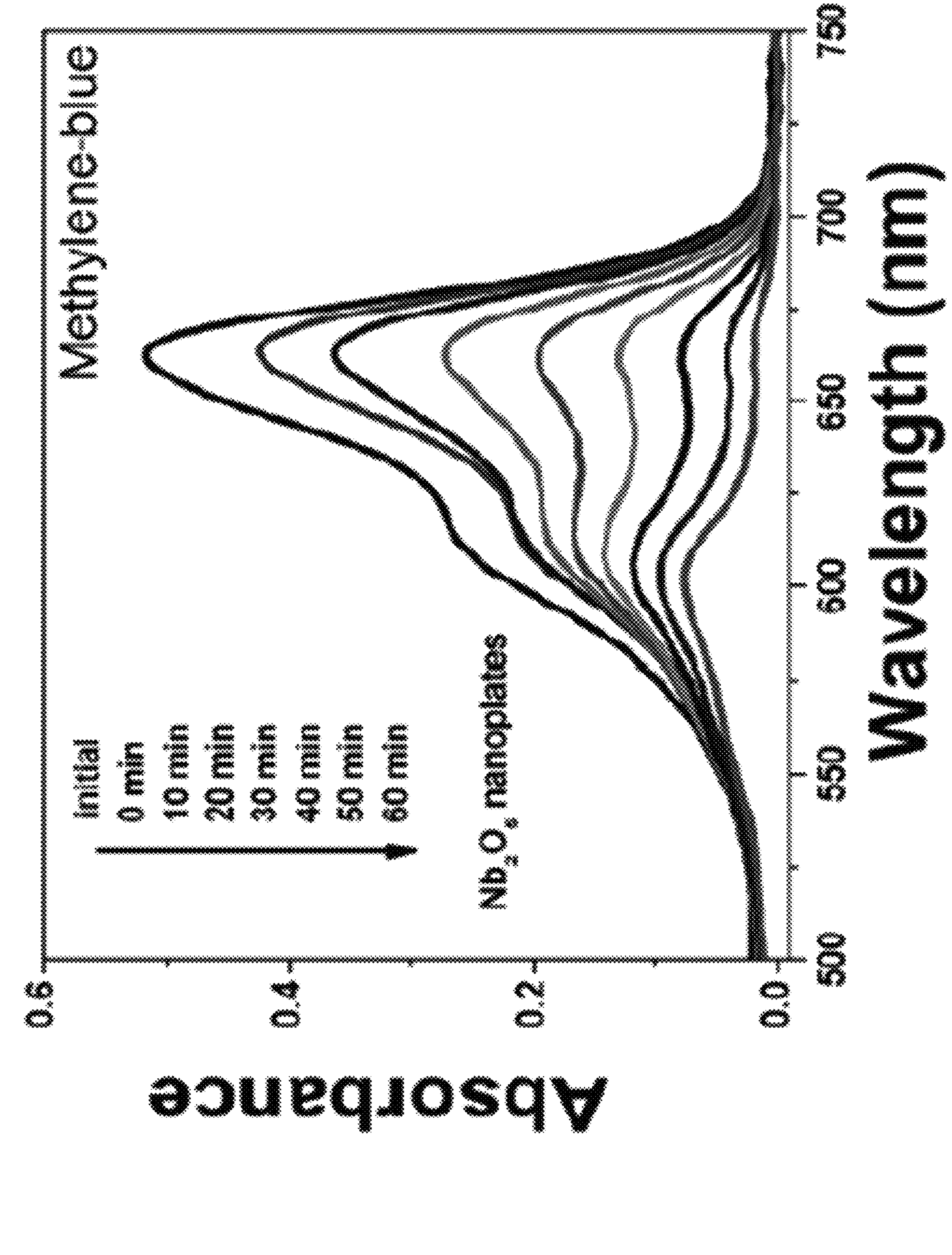
FIG. 9 illustrates photocatalytic decomposition of methylene blue.

9. FIG. 9 illustrates photocatalytic decomposition of methylene blue. The degradation of methylene blue over time is monitored by means of UV-Vis spectroscopy. The black trace represents an untreated sample of methylene blue. The lower absorbance intensities of the colored traces are due to decomposition of the dye exposed to the degrading agent Nb2O5 for different times.

Figure 10:
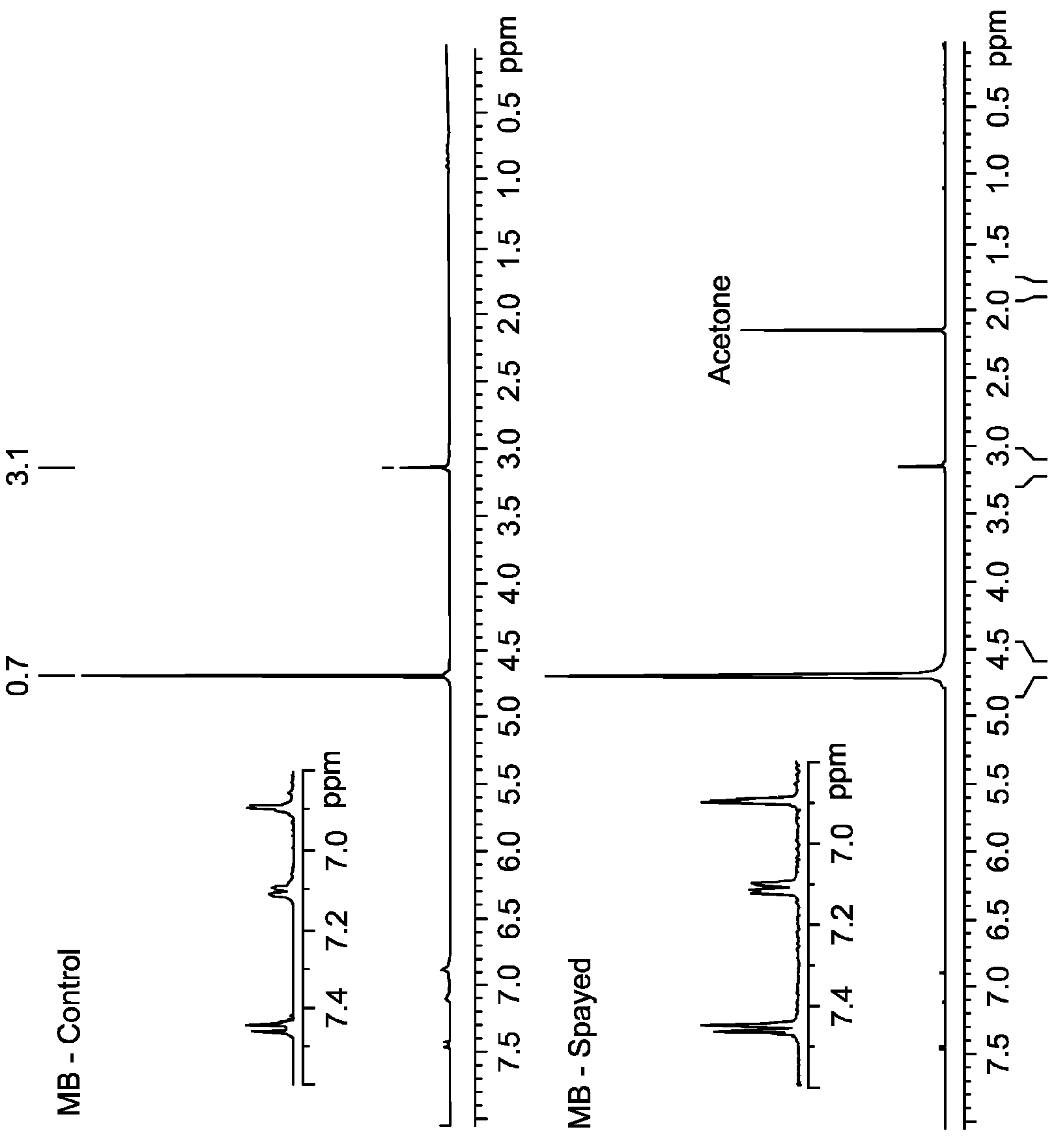
FIG. 10 illustrates proton nuclear magnetic resonance (1H NMR) spectra of methylene blue before and after electrospraying.

FIG. 10 illustrates 1H NMR spectra of methylene blue before and after electrospraying. Nuclear magnetic resonance is a very sensitive technique to assess purity of a material as it is capable of detecting very small amounts of impurities. In this specific case, additional peaks would appear if there were protons in a different chemical environment due to degradation of the compound of interest. It can be observed from FIG. 10 that the peaks for both specimens have identical multiplicity and chemical shift. This characteristic together with the absence of new peaks in the sprayed sample indicate that the structure of methylene blue is preserved during the electrospray process. In FIG. 10, 1H NMR of 0.06% methylene blue and 0.06% methylene blue electrosprayed. Electrospray setup: 3.5 cm distance emitter-collector, 6.5 kV voltage applied to the emitter, 0.5 ml/min flow rate. Note: the tubing of the instrument was rinsed with acetone in order to remove traces of water resulting in a line at 2.2 ppm due to acetone.

Conclusions: The example delivery platform and system is based on electrospray technology, which is a gentle technique to ionize materials. Based on the data above, UV-Vis and 1H NMR spectra provided evidence that this process does not alter or degrade methylene blue.

Methylene Blue and Lung Cancer Diagnostics

Methylene blue is widely used as a dye and stain for a range of clinical applications. Methylene blue infusion is considered a safe and effective method of localizing abnormal parathyroid glands. Methylene blue is an effective and cheap alternative to isosulfan blue dye for sentinel lymph node localization in patients with breast cancer. The technique of methylene blue staining was originally described in 1933 by Japanese investigators for improving the diagnosis of early gastric cancer. Today, gastroenterology staining with methylene blue during endoscopy is a well-established method allowing a prediction between neoplastic and non-neoplastic lesions with high specificity. Methylene blue staining is also used for noninvasive diagnosis of melanoma and oral cancers. Lung cancer has still a very poor prognosis compared to other types of cancer and while the diagnostic value of flexible bronchoscopy for various pulmonary diseases is well established, staining during white light bronchoscopy (chromobronchoscopy) has not been added to the diagnostic panel of pulmonary endoscopy up to now. Three studies have been reported with mixed findings regarding the efficacy of methylene blue staining for identification of malignant and premalignant lesions in a prospective manner. No adverse safety findings were reported and further research on chromobronchoscopy for pulmonary diseases was recommended by all three groups. The clinical uses, proposed mechanism of action and safety of methylene blue in cancer diagnostics will be discussed below.

Vital Staining for Cancer Diagnosis

There are numerous diagnostic adjuncts available for cancer diagnosis. Cytological methods, tissue staining techniques, and molecular methods are widely used. Supravital staining has long been used as an adjunct in the early diagnosis of malignant lesions. In 1920's/30s, Schiller (Schiller, W. Early diagnosis of carcinoma of the cervix. Surg. Gynec. Obstet. 56 (1933). 210) first reported the use of Lugol's iodine solution in carcinoma of the uterine cervix. In vivo staining has been extensively used in gynaecological practice for the detection of malignant change of the cervix during colposcopy. The technique has been applied in the oral setting for over 30 years by means of the dye toluidine blue (TB) (Kerawala C J, Beale V, Reed M, Martin I C. The role of vital tissue staining in the marginal control of oral squamous cell carcinoma. Int J Oral Maxillofac Surg 2000; 29:32-5). Apart from TB, other stains such as methylene blue, Lugol's iodine, and acetic acid have also been tried in the diagnosis of cancerous lesions.

Methylene blue belongs to the family of phenothiazonium compounds. It is a cationic species and it is a basic dye (FIG. 11). Methylene blue is widely used as a dye or staining agent to make certain body fluids and tissues easier to view during surgery or on an x-ray or other diagnostic exam. FIG. 11 illustrates proposed structures for methylene blue. Both structures shown in A and B have been proposed for MB+; however most chemists agree that the structure of MB+ is Structure A.

Clinical Uses of Methylene Blue in Cancer Diagnostics

Barrett's Oesophagus

Barrett's oesophagus is considered to be a premalignant lesion and is found in 10-20% of patients undergoing upper gastrointestinal (GI) endoscopy for symptoms of gastro-oesophageal reflux disease (GORD). The normal squamous epithelium is replaced by a specialised columnar epithelium referred to as intestinal metaplasia. Intestinal metaplasia can evolve into adenocarcinoma in a well-defined metaplasia-dysplasia-carcinoma sequence. Highly dysplastic or malignant Barrett's oesophagus stains differentially with methylene blue. Increased heterogeneity and decreased methylene blue stain intensity are significant independent predictors of high grade dysplasia and/or cancer (Canto M I, Setrakian S, Willis J E, Chak A, Petras R E, Sivak M V. Methylene blue staining of dysplastic and nondysplastic Barrett's esophagus: an in vivo and ex vivo study. Endoscopy. 2001 May; 33(5):391-400). It has been reported that a targeted biopsy is possible to limit because methylene blue only stains non-dysplastic Barrett's mucosa but not dysplastic ones. However, many of supplementary studies have not agreed this recommendation (Amano Y. Nihon Rinsho. Chromoendoscopic diagnosis of Barrett's esophagus. 2005 August; 63(8):1416-9). For video of chromoendoscopy in Barrett's oesophagus see Dave Project 2004 (http://daveproject.org/esophagus-chromoendoscopy-of-barretts-epithelium/2004-01-15/).

Bowel Cancer Surveillance

Neoplastic lesions in IBD may present as sporadic adenomas, adenoma-like masses (ALM), dysplasia-associated lesions or masses (DALM), low- and high grade dysplasia's or adenocarcinomas. Chromoendoscopy is the oldest method used to better define the superficial gastrointestinal mucosa. It makes use of biocompatible colorants that are topically applied to the mucosa during standard white light endoscopy through a specialized spray catheter or water irrigation system. Different stains have been used and classified into absorptive or contrast agents. Absorptive agents include methylene blue (0.1-0.5%) and cresyl violet (0.2%). They enhance the superficial structure of lesions by exploiting the different degrees of active mucosal stain uptake, thus demonstrating the various cell types. Contrast agents such as indigo carmine (0.2-0.4%) highlight the architecture via the pooling of dye in the grooves between colonic crypts and within the colonic pits and ridges of polyps.

Chromoendoscopy using methylene blue as a vital stain involves active mucosal absorption of the dye by small intestinal and colonic epithelium (Trivedi P J, Braden B, Indications, stains and techniques in chromoendoscopy. QMJ. DOI: http://dx.doi.org/10.1093/qjmed/hcs186 First published online: 24 Oct. 2012). The stain is not absorbed by non-absorptive mucosa such as squamous or gastric epithelium. Targeted biopsies should be aimed at heterogeneously stained or unstained areas, as high grade dysplasia (HGD) and early cancers absorb the dye to a lower degree due to loss in goblet cells and decreased cytoplasm.

Methylene blue chromoendoscopy requires prior mucus removal from the mucosal surface to ensure homogenous uptake of dye by epithelial cells in the upper gastrointestinal tract. This can be obtained by spraying 10% solution of N-acetylcysteine as a mucolytic onto the mucosal surface prior to the application of 0.5% methylene blue. Excess dye is carefully washed off with water until the staining pattern is stable.

With pan-colonic dye staining, segments of 20-30 cm of colon are sprayed and evaluated at a time. A slightly lower concentration (0.1%) of methylene blue is applied, using a spraying catheter onto the colonic mucosa. Excessive dye is removed by suction after a staining time of ~1 min. For video of chromoendoscopy in ulcerative colitis see (DNA-Tube).

In an international consensus statement on surveillance and management of dysplasia in inflammatory bowel disease, (Laine, L., Kaltenbach, T., Barkun, A., McQuaid, K., SCENIC international consensus statement on surveillance and management of dysplasia in inflammatory bowel disease. Gastrointestinal Endoscopy. 2015; 81(3):489), the authors discussed chromoendoscopy involving the application of dye to the colon mucosa, thereby providing contrast enhancement to improve visualization of epithelial surface detail. Methylene blue and indigo carmine were cited as the agents most commonly used, and were applied to the colon mucosa via a catheter or the colonoscope biopsy or water jet channel. pattern. Polypoid lesions were stated to be easier to detect. Once a suspicious lesion was identified, the area was selectively sprayed with a more concentrated dye (indigo carmine 0.13% or methylene blue 0.2%) directly from a 60-mL syringe through the biopsy channel. The consensus statement recommended the following doses of methylene blue: 250 ml of 0.04-0.1% MB for general inspection (water jet application), with a further 30 ml 0.2% MB if any suspicious lesions identified (syringe spray application).

Staining Abnormal Parathyroid Glands

Methylene blue stains abnormal parathyroid glands. However, false-positive staining was reported to occur in normal parathyroid glands, lymph nodes, thyroid tissue, thymic cyst and adipose tissue. Methylene blue has been shown to be efficacious, with staining rates of enlarged parathyroid glands approaching 100 percent (Patel H P, Chadwick D R, Harrison B J, Balasubramanian S P. Systematic review of intravenous methylene blue in parathyroid surgery. Br J Surg. 2012 October; 99(10):1345-51).

The mechanism of methylene blue staining by parathyroid glands is still not understood, but thiazide dyes in general (methylene blue, toluodene blue, thionine, Azur A) are taken up preferentially in certain tissues of the body and cleared at different rates. The staining does appear to be somewhat related to the size of the parathyroid gland, and both chief and oxyphil cells are readily stained, but metabolic activity or a lack of fat content or both may be factors (Orloff L A. Methylene blue and sestamibi: complementary tools for localizing parathyroids. Laryngoscope. 2001 November; 111(11 Pt 1):1901-4).

Sentinel Node Mapping

A sentinel lymph node is the first lymph node encountered by lymphatic fluid draining from a primary tumor. Intraoperative detection of the sentinel lymph node is achieved with vital dyes or lymphoscintigraphy either alone, or in combination. The methods depend on carriage of the vital dye (Patent Blue V, Isosulfan blue or Methylene blue) and/or a radioactive nanocolloid (e.g. technetium-99m in nanocolloid) in the breast and axillary lymphatics. The uptake kinetics of each mapping agent are different, but the function of both is to localize the sentinel node. It is thought that nanocolloids become entrapped within the sentinel lymph nodes either through a function of their particulate size (the larger hydrodynamic diameter of 50-100 nm for nanocolloid requires a transit time of usually more than 1 h) or because of phagocytosis by leukocytes which migrate to and are retained within the draining lymph nodes. These entrapment processes are unlikely to be mutually exclusive, and other mechanisms may also exist, but the end result is localization of the nanocolloid within the sentinel nodes rather than its diffuse spread to secondary nodes. In contrast, patent blue dyes bind to interstitial albumin and are taken up by local lymphatic tissue. The efficiency with which the lymphatics are converted to bright blue channels by the vital dyes reflects their smaller hydrodynamic diameter, their ability to disperse quickly and even their capacity to readily progress through and beyond the sentinel nodes.

Melanoma

It is known that methylene blue, possesses a high affinity for melanin, a pigment present in melanoma cells (Sobal G, Rodrigues M, Sinzinger H., Radioiodinated Methylene Blue—A Promising Agent for Melanoma Scintigraphy: Labelling, Stability and In Vitro Uptake by Melanoma Cells. ANTICANCER RESEARCH 28: 3691-3696 (2008)). Methylene blue forms a strong complex with melanin and may provide a means of selective delivery of radionuclides to melanoma cells, useful for noninvasive diagnosis as well as for therapy of disseminated disease. The fact that methylene blue is not directly toxic to the tumor and accumulates in melanoma tissue, showing a high concentration of melanin, allows tumor imaging using suitable radionuclides.

Oral Cancer

Most oral malignancies occur as squamous cell carcinomas. Many OSCCs develop from premalignant lesions & conditions of the oral cavity. The exact mechanism for the uptake of methylene blue in epithelial tissue may resemble that of toluidine blue in the acidophilic characteristic of cells with abnormal concentration of nucleic acid, resulting in differential uptake between normal/benign and highly dysplastic/malignant cells.

Periodic clinical examination of the oral cavity is the mainstay for early detection of oral cancers. It was shown to reduce mortality from oral cancer by 32% in high-risk individuals. Additionally, using adjunctive aids such as toluidine blue (also referred to as tolonium chloride) has been widely accepted to improve the effectiveness in large-scale screening for oral cancer diagnosis. However, it is hazardous if swallowed, and was shown to have toxicity to fibroblasts. Methylene blue has a similar chemical structure and exhibits similar physicochemical properties to toluidine blue but is less toxic to the human body. The sensitivity and reliability of in vivo staining with methylene blue as a diagnostic adjunct in screening for oral malignant or pre-cancerous lesions methylene blue has been evaluated and methylene blue has been shown to be a useful diagnostic adjunct in a large, community-based oral cancer screening program for high-risk individuals (Ya-Wei Chen, Jiun-Sheng Lin, Cheng-Hsien Wu, Man-Tien Lui, Shou-Yen Kao, Yao Fong. Application of In Vivo Stain of Methylene Blue as a Diagnostic Aid in the Early Detection and Screening of Oral Squamous Cell Carcinoma and Precancer Lesions. J Chin Med Assoc, 2007. 70:497-503).

Figure 12:
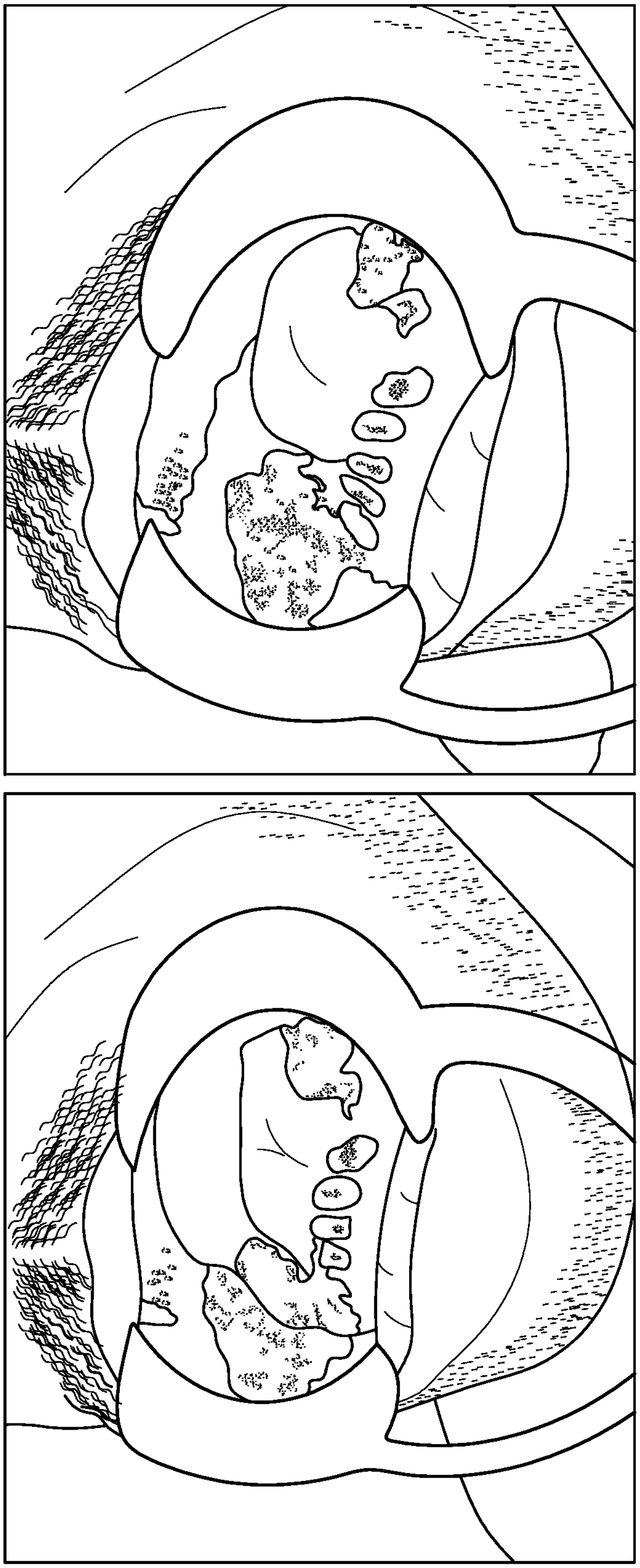
FIG. 12 illustrates staining of oral cancer with methylene blue.

For the procedure, the mucosa of the target area is gently dried with gauze and power air spray to ensure that the lesion is not being contaminated with saliva. The dye (1% methylene blue) is directly applied on the lesion with help of cotton bud first and after used as a mouth rinse. Patients gargle with 1% Methylene blue for 30 seconds; then expectorate. Patients then rinse again with 1% lactic acid for 30 seconds to wash out the excess dye. The pattern of dye retention is assessed by the intensity of stain retention on the lesion (FIG. 12) (Riaz A, Shreedhar B, Kamboj M and Natarajan S. Methylene blue as an early diagnostic marker for oral precancer and cancer. SpringerPlus 2013, 2:95 doi:10.1186/2193-1801-2-95).

Lung Cancer

There have been 3 published reports of the utility of methylene blue as a potential lung cancer diagnostic when used during bronchoscopy. The results of these were conflicting, with the 2 case series from the 1980s reporting a potential benefit and a more recent study that was unable to validate these previous results.

Chromobronchoscopy in the Diagnosis of Brochial Tumours (Ovvhinnikov A A, Dianov V V, Lukomosky G I. Chromobronchoscopy in the Diagnosis of Bronchial Tumours. Endoscopy. 1980; 12:147-150)

Protocol: Rigid bronchoscopy under general anaesthetic using a Friedel bronchoscope. The bronchial area to be stained were washed twice with 5% sodium carbonate (or physiological saline) and unspecified volume of trypsin or chymotrypsin. 2 ml of 0.2-0.4% methylene blue solution was delivered to the target area using a bronchoscopic atomiser. After 1 minute, the area was washed with physiological saline. Photographs and biopsies of the stained areas were then taken.

Results: 140 patients were included in the study. 76 patients were diagnosed with non-small cell lung cancer (NSCLC) based on biopsy results. In all 76 lung cancer patients, methylene blue was reported to selectively stain lung cancer. The stain is described as “dark blue” with “sharp contrast to the pink mucosa of unaffected areas”. Squamous cell carcinomas were described as staining more intensely than other forms of NSCLC. Benign bronchial tumours were not stained. 16/60 patients without cancer were stained by methylene blue, however this was described as “less intense as lung cancer”. These false positive results occurred in patient with infective or inflammation disease (biopsy results showed metaplastic change in 10/16 of these patients).

Vital Staining in Fibre optic Bronchoscopy (Varoli F, Mariani C, Fasceanella A, Cosentino F, Vital Staining in Fibreoptic Bronchoscopy. Endoscopy. 1986; 18:142-143.)

Protocol: Flexible bronchoscopy under awake sedation. Target area of the bronchial tree were washed with mucolytic solution (ambroxol chloride), 5% sadium carbonate and physiological saline. An unspecified volume of 0.7% methylene blue or 0.5% toluidine blue was applied to the target area using a spray catheter. After 1 minute, the target area was washed with physiological saline. Biopsies were taken from visually identified exophytic tumours, whether stained or not, as well as areas of staining in visually normal mucosa.

Results: 28 patients were included in the study. Methylene blue was utilised in 18 cases. Lung cancer was visually identified during bronchoscopy in 21 patients, and confirmed by biopsy. Selective staining of lung cancer was reported in 17/21 cases. In 6 of these patients, further areas of “minor” staining were noted in visually normal regions. Biopsy reveal squamous metaplasia (5/6 patients) and severe dysplasia. Of the 7/28 patients without exophitic tumour growth, 4 patients showed positive staining. Biopsy of these areas revealed epideroidal carcinoma (1/4) and squamous metaplasia (3/4). Staining of the areas of squamous metaplasia was described as “less intense than neoplastic areas”.

Methylene Blue-Aided In Vivo Staining of Central Airways during Flexible Bronchoscopy (Zirlik S, Hildner K M, Neurath M F, Fuchs F S. Methylene blue-aided in vivo staining of central airways during flexible bronchoscopy. Scientific World Journal. 2012; 2012:625867. doi: 10.1100/2012/625867)

Protocol: Flexible bronchoscopy under awake sedation. The tracheobronchial tree was examined using white light bronchoscopy to identify macroscopic areas of abnormal mucosa. Prior to the application of methylene blue, the airways were prepared by applying 5 ml of 5% acetylcysteine (mucolytic), 10 ml of 0.9% sodium chloride and aspirating secretions. 10 ml of 0.1% methylene blue was then applied using a spray catheter. After 1 minute, the target area was washed with physiological saline. Biopsies were taken from areas of circumscribed or remarkable dye uptake, as well as from areas identified as possibly malignant on white light bronchoscopy.

Results: 26 patients were included in this study. In all patients a weak, non-specific staining of the whole bronchial tree was noted. In 11 patients with exophytic lung cancer visible during white light bronchoscopy, no preferential methylene blue stain was reported. This study reported that significant uptake of methylene blue was only seen in 1 of 19 patients diagnosed with cancer on lung biopsy. In 1 case, normal mucosa was stained blue but the lung cancer remained unstained. No side effects of the staining procedure occurred during bronchoscopy or during a follow up of 24 hours in all patients.

Methylene Blue Vital Staining: Proposed Mechanisms of Action

Methylene blue is used as a contrast stain in several diagnostic situations. In some tissues, methylene blue stains the normal epithelium but does not stain metaplastic/cancerous cells while in other tissues, methylene blue does not stain the normal epithelium and does stain stains metaplastic/cancerous cells (Fennerty M B, Sampliner R E, McGee D L, Hixon L J, Garewal H S. Intestinal metaplasia of the stomach identification by a selective mucosal staining technique. Gastrointest Endosc 1992; 38:696-698 and Fennerty M B. Tissue staining. Gastrointest Endosc Clin North Am 1994; 4:297-311). For example, methylene blue is taken up by actively absorbing tissues such as small intestinal and colonic epithelium. It has been used to highlight subtle mucosal changes in the small intestine (e.g. celiac disease) and colon (flat adenomas and carcinomas). It does not stain non-absorptive epithelia such as squamous or gastric mucosa. Hence, it can positively stain metaplastic absorptive epithelium, such as intestinal-type metaplasia in the stomach or not stain non-absorptive epithelium, such as ectopic gastric metaplasia in a background of positive staining duodenal mucosa.

Figure 13:
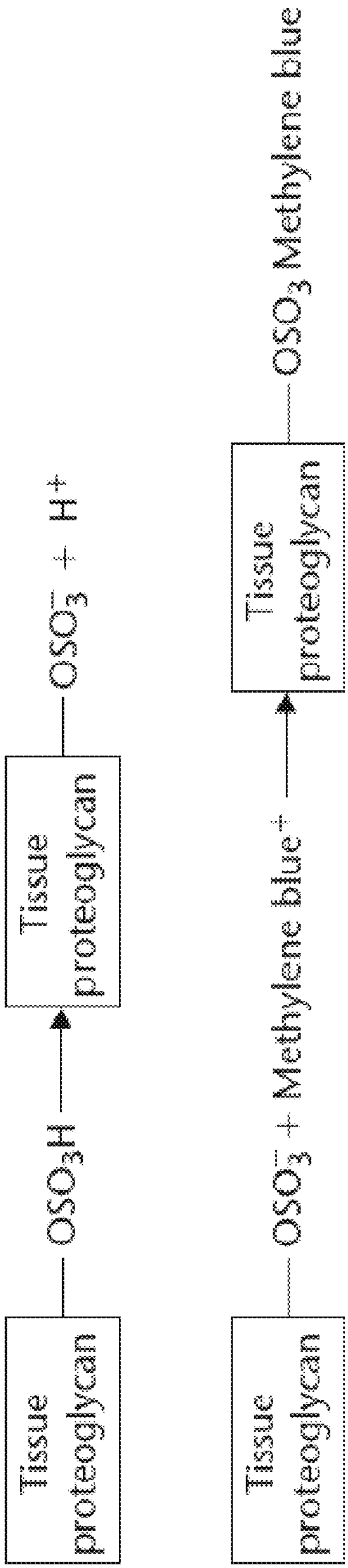
FIG. 13 illustrates ionization of sulphate groups in mucins and their subsequent binding of methylene blue.

Thus, methylene blue staining of normal epithelium is due to normal active absorbing processes in certain tissues and a contrast is apparent with metaplastic/cancerous cells, which appear unstained in comparison. In tissues that are not solely absorbing tissues, such as the oral and airway epithelia, methylene blue does not stain the normal epithelium. The mechanism by which methylene blue stains metaplastic/cancerous cells in these tissues is not fully understood. Methylene blue can enter cells when there are structural alterations in the cell membrane which may occur in cancer cells. Alternatively, the mechanism for the uptake of methylene blue in epithelial cells may resemble that of toluidine blue in the acidophilic characteristic of cells with abnormally increased concentrations of nucleic acids, resulting in differential uptake between normal/benign and highly dysplastic/malignant cells. Chen and co-workers published a study in 2006 where they assessed the use of methylene blue as a diagnostic aid in early detection of oral cancer and precancerous lesions (Chen et al. Use of methylene blue as a diagnostic aid in early detection of oral cancer and precancerous lesions. British Journal of Oral and Maxillofacial Surgery Volume 45, Issue 7, October 2007, Pages 590-591). The sensitivity was comparable with that reported using toluidine blue staining. Cationic dyes are commonly called basic dyes and so substances staining with such dyes are called basophilic. Substances that bind basic dyes include nucleic acids and acid mucins. Positively charged methylene blue ions will bind to tissue anions such as carboxylic acids, sulphuric acid and phosphoric acid groups. These groups need to be ionised to bind to the dyes (FIG. 13).

Safety

Acute Toxic Effects:

1. In humans, large doses (500 mg) administered intravenously have been reported to cause nausea, abdominal and chest pain, cyanosis, methemoglobinemia, sweating, dizziness, headache and confusion.
2. Intradermal and subdermal injections of Methylene blue can cause erythematous skin lesions, superficial ulceration and tissue necrosis.
3. 3 reported anaphylaxis reactions to methylene blue:
   2005: Intrauterine 1% methylene blue instillation
   2008: SLN mapping in breast.
   2010: SLN mapping in breast, 2 ml subdermal methylene blue Safety Data:

1. Safer than Isosulfan (Lympazurin)
   Bezu C et al., Surg Oncology, 2011.
   In SLN mapping for gastrointestinal tumours. Soni M et al., Ann Surg Oncol, 2009.
2. Expected to be safe for use in pregnancy, minimal fetal risk
   Pruthi S et al., Amer J Surg, 2011.
3. methylene blue is safe for use in children to distinguish between preauricular sinuses (PASs) and branchial sinuses and fistulae (BSF).
   Dickson J M et al., J Otolaryngol Head Neck Surg, 2009.

Adverse Device Effects

Techniques for early diagnosis of diseases such as lung cancer are urgently required. Lung cancer remains the largest cause of cancer deaths worldwide. Lung cancer is accountable for the highest number of cancer deaths worldwide, despite advances in chemotherapy over recent years. The most effective method to substantially improve survival figures would be diagnosing lung cancer at an earlier stage, when therapy may be more effective. The current electrospray platform may allow for a novel diagnostic test that would improve the accuracy of invasive tests (bronchial bisopsies).

The standard risks associated with bronchoscopy are rare and include excessive bleeding from a biopsy site, low oxygen levels due to the sedation and heart arrhythmias. Very occasionally a patient may complain of a sore throat or a fever after the procedure.

The risks of the use of small volumes of topical methylene blue to the lungs is felt unlikely to impart any significant side effects, and this has already been applied to the lung at a dose of an unspecified volume of 0.7% methylene blue using a spray catheter over a period of 1 minute without adverse events reported (Zirlik S, Hildner K M, Neurath M F, Fuchs F S. Methylene blue-aided in vivo staining of central airways during flexible bronchoscopy. Scientific World Journal. 2012; 2012:625867. doi:10.1100/2012/625867). In addition, intravenous administration of methylene blue is routinely used in the treatment of methemoglobinaeimia and as a visual aid in parathyroid surgery.

In regards to the risk of bronchoscopic electrospray, this is a novel procedure that has not as yet been performed in man. As such the adverse events are unknown. The platform is a low energy system that is not thought to be associated with risk to the patient. However, to atomise the methylene blue an electrical current is applied to solution. The potential risks associated with this include device failure, electric shocks, burning to lung tissue and cardiac arrhythmias.

The use of small volumes of topical methylene blue delivered in this study are unlikely to impart any significant side effects, the reported side effects of the use intravenous of methylene blue include the following:

- The most commonly reported adverse reactions are nausea, abdominal and chest pain, headache, dizziness, tremors, anxiety, confusional state, dyspnoea, tachycardia, hypertension, the formation of methaemoglobinaemia and hyperhidrosis.
- It may impart a blue-green color to urine and a blue color to skin
- Repeated doses of methylthionium chloride may exacerbate Heinz body formation and haemolytic anaemia (Total cumulative dose should not exceed 4 mg/kg)
- Methylthionium chloride should be avoided in patients receiving medicinal products that enhance serotonergic transmission including SSRIs (selective serotonin reuptake inhibitors), bupropion, buspirone, clomipramine, mirtazipine and venlafaxine.

Example Implementation of Electrospray-Mediated Transfer of Nucleic Acids to Ex Vivo Porcine Lung While nucleic acid-based therapies have the potential to provide clinically meaningful benefit across a wide spectrum of lung disease in vivo delivery remains a challenge. Electrospray atomisation is a method of generating fine droplets of a solution. Here we examined the feasibility of using electrospray to deliver nucleic acids to explanted porcine lung tissue and whole lungs. Reporter plasmid DNA and mRNA, expressing green fluorescent protein and luciferase, and FITC-labelled siRNA were delivered in 20% ethanol solution via electrospray to explants of tracheal tissue cultured at air-liquid interface. Increased fluorescence was evident in explants following delivery of pEGFP, GFP mRNA and siRNA-FITC compared to controls. Luciferase levels in explant culture supernatants following electrospray transfection of pGLuc ($p<0.005$) and luciferase mRNA ($p<0.05$) were significantly increased compared to controls. Solutions of luciferase mRNA and siRNA-FITC were also delivered to a porcine ex vivo whole lung model via bronchoscopy using an electrospray catheter. Successful bronchoscopic electrospray delivery of luciferase mRNA ($p<0.005$) and siRNA-FITC was observed. In summary, we report the successful ex vivo delivery of nucleic acids to explanted porcine lung tissue via electrospray. In addition, we describe bronchoscopic electrospray delivery of nucleic acid to ex vivo porcine whole lung.

Nucleic acid-based therapies have the potential to provide clinically meaningful benefit across a wide spectrum of lung disease. However, challenges in achieving effective delivery have limited the success of this therapy to date. While viral vectors have been intensively examined for lung gene therapy, the airway mucus gel layer remains a significant barrier to inhaled viral and non-viral vectors[1]. Non-viral methods of gene delivery, including chemical and physical methods of gene delivery, have benefits over viral delivery as they are less immunogenic, less restricted in the size of DNA they can deliver and have fewer regulatory hurdles for in vivo use. However, the absence of a successful commercial therapy involving non-viral vectors indicates that further challenges remain with these approaches.

In addition to delivery of traditional drugs, aerosolisation has long been viewed as a desirable route for gene delivery to the lungs. Aerosolization of a solution can be achieved by several methods. The most common method employs a spray nozzle through which fluid passes and is acted upon by mechanical forces that atomize the liquid. For delivery to the lung, sonication is widely used whereby high frequent vibration through a nebulizer nozzle plate produce small droplets of a liquid. However, current aerosol delivery methods such as jet or ultrasonic nebulisers can cause shear stress to the DNA resulting in a poor efficiency of gene delivery[2], a significant drawback of devices and methods prior to the present invention overcomes the drawbacks of earlier methods and devices. Electrospray, also known as electrostatic spray, is an alternative method of atomizing a liquid. In order to generate an electrospray, a high voltage is applied to a solution as it passes through a conducting emitter such as a needle[3]. The potential difference generated between the charged solution and a ground electrode generates an electric field drawing the liquid towards the ground electrode. The meniscus forms a characteristic cone, known as a 'Taylor' cone and when the voltage threshold overcomes the surface tension of the solution, the tip of the Taylor cone dissociates, or atomizes, into droplets forming either a jet, a plume or a combination spray of charged microdroplets. With other methods of spray generation the droplets fall by gravity onto a surface but with electrospray, within a certain distance, the droplets accelerate towards a surface[4]. In addition, because the droplets are charged, an electrospray is more controllable than other forms of spray, yet another advantage over earlier attempts. Unlike previous attempts, transfection of delivered molecules and function of those molecules in pulmonary cells was demonstrated at air-liquid interface using the device and methods described herein.

DNA, mRNA and siRNA via electrospray were delivered to lung tissue at a clinically-relevant air-exposed interface, e.g., to porcine tracheal explants cultured at an air-liquid interface. Then, we assessed the feasibility of electrospray atomisation for the delivery of nucleic acids directly to the lung, via bronchoscopy, in a porcine model.

Materials and Methods

Materials: Plasmids: pEGFP (Clontech Laboratories, Mountainview, Calif., USA) and pGLuc (New England Biolabs, Ipswich, Mass., USA). GFP mRNA and luciferase mRNA (TriLink Biotechnologies, San Diego, Calif., USA). BLOCK-iT™ Fluorescent Oligo (siRNA-FITC) (Thermo Fischer Scientific, Waltham, Mass., USA).

Electrospray Delivery

Figure 19:
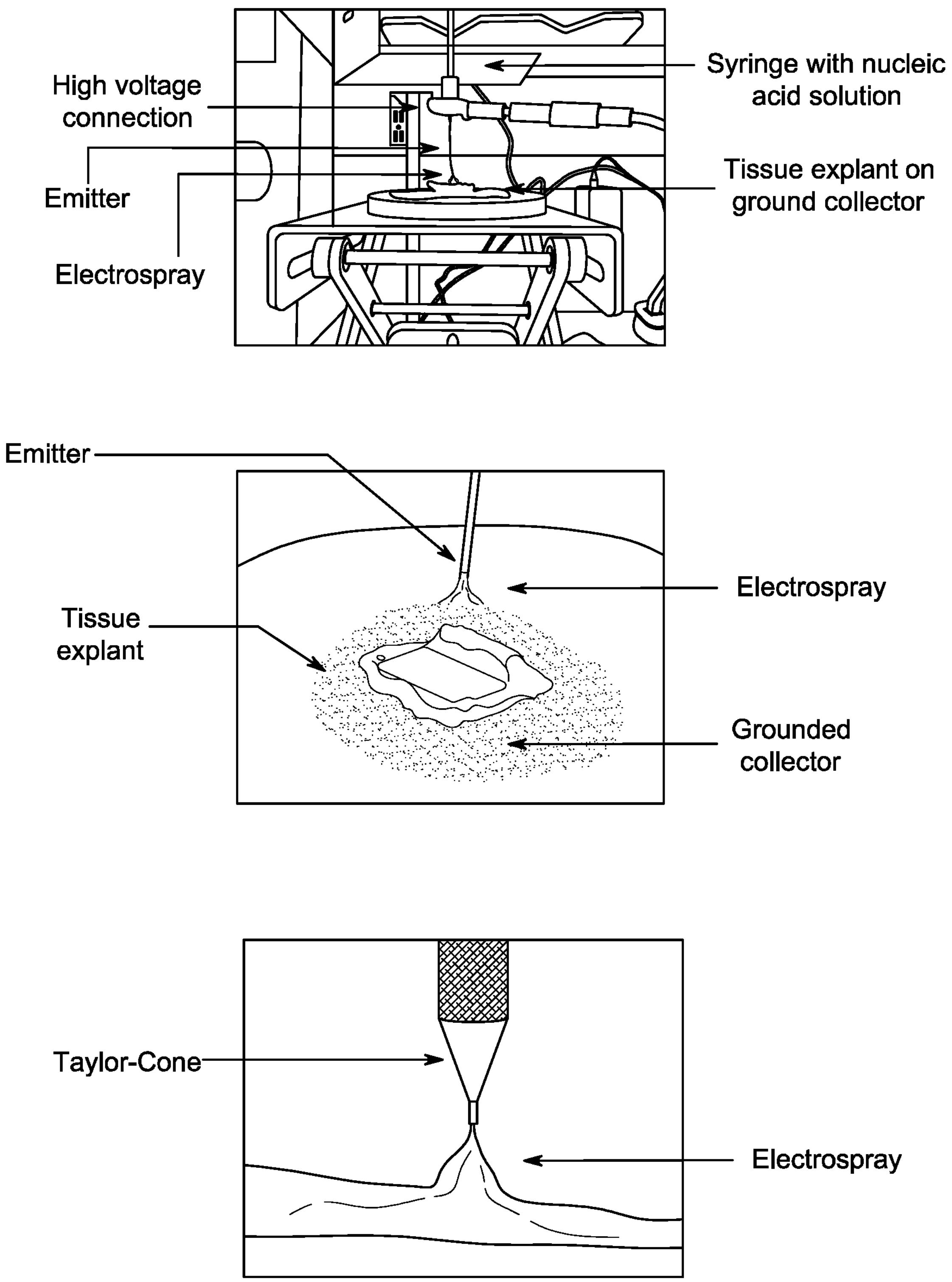
FIG. 19 illustrates an apparatus used for the electrospray delivery of nucleic acids to porcine lung tissue segments ex vivo. (a) Electrospray apparatus. (b) Electrospray plume, visualized with a laser, during delivery to tissue. (c) Magnified image of Taylor cone and electrospray plume.

The Spraybase Generation 1 electrospray instrument with a 30G Hamilton needle was used (Avectas Ltd., Maynooth, Ireland) (FIG. 19). The emitter, a, was positioned above a grounded base plate, 15 mm from the epithelial surface of the tissue. Voltage was adjusted to achieve a stable Taylor cone and diffuse plume (FIGS. 19*b* and 19*c*). The voltage required to achieve this ranged from 3-5 kV depending on environmental conditions (humidity/temperature), flow rate and concentration of solution. Nucleic acids were re-suspended in delivery solution which was water containing 20% ethanol. Porcine explants were placed epithelial surface up, in the center of the base plate, below the electrospray emitter and nucleic acid solutions were delivered over 2-3 minutes, at a flow rate appropriate for the solution. For experiments involving plasmid DNA, the total treatment (15 μg) was delivered in three divided doses, on three consecutive days. In all other experiments the total treatment was administered with a single spray. Following nucleic acid delivery, the tissue segments were placed on agarose plugs in fresh culture medium.

Bronchoscopic Electrospray Delivery of Nucleic Acids to Porcine Lung Ex Vivo

The electrospray catheter system was composed of an electrospray catheter, power pack and a syringe pump (Avectas Ltd.) (FIG. 20). The porcine heart-lung block was prepared by cannulating the superior vena cava and perfusing culture medium supplemented with 7% albumin and 0.5% dextran through the pulmonary vasculature with a peristaltic pump (Masterflex, Gelsenkirchen, Germany). The trachea was intubated and ventilated (IPAP 14; EPAP 4; FiO2 21%) using a NIPPY 2 ventilator (RespiCare Ltd., Swords, Ireland). The lungs were cleared of debris by instilling 10 ml aliquots of 0.9% saline and suctioning. Prior to bronchoscopic electrospray delivery, a target endobronchial area was selected and marked with 3 dots to form a target using SPOT endoscopic marker (GI Supply, Camp Hill, Pa., USA).

Analysis of Nucleic Acid Expression

Fluorescence was analysed using the Olympus CKX41 microscope (Optika Vision Pro) and fluorescence module (CoolLED pE-300white). Some GFP mRNA and siRNA-FITC electrosprayed tissues and controls were frozen in OCT (Sigma-Aldrich) and cryosectioned prior to viewing by fluorescence microscopy. For pGLuc and luciferase mRNA expression, following appropriate incubation periods, supernatant was analysed using the Biolux™ Gaussia Luciferase Assay (New England Biolabs) according to manufacturer's instructions.

Statistics

Two-tailed, unpaired T-Tests were used for statistical analysis using Graphpad Prism version 7.03 for Windows (GraphPad Software, La Jolla, Calif., USA).

Results

Delivery of Plasmid DNA to Lung Explant Tissue

Figure 15:
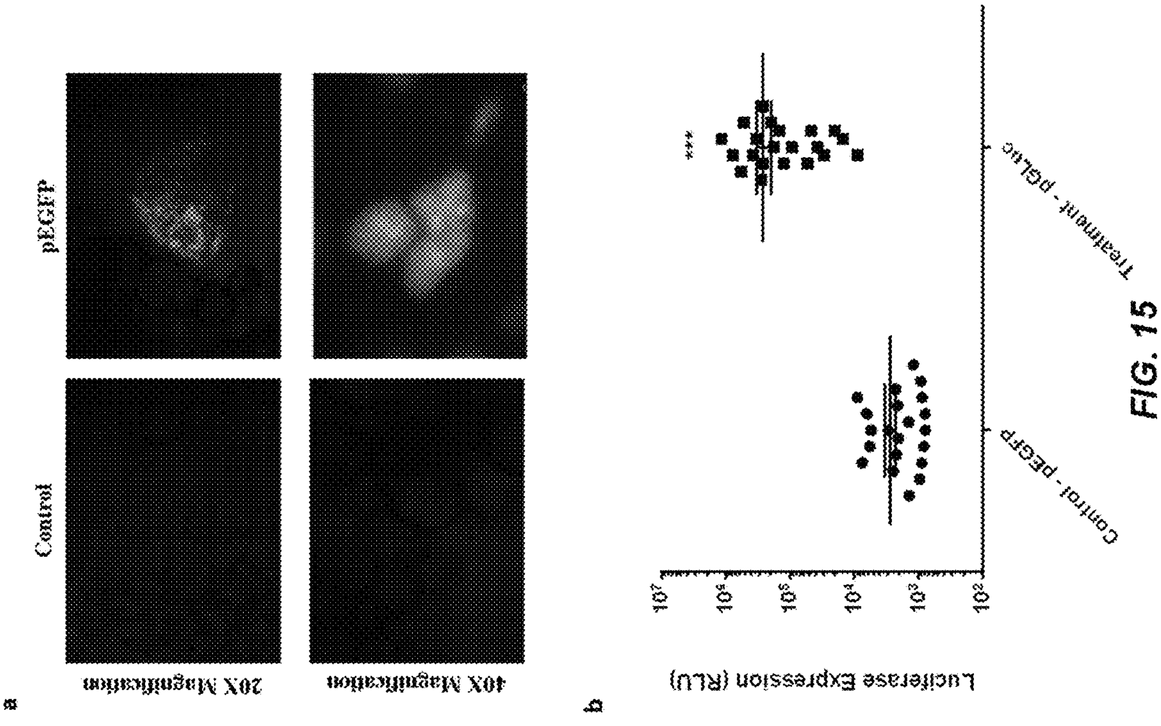
FIG. 15 illustrates electrospray delivery of plasmid DNA to explanted porcine lung tissue. (a) Representative images of green fluorescent protein (GFP) expression following pEGFP transfection compared to negative control (pGLuc). (b) Quantification of Gaussia luciferase expression following pGLuc transfection compared to negative control (pEGFP). n=21. *** $p<0.001$.

Porcine tracheal explants were electrosprayed with 5000 ng of pEGFP plasmid DNA (833 ng/μl; flow rate 3 μl/min; duration 2 min) on day 1, 2 and 3 and then cultured for a further 48 hr. pGLuc, which encodes for luciferase, was delivered as a negative control for green fluorescent protein (GFP) fluorescence. The epithelial and submucosal sections were then dissected from the trachea and underlying connective tissue. Sections were mounted on slides and visualized by fluorescence microscopy. GFP expression was evident in the tissue sections of peGFP-treated tissue but not in the pGLuc negative control (FIG. 15*a*).

It was noted that high levels of endogenous auto-fluorescence present in lung tissue can impede visualization of fluorescent reporters. Therefore, pGLuc was used to further validate and quantify DNA expression after electrospray delivery. 5000 ng pGLuc was electrosprayed onto tracheal tissue sections (833 ng/μl; flow rate 3 μl/min; duration 2 min) for 3 consecutive days and tissues were then cultured for a further 48 hours. peGFP was delivered as a negative control. 20 μl of culture media was sampled from each well and luciferase expression was quantified. There was a significant increase of luciferase expression (p=0.0002) in the media of pGLuc electrosprayed tissue compared to the media of pEGFP electrosprayed controls (FIG. 15*b*).

Delivery of mRNA to Lung Explant Tissue

Figure 16:
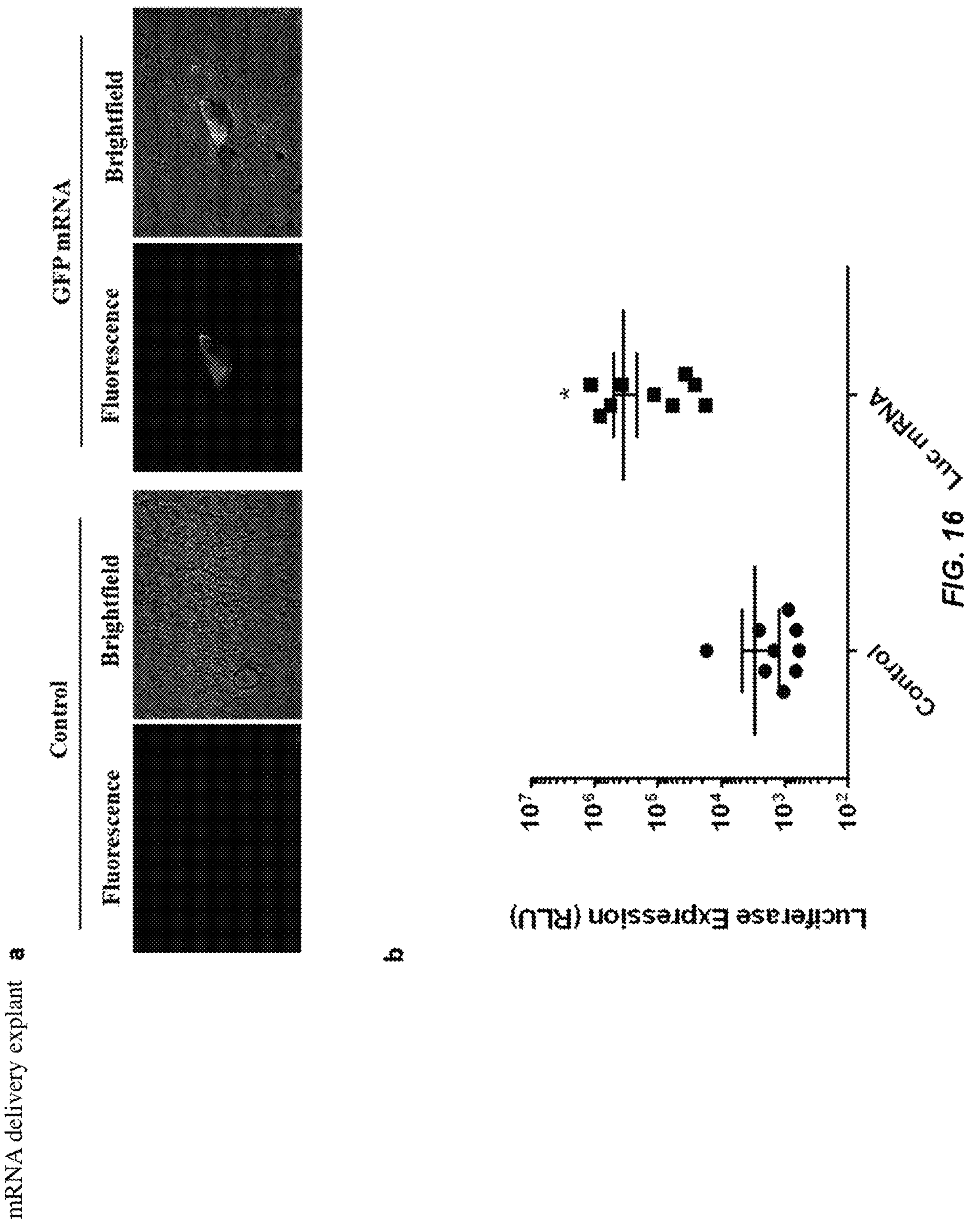
FIG. 16 illustrates electrospray delivery of mRNA to explanted porcine lung tissue. (a) Representative images of green fluorescent protein (GFP) expression following GFP mRNA transfection compared to buffer-only control are shown. Fluorescence image is shown as well as corresponding brightfield image with superimposed fluorescence image, 10× magnification. (b) Quantification of luciferase expression following luciferase mRNA transfection, compared to buffer-only control. n=9. * $p<0.05$.

We next examined the delivery of mRNA encoding for GFP and luciferase. 2.4 μg GFP mRNA was electrosprayed onto tracheal explants (400 ng/μl; flow rate 3 μl/min; duration 2 min) and cultured for 24 hr. Buffer without mRNA was electrosprayed as a negative control. GFP expression was evident in the dissected epithelial layer of the tracheal tissue when examined by fluorescence microscopy (FIG. 16*a*). 10 μg luciferase mRNA was electrosprayed onto the trachea explants (700 ng/μl; flow rate 4.8 μl/min; duration 3 min) and incubated for 48 hours. Again buffer without mRNA was electrosprayed as a negative control. Quantification of luciferase expression showed a significant increase in luminescence expression (p=0.023) in the mRNA electrosprayed samples compared to control explants (FIG. 16*b*).

Delivery of siRNA to Lung Explant Tissue

Figure 17:
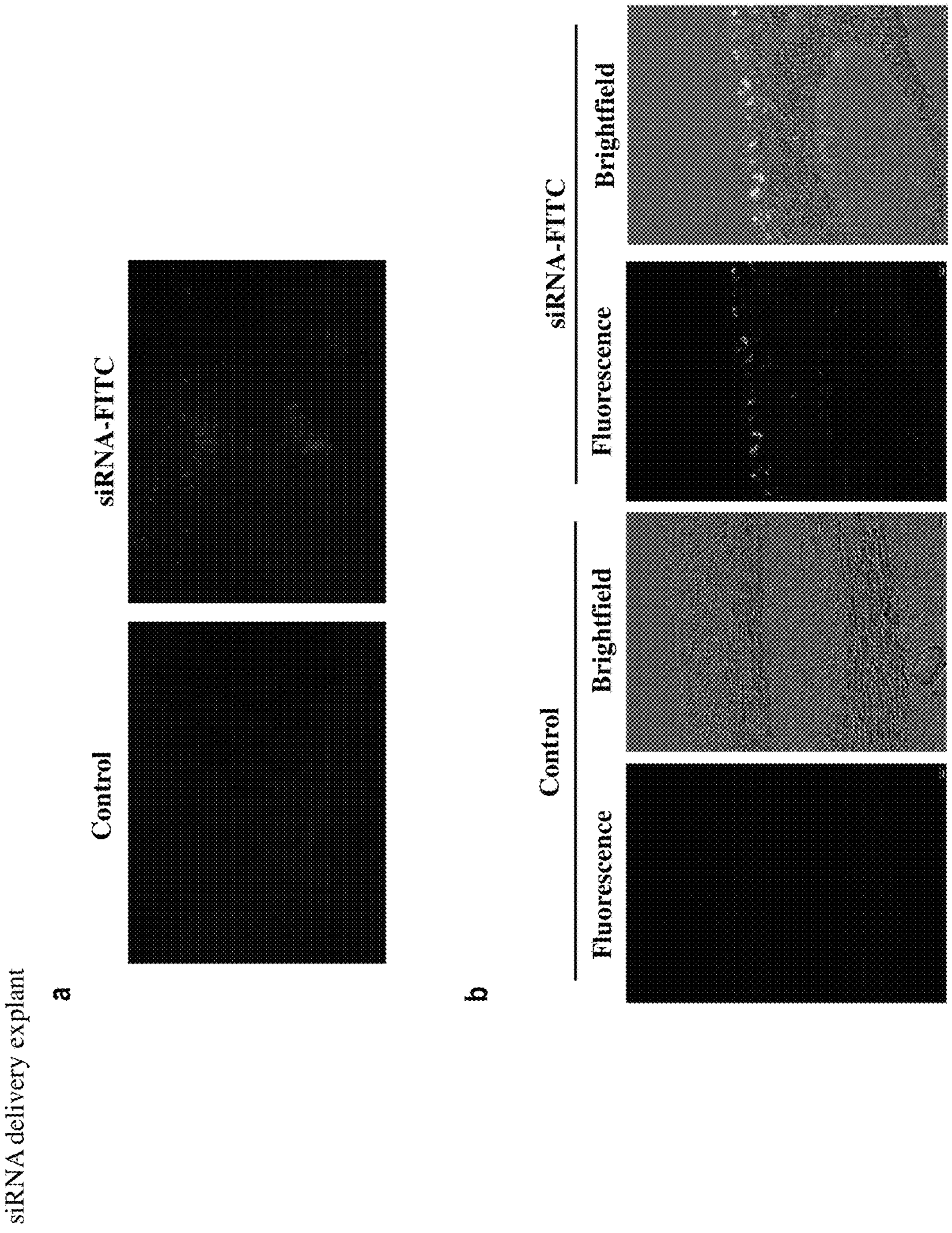
FIG. 17 illustrates electrospray delivery of siRNA to explanted porcine lung tissue. Representative fluorescence microscopy images of FITC (model for delivery molecule) localisation following siRNA-FITC delivery compared to buffer-only control are shown. Visualisation following (a) microdissection (b) cryo-sectioning where fluorescence image is shown as well as corresponding brightfield image with superimposed fluorescence image, 20× magnification.

We were also interested in the ability of electrospray to achieve delivery of siRNA molecules. 20 μl 100 μM siRNA-FITC was delivered to the trachea explant (100 uM; flow rate 10 ul/min; duration 2 min) and compared to a buffer-only negative control. Following delivery, the epithelial layer was microdissected and examined under a fluorescent microscope. FITC fluorescence was evident in tissues that were electrosprayed with siRNA but not in control tissues (FIG. 17*a*). In addition, tracheal segments were cryosectioned in the transverse plane, allowing visualisation of siRNA within the tissue (FIG. 17*b*).

Bronchoscopic Delivery of mRNA and siRNA to Porcine Lung Ex Vivo

Figure 18:
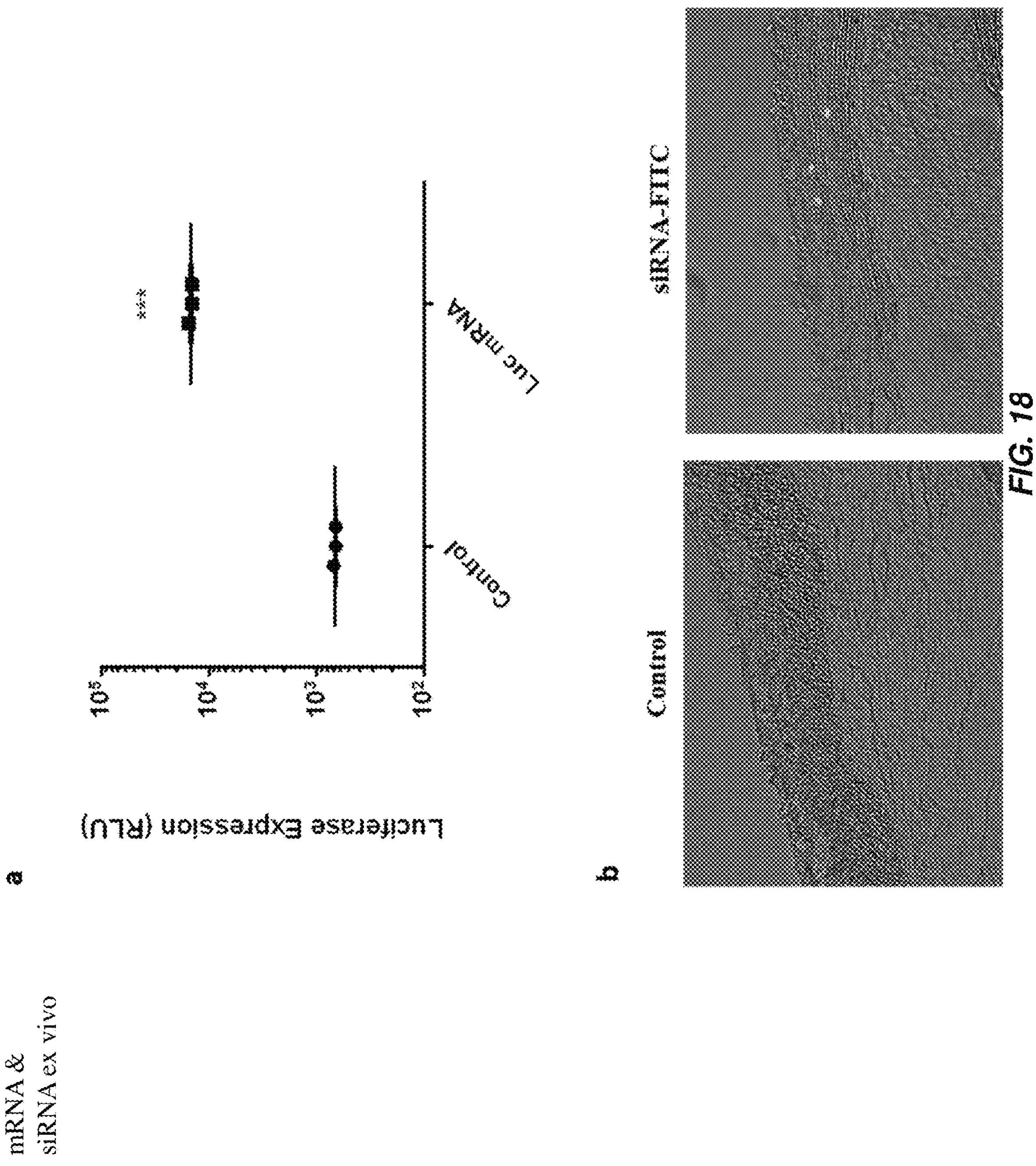
FIG. 18 illustrates bronchoscopic electrospray delivery of mRNA and siRNA delivery to porcine lungs ex vivo. (a) Quantification of luciferase expression following luciferase mRNA transfection, compared to buffer-only control. n=3. *** $P<0.001$. (b) Representative fluorescence microscopy images of FITC localisation following siRNA-FITC delivery compared to buffer-only control. Fluorescence image is shown as well as corresponding brightfield image with superimposed fluorescence image, 20× magnification.

Having demonstrated successful delivery of nucleic acids to explanted lung tissue, we next examined whether we could achieve electrospray-mediated delivery into a whole lung using a bronchoscope and an electrospray catheter. Prior to bronchoscopic electrospray delivery, a target endobronchial area was selected and marked with 3 dots to form a target using SPOT endoscopic marker. The electrospray catheter was then inserted into the working port of a bronchoscope, positioned 15 mm from the pre-marked target and nucleic acid was delivered to the center of the dots. Six 20 μl aliquots of siRNA-FITC (3.3 μM solution; flow rate 100 μl/sec; duration 0.2 sec per aliquot) and 10 μl (3 μg) of mRNA-GLuc (300 ng/μl; flow rate 100 μl/sec; duration 0.1 sec) were delivered to target areas. These were then resected, washed as above and cultured at air liquid interface. Luciferase mRNA expression was measured at 48 hr post-delivery and siRNA-FITC was viewed at 24 hrs post-delivery. A significant ($p<0.0001$) increase in luciferase expression was detected in luciferase mRNA-treated samples compared to buffer-only controls and visible fluorescence following siRNA-FITC delivery was apparent (FIG. 18).

Porcine Tracheal Explant Culture

Pig lungs were obtained from a local abattoir. Cold ischemic time was limited to 90 min. The trachea was dissected into sections approximately 20×50 mm, rinsed with phosphate-buffered saline (PBS) and 3-4 wash cycles in 1:1 RPMI 1640:DMEM, 200 units/ml penicillin, 200 ug/ml streptomycin, 2.5 ug/ml amphotericin, 50 ug/ml gentamicin (all Sigma-Aldrich, St. Louis, Mo., USA) were performed.

Each wash cycle included changing wash media, 10 minutes of agitation on a cell shaker and 1 hr incubation at 37° C., 5% $CO_2$. Tracheas were cut into 10 $mm^2$ segments, including epithelium, mucosa and cartilage. Tissue segments, epithelial layer facing upwards, were placed onto 5 mm high sterile agarose (1% w/v) plugs in 12-well plates. Culture media (wash media plus 10 mM L-glutamine and 10% FBS (Sigma-Aldrich)) was added so that the basal section of the tissue section was submerged. Explants were incubated overnight at 37° C., 5% $CO_2$, in a humidified atmosphere.

Nucleic Acid-Based Therapies Using Electrospray Catheters

Nucleic acid based therapies have significant disease modifying potential. As such, there has been much interest in developing techniques that successfully deliver these molecules in vivo. The data described herein was generated using art-recognized models for human clinical or veterinary clinical therapeutic administration modalities. Multiple viral and non-viral vectors have been utilized for this aim, but success has been limited to date. Challenges of cytotoxicity, immunogenicity and transfection inefficiency have hampered progress. Improved safety profiles with non-viral vectors have increased interest in these techniques. However, technologies to improve transfection efficacy are needed if non-viral vector therapies are to have a clinically meaningful effect. In this study, we have shown that vector-free delivery of nucleic acids to tissue using electrospray is not only feasible but efficiently delivered, thereby reducing cost. Moreover the delivered molecules are functional, and the mode of delivery is minimally invasive to the subject being treated. Furthermore, using the electrospray catheter described herein, a technique was developed that allows for luminal delivery, e.g., bronchoscopic lung delivery, demonstrating the efficacy of this technology in the clinic.

This study reports the successful electrospray delivery of RNA, DNA, proteins or other molecules to tissue. Porcine lung was selected as a target for gene delivery in view of its extensive use in translational research and its close approximation of the human lung for bronchoscopic intervention[7,8]. Furthermore, the epithelial surface of the lung provides an accessible target for non-invasive (inhalation) and semi-invasive (bronchoscopy) drug delivery. Electrospray atomisation has the potential to be utilized as a drug delivery platform for both modalities.

The process of electrospray atomisation involves the generation of an electric field between a charged solution and a grounded collector. As the electromagnetic field overcomes surface tension, the solution is dispersed into nano-sized particles that move towards a collector at high velocity. The characteristics of electrospray generated particles—size, charge, velocity and direction—facilitates drug delivery by addressing factors that reduce the efficiency of nucleic acid delivery to tissue. Electrospray creates conditions in which particles pass through a cell membrane by kinetic force. This effect may also be achieved by the interaction of charged particles with membrane-bound voltage gates or ion channels. In addition, the electric field associated with an electrospray may induce the transient formation of pores within the cell membrane, known as electroporation.

Electrospray ionisation is a vector-free delivery system that has the potential to overcome multiple barriers associated with inefficient transfection. This technique has previously been reported to successfully transfect plasmid DNA in vitro.[12,13] Here we report the successful electrospray delivery of nucleic acids, e.g., plasmid DNA, mRNA and siRNA molecules. Protein expression following transfection was identified, indicating that biological integrity of nucleic acid solutions are maintained during the electrospray process.

Delivery of plasmid DNA to tissue can be challenging because the large size of these molecules can negatively impact upon cellular uptake. In addition, cellular uptake of DNA does not guarantee protein expression as nucleolar relocation must occur before protein encoding can commence. Delivery of smaller molecules, such as mRNA, increases the efficacy of protein expression by removing barriers associated with molecular size and ribosomal transcription. mRNA may also have therapeutic advantages over DNA, where factors such as transient protein expression may be an important consideration in drug development. A 2 Log increase in luciferase expression was seen with both plasmid DNA and mRNA compared to controls.

Gene regulation, and therefore disease modulation, by siRNA molecules also have great potential for treating conditions such as cancer.[14] We have shown that fluorescent labelled siRNA molecules were be delivered to the epithelial and mucosal layers of lung tissue by electrospray. Delivery of siRNA function is useful to downregulate disease pathways such as infection, inflammation or oncogenesis.

REFERENCES

1. Duncan G A, Jung J, Hanes J, Suk J S. The Mucus Barrier to Inhaled Gene Therapy. Mol Ther. 2016. 24(12):2043-2053.
2. Gomes Dos Reis L, Svolos M, Hartwig B, Windhab N, Young P M, Traini D. Inhaled gene delivery: a formulation and delivery approach. Expert Opin Drug Deliv. 2017. 14(3):319-330.
3. Jaworek A., Sobczyk A. T. Electrospraying route to nanotechnology: An overview. Journal of Electrostatics. 2008. 66:197-219.
4. Rosell-Llompart, J. & Fernández de la Mora, J. Generation of monodisperse droplets 0.3 to 4 mm in diameter from electrified cone-jets of highly conducting and viscous liquids, J. Aerosol Sci., 1994. 25, 1093-1119.
5. Okubo Y., Ikemoto K., Koike K., Tsutsui C., Sakata I., Takei O., Adachi A., Sakai T. DNA Introduction into Living Cells by Water Droplet Impact with an Electrospray Process. Angew. Chem. Int. Ed. 2008, 47, 1429-1431.
6. Zeles-Hahn M G., Lentz Y K., Anchordoquy T J., Lengsfeld C S. Effect of electrostatic spray on human pulmonary epithelial cells. Journal of Electrostatics. 2011. 69:67-77.
7. Rogers C S, Abraham W M, Brogden K a, et al. The porcine lung as a potential model for cystic fibrosis. *Am J Physiol Lung Cell Mol Physiol* 2008; 295: L240-63.
8. Judge E P, Hughes J M L, Egan J J, Maguire M, Molloy E L, O'Dea S. Anatomy and bronchoscopy of the porcine lung: A model for translational respiratory medicine. Am. J. Respir. Cell Mol. Biol. 2014; 51: 334-43
9. Zhang D, Das D B, Rielly C D. Potential of microneedle-assisted micro-particle delivery by gene guns: a review. *Drug Deliv* 2013; 7544: 571-87.
10. Lambricht L, Lopes A, Kos S, Sersa G, Préat V, Vandermeulen G. Clinical potential of electroporation for gene therapy and DNA vaccine delivery. *Expert Opin Drug Deliv* 2015; 5247: 295-310.
12. Ikemoto K, Sakata I, Sakai T. Collision of millimeter droplets induces DNA and protein transfection into cells. *Sci Rep* 2012; 2: 1-5.
13. Lee Y H, Wu B, Zhuang W Q, Chen D R, Tang Y J. Nanoparticles facilitate gene delivery to microorganisms via an electrospray process. *J Microbiol Methods* 2011; 84: 228-33.
14. Golan T, Khvalevsky E Z, Hubert A, et al. RNAi therapy targeting KRAS in combination with chemotherapy for locally advanced pancreatic cancer patients. *Oncotarget* 2015; 6: 24560-70.
15. Zamora M R, Budev M, Rolfe M, et al. RNA interference therapy in lung transplant patients infected with respiratory syncytial virus. *Am J Respir Crit Care Med* 2011; 183: 531-8.
16. Lomas-Neira J L, Chung C-S, Wesche D E, Perl M, Ayala A. In vivo gene silencing (with siRNA) of pulmonary expression of MIP-2 versus K C results in divergent effects on hemorrhage-induced, neutrophil-mediated septic acute lung injury. *J Leukoc Biol* 2005; 77: 846-53.
17. Davis M E, Zuckerman J E, Choi C H J, et al. Evidence of RNAi in humans from systemically administered siRNA via targeted nanoparticles. *Nature* 2010; 464: 1067-70.
18. Griesenbach U, Vicente C C, Roberts M J, et al. Secreted Gaussia luciferase as a sensitive reporter gene for in vivo and ex vivo studies of airway gene transfer. *Biomaterials* 2011; 32: 2614-24.

Example Implementation of Electrospray-Delivery of Nucleic Acids to Ex Vivo Porcine Airways Using Electrospray Nucleic acid-based therapies have the potential to provide clinically meaningful benefit across a wide spectrum of lung disease. However, in vivo delivery remains a challenge. Here we examined the feasibility of using electrospray to deliver nucleic acids to both porcine tracheal tissue sections and whole lung ex vivo.

The effect of electrospray solution, emitter gauge, flow rate and voltage on plasmid DNA integrity was examined by analysing supercoiled:open circle structure ratio by gel electrophoresis. Optimal parameters were used to deliver luciferase DNA and mRNA and siRNA-FITC to tracheal tissue sections. Luciferase mRNA was delivered to whole porcine lungs ex vivo using a catheter and bronchoscope system. Luciferase activity and fluorescence were analysed by luminometry and microscopy respectively.

The incidence of DNA plasmid nicking was greatest in a low salt solution without ethanol compared with 1% and 20% ethanol with salt. From a range of emitters tested, a 32 gauge emitter produced the best supercoiled:open circle structure ratio, likely because less voltage was required to produce a stable electrospray with this emitter. Lower flow rates also showed a trend towards reduced DNA nicking. GFP DNA electrosprayed at 5 kV and 6 kV resulted in lower levels of GFP expression in A549 lung cells following lipofection compared with 3 kV and 4 kV. Optimised parameters of 20% ethanol solution, 32 gauge emitter, low flow rates and voltages of 3-5 kV, nucleic acid molecules were successful for delivery of luciferase DNA and mRNA as well as siRNA-FITC to porcine tracheal tissue sections and for delivery of luciferase mRNA to whole porcine lungs via bronchoscope. In summary, we report ex vivo delivery of nucleic acids to porcine lung tissue via electrospray and bronchoscopic electrospray delivery of nucleic acid to an ex vivo porcine lung model.

Nucleic acid-based therapies have the potential to provide clinically meaningful benefit across a wide spectrum of lung disease. However, despite decades of investigation of viral and non-viral methods of nucleic acid delivery to the lungs, no treatments have yet been approved for clinical use. Issues with adverse effects and efficiency of delivery have hampered progress and the airway mucus gel layer remains a significant barrier to both viral and non-viral vectors (Duncan G A, Jung J, Hanes J, Suk J S. The Mucus Barrier to Inhaled Gene Therapy. *Mol Ther* 2016; 24: 2043-2053). In addition to long-standing gene therapy strategies where a gene is delivered to replace a defective gene or provide a therapeutic effect, emerging techniques such as gene editing hold promise as new treatment approaches. For these techniques it may be necessary to deliver mRNA, short DNA sequences and/or proteins. Therefore, new delivery strategies are needed to address challenges seen with traditional gene delivery approaches and to ensure that progress with new techniques can be translated to the lungs.

Non-viral methods of gene delivery, including chemical and physical methods, have benefits as they are less immunogenic than viral technologies and have fewer regulatory hurdles for in vivo use. However, the absence of a successful benchmark therapy involving non-viral vectors indicates that further challenges remain for these applications. Aerosolization has long been viewed as a desirable route for gene delivery to the lungs and can be achieved by several methods. The most common method employs a spray nozzle through which fluid passes and is acted upon by mechanical forces that atomize the liquid. For delivery to the lung, sonication is widely used whereby high frequent vibration through a nebulizer nozzle plate produce small droplets of a liquid. However, because drugs are inspired, this is a high amount of drug lost and poor targeting of delivery. Furthermore, current aerosol delivery methods such as jet or ultrasonic nebulisers can cause shear stress to the DNA resulting in a poor efficiency of gene delivery (Gomes dos Reis L, Svolos M, Hartwig B, Windhab N, Young P M, Traini D. Inhaled gene delivery: a formulation and delivery approach. *Expert Opin Drug Deliv* 2017; 14: 319-330.1). The ability to deliver nucleic acid-based drugs in a non-viral, targeted manner to the airways in a way that preserves activity of the molecules is therefore desirable.

Electrospray, also known as electrostatic spray, is an alternative method of atomizing a liquid that is well-established in many fields including soft ionisation mass spectrometry. An electrospray occurs when tiny quantities of electrical charge are applied to a fluid as it passes through a conducting emitter such as a needle (Jaworek A, Sobczyk A T. Electrospraying route to nanotechnology: An overview. *J Electrostat* 2008; 66: 197-219). The potential difference generated between the charged solution and a ground electrode generates an electric field drawing the liquid towards the ground electrode. The meniscus generated forms a characteristic cone, known as a 'Taylor' cone. When the voltage threshold overcomes the surface tension of the solution, the tip of the Taylor cone dissociates, or atomizes, into droplets forming either a jet, or a plume of charged microdroplets. While other methods of spray generation utilise gravity and droplets decelerate once formed, within a certain distance, the electrospray droplets accelerate towards a surface (Rosell-Llompart J, Fernández de la Mora J. Generation of monodisperse droplets 0.3 to 4 μm in diameter from electrified cone jets of highly conducting and viscous liquids. *J Aerosol Sci* 1994; 25: 1093-1119). In addition, because the droplets are charged, an electrospray is more controllable than other forms of spray and therefore lends itself to targeted delivery. These features have led some investigators to examine electrospray as a method for gene delivery although reports are few and inconsistent, possibly due to significant differences between electrospray configurations, solutions and parameters. While successful delivery of plasmid DNA has been reported in cultured A549 lung cells and mouse skin using electrospray, Zeles-Hahn et al. did not observe transfection of luciferase plasmid DNA in a study of tracheal/bronchial epithelial cells cultured at air-liquid interface (Boehringer S, Ruzgys P, Tamo L, Satkauskas S, Geiser T, Gazdhar A, Hradetzky D. A new electrospray method for targeted gene delivery. *Scientific Reports* 2018; 8:4031; and Zeles-Hahn M G, Lentz Y K, Anchordoquy T J, Lengsfeld C S. Effect of electrostatic spray on human pulmonary epithelial cells. *J Electrostat* 2011; 69: 67-77). Another electrospray-based technique is 'bio-electrospray' whereby cells are electrosprayed onto a surface such as an extracellular matrix-like scaffold in a targeted and controlled manner. First reported in 2006, bio-electrospray is being investigated for applications such as tissue engineering and regenerative medicine and we have previously reported successful bio-electrospray of human mesenchymal stem cells (McCrea, Z., Arnanthigo, Y., Cryan, S A., O'Dea, S. A novel methodology for bio-electrospraying mesenchymal stem cells that maintains differentiation, immunomodulatory and pro-reparative functions. *Journal of Medical and Biological Engineering*. 2017. https://doi.org/10.1007/s40846-017-0331-4).

In order to form a stable Taylor cone and plume during electrospraying, solutions can have optimal conductivity, surface tension and viscosity levels (Boehringer S, Ruzgys P, Tamo L, Satkauskas S, Geiser T, Gazdhar A, Hradetzky D. A new electrospray method for targeted gene delivery. *Scientific Reports* 2018; 8:4031). Therefore, solutions typically contain low concentrations of salts as well as solvents such as ethanol. However, the effect of these components on DNA integrity during electrospraying has not been examined. Here we report studies of electrospray parameters for DNA solutions and successful delivery of plasmid DNA, mRNA and siRNA to porcine tracheal explant tissue cultured at an air-liquid interface using low voltage electrosprays with a bench-top instrument. We subsequently used a catheter-based electrospray device to assess the feasibility of electrospray atomisation for the delivery of nucleic acids directly to the lung in a targeted manner, via bronchoscopy, in a porcine ex vivo lung model.

Materials and Methods

Cell Culture

A549 human lung cell line (Cat. No. 86012804, Sigma-Aldrich, Wicklow, Ireland) was routinely cultured in DMEM (Gibco, Thermo Fisher Scientific, Dublin, Ireland) supplemented with 5% fetal bovine serum and 2 mM L-glutamine (Gibco).

Electrospray Studies

The electrospray device comprised a silent air compressor, syringe pump, laser and camera for visualization of the Taylor cone and plume and a control unit (Avectas, Dublin, Ireland). For DNA integrity studies, pEGFP plasmid (Clontech Laboratories, Saint-Germain-en-Laye France) solutions were sprayed into a 24-well cell culture plate (Costar, Sigma-Aldrich) that contained the ground electrode. DNA was diluted in a low salt solution (137 nM NaCl, 1.47 nM $KH_2PO_4$, 8.10 nM $Na_2HPO_4$, 2.68 nM KCl), 1% ethanol/$H_2O$ or 20% ethanol/$H_2O$, all chemicals from Sigma-Aldrich. DNA quantification was carried out using the Nanodrop (Thermo Fisher Scientific). DNA samples were run on a 1% electrophoresis gel, stained with ethidium bromide and scanned using a Gel Doc™ XRS System and Quantity One® software (Bio-Rad Laboratories, Watford, UK).

Lipofection

Lipofectamine 2000 (Invitrogen, Thermo Fisher Scientific) was used to transfect plasmid DNA into A549 cells according to manufacturer's instructions. GFP expression was determined using an Accuri flow cytometer (BD Biosciences, Wokingham, UK) 24 hr post-transfection.

Electrospray Delivery to Cultured Porcine Tracheal Explants

Pig lungs were obtained from a local abattoir. Cold ischaemic time was limited to 90 min. The trachea was dissected into sections approximately 20×50 mm, rinsed with phosphate-buffered saline (PBS) and 3-4 wash cycles in 1:1 RPMI 1640:DMEM, 200 units/ml penicillin, 200 μg/ml streptomycin, 2.5 μg/ml amphotericin, 50 μg/ml gentamicin (all Sigma-Aldrich) were performed. Each wash cycle included changing wash media, 10 minutes of agitation on a cell shaker and 1 hr incubation at 37° C., 5% $CO_2$. Tracheas were cut into 10 $mm^2$ segments, including epithelium, mucosa and cartilage. Tissue segments, epithelial layer facing upwards, were placed onto 5 mm high sterile agarose (1% w/v) plugs in 12-well plates (Costar, Sigma-Aldrich). Culture media (wash media plus 10 mM L-glutamine and 10% FBS) was added so that the basal section of the tissue section was submerged. Explants were incubated overnight at 37° C., 5% $CO_2$, in a humidified atmosphere. For delivery, the electrospray emitter was positioned above a grounded base plate, 15 mm from the epithelial surface of the tissue. Voltage was adjusted between 3-5 kV to achieve a stable Taylor cone and diffuse plume depending on environmental conditions (humidity/temperature). Nucleic acids were resuspended in delivery solution 20% ethanol/$H_2O$. Porcine tissues were placed epithelial surface up, in the centre of a base plate, below the electrospray emitter and nucleic acid solutions were delivered over 2-3 minutes. For pGLuc (New England Biolabs, Ipswich, Mass., USA), three doses 5 μg were delivered over three consecutive days. For luciferease mRNA (TriLink Biotechnologies, San Diego, Calif., USA) and siRNA-FITC (Thermo Fischer Scientific) the total treatment was administered with a single spray. Following nucleic acid delivery, the tissue segments were placed on agarose plugs in fresh culture medium. For pGLuc and luciferase mRNA activity, supernatant was analysed using the Biolux™ Gaussia Luciferase Assay (New England Biolabs) according to manufacturer's instructions. Fluorescence was analysed using the Olympus CKX41 microscope (Olympus, Stansfield, UK).

Electrospray Delivery to Whole Porcine Lung Ex Vivo

The porcine heart-lung block was prepared by cannulating the superior vena cava and perfusing culture medium supplemented with 7% albumin and 0.5% dextran through the pulmonary vasculature with a peristaltic pump (Masterflex, Gelsenkirchen, Germany). The trachea was intubated and ventilated (IPAP 14; EPAP 4; FiO2 21%) using a NIPPY 2 ventilator (RespiCare Ltd., Swords, Ireland). The lungs were cleared of debris by instilling 10 ml aliquots of 0.9% saline and suctioning. The electrospray catheter system was composed of an electrospray catheter, power pack and a syringe pump (Avectas). Prior to bronchoscopy electrospray delivery, a target endobronchial area was selected and marked with 3 dots to form a target using SPOT endoscopic marker (GI Supply, Camp Hill, Pa., USA).

Statistics

Two-tailed, unpaired T-Tests were used for statistical analysis using Graphpad Prism version 7.03 for Windows (GraphPad Software, La Jolla, Calif., USA).

Results

Effect of Electrospray Solution Composition on Plasmid DNA Integrity

Figure 21:
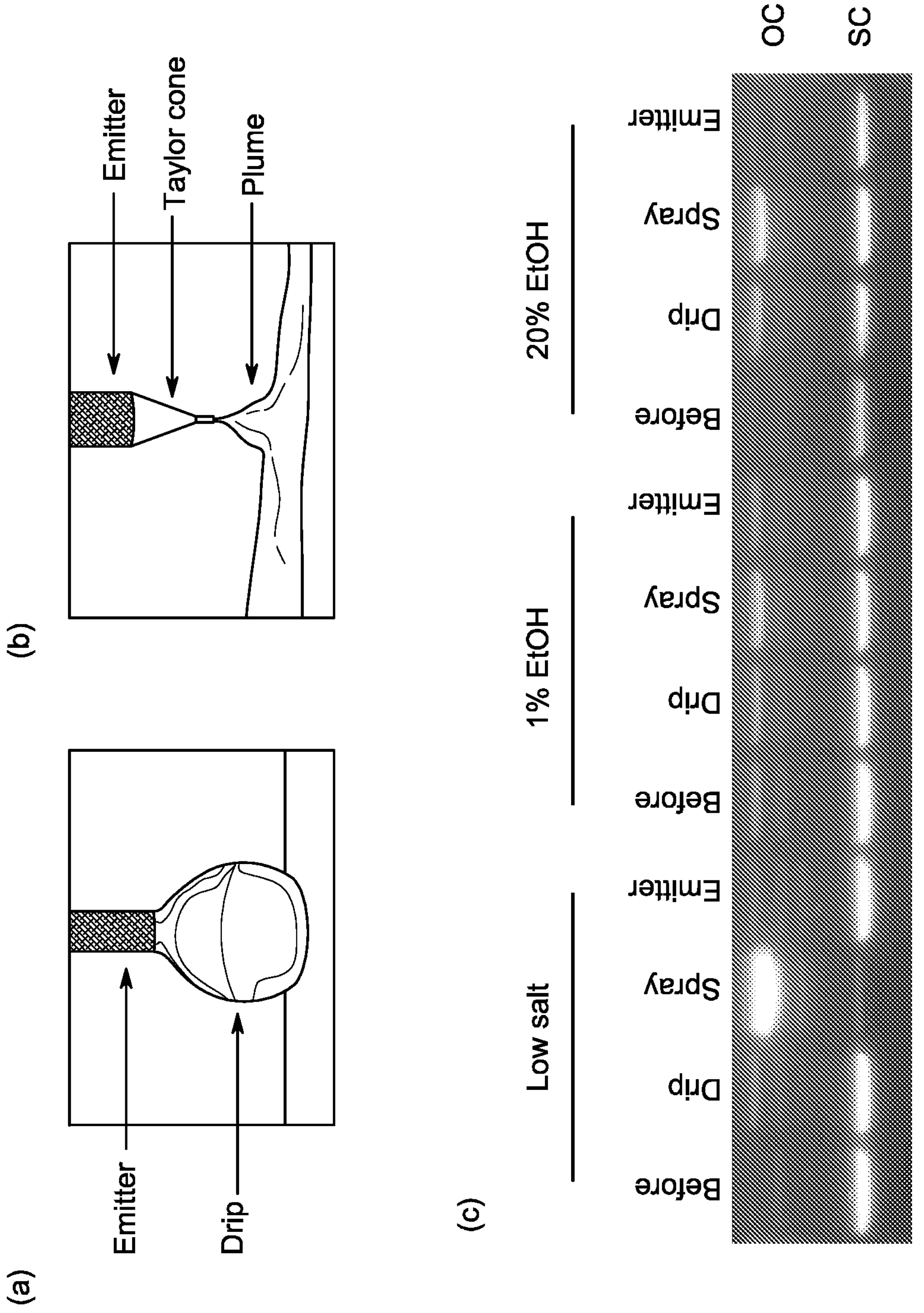
FIG. 21 illustrates effect of electrospray solution composition on plasmid DNA nicking. (a) Solution forms droplet in the absence of applied voltage. (b) Typical electrospray cone-jet mode with plume when voltage is applied. (c) Electrosprayed DNA solutions ('Spray') in low salt, 1% ethanol or 20% ethanol were analysed by gel electrophoresis for the incidence of supercoiled (sc) and open circle (oc) structure. An increase in open circle DNA was evident in the electrosprayed low salt sample. Control samples were taken before solution was placed in emitter ('Before'), before voltage was applied to solution in emitter ('Drip') and from emitter after voltage removed ('Emitter'). Representative gel from three independent experiments is shown.

Zeles-Hahn et al. appear to have used various solutions containing 20 ng/μl GFP DNA without a solvent, the equivalent of a 25 gauge emitter, a flow rate of 200 μl/min and applied voltages of 3-7 kV in negative mode at a distance of 25 mm from ground (Zeles-Hahn M G, Lentz Y K, Anchordoquy T J, Lengsfeld C S. Effect of electrostatic spray on human pulmonary epithelial cells. *J Electrostat* 2011; 69: 67-77). They reported dripping, stable cone-jet and whipping cone electrospray profiles at −3 kV, −6 kV and −7 kV respectively. Boehringer et al. used a sucrose solution containing 100 ng/μl GFP DNA without a solvent, a 29 gauge emitter, flow rate of 20 μl/min, applied voltages of 3 kV in positive mode at distances of 3-6 mm (McCrea, Z., Arnanthigo, Y., Cryan, SA., O'Dea, S. A novel methodology for bio-electrospraying mesenchymal stem cells that maintains differentiation, immunomodulatory and pro-reparative functions. *Journal of Medical and Biological Engineering*. 2017. https://doi.org/10.1007/s40846-017-0331-4). For the present study, we aimed to further study electrospray parameters for transfection of airway tissue and to analyse the effect of these parameters on electrospray mode and DNA integrity. For these studies, we used positive mode electrospray as we found this more conducive than negative mode for the formation of stable sprays (data not shown). Control non-electrosprayed samples were taken either before loading into the electrospray system or generated by allowing solutions to drip through an emitter without the application of an electrical charge and collecting in a tissue culture plate from which they were retrieved for analysis (FIG. 21*a*). When an electric charge was applied to the emitter, the DNA solution formed a classic Taylor cone and plume and these are referred to as 'Spray' samples (FIG. 21*b*).

Covalently closed circular DNA will adopt a supercoiled topology. A single break on one strand of the molecule will result in the release of the supercoiled form into an open circle form. Another cleavage on the opposite strand will result in a linear DNA form. Further DNA nicks will result in fragmentation of the DNA. Any of these events could lead to reduced transfection efficiency.

Three solutions containing low concentration salts or ethanol were selected and their effect on DNA integrity during electrospray was determined. DNA (pEGFP, 100 ng/μl) was resuspended in low salt solution, 1% ethanol/$H_2O$ or 20% ethanol/$H_2O$. Solutions were delivered at flow rates of 5 μl/min for 5 min into empty tissue culture plates and retrieved for analysis. All solutions achieved plume electrospray mode, however voltages of approximately 4 kV were typically required for the low salt and 1% ethanol solutions compared with 3 kV for the 20% ethanol solution. We also observed that the low salt and 1% ethanol solutions had narrower plumes and were less stable over time compared with the 20% ethanol solution. There was an increase in open circle form of the plasmid in the sprayed low salt solution compared with the ethanol solutions indicating increased single strand nicking (SSN) in the low salt solution (FIG. 21*c*).

Effects of Emitter Gauge and Flow Rate

Emitter gauge and solution flow rates are two further parameters that affect Taylor cone formation and the ability to generate a stable electrospray. We therefore used the low salt solution to examine whether these two parameters were contributing to the nicking observed in the DNA plasmid.

Plasmid DNA in low salt solution was electrosprayed at four different flow rates (40 μl/min, 20 μl/min, 10 μl/min and 5 μl/min) through six different sized emitters (22, 23, 25, 27, 30, 32 gauge). For each emitter gauge tested, each flow rate was compared to the corresponding 40 ul/min drip control. While there was no statistically significant difference in the supercoiled: open circular ratio between the samples, there was a trend towards the 32 ga emitter preserving the highest levels of supercoiled plasmid at all flow rates (FIG. 22*a*).

Figure 22:
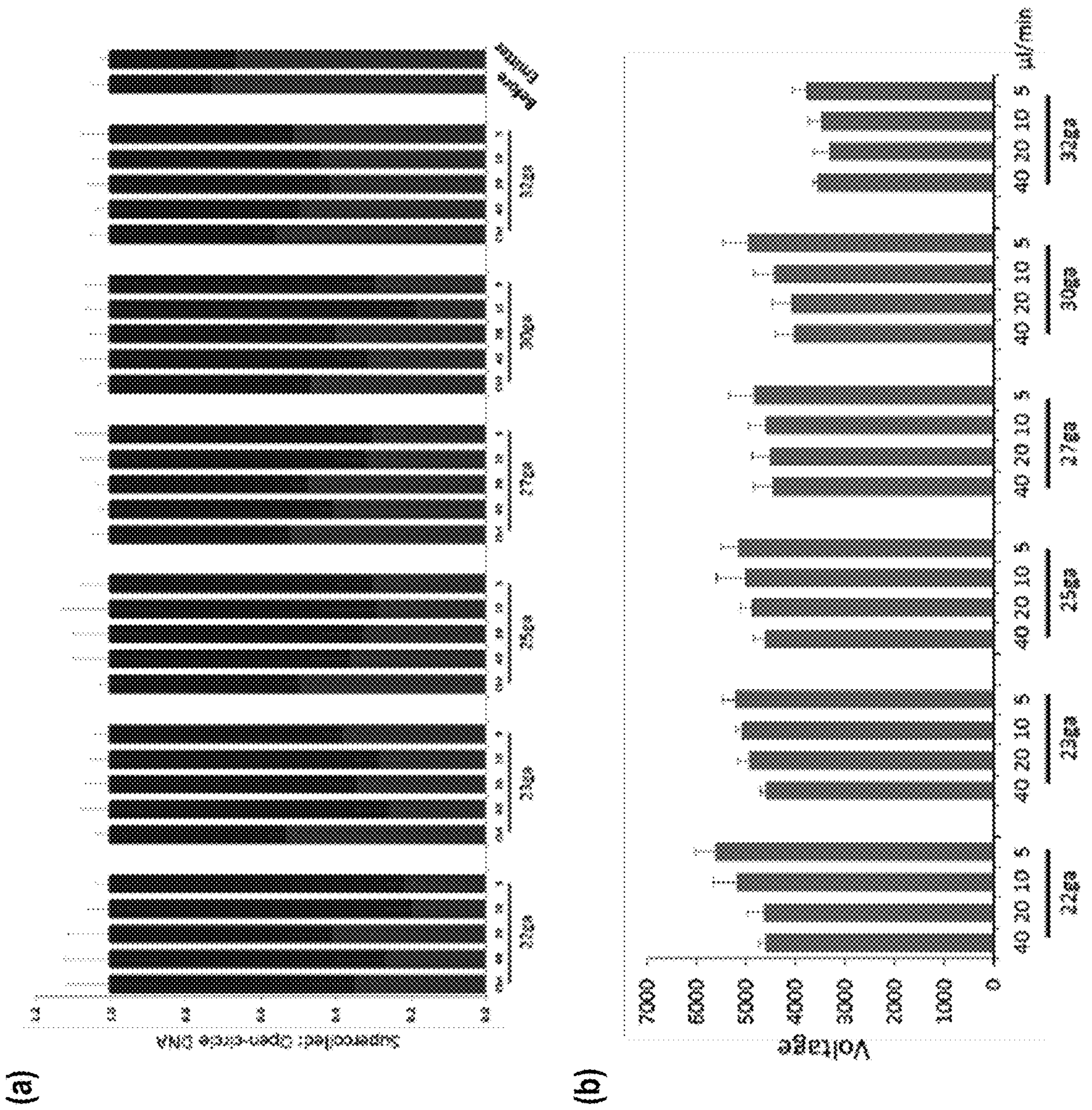
FIG. 22 illustrates effects of flow rate and emitter size on plasmid DNA nicking. (a) Plasmid DNA was electrosprayed in low salt solution through various emitter gauges at various flow rates. The ratio of supercoiled (sc) versus open circle (oc) structure was analysed by gel electrophoresis and densitometry. Control samples were taken before solution was placed in emitter ('Before') and from emitter after voltage removed ('Emitter'). While there was no statistical difference between the conditions, there was a trend towards the 32 gauge emitter preserving the highest levels of supercoiled plasmid at all flow rates. (b) The voltage required to produce a stable electrospray was recorded and was found to decrease as the emitter guage increased. N=3 independent experiments, ga=gauge.

The voltage required to form a stable cone-jet electrospray for each emitter was noted and it was observed that higher voltages were required for the wide internal diameter emitters (22 ga) compared to the narrower internal diameter emitters (32 ga) (FIG. 22*b*). These results suggest that although the larger internal diameter emitters caused more plasmid nicking, this was likely due to the higher voltages required to achieve a Taylor cone and plume electrospray.

Effect of High Voltage

We next examined the effects of voltage on DNA nicking. For these experiments the resistance was kept constant and the voltage was increased in order to assess the effect of current on DNA nicking. The voltages examined were 3 kV, 4 kV, 5 kV and 6 kV. Flow rates of 60 and 15 μl/min and emitter gauges of 22 ga and 32 ga were tested. Plasmid DNA was electrosprayed in low salt solution.

Figure 23:
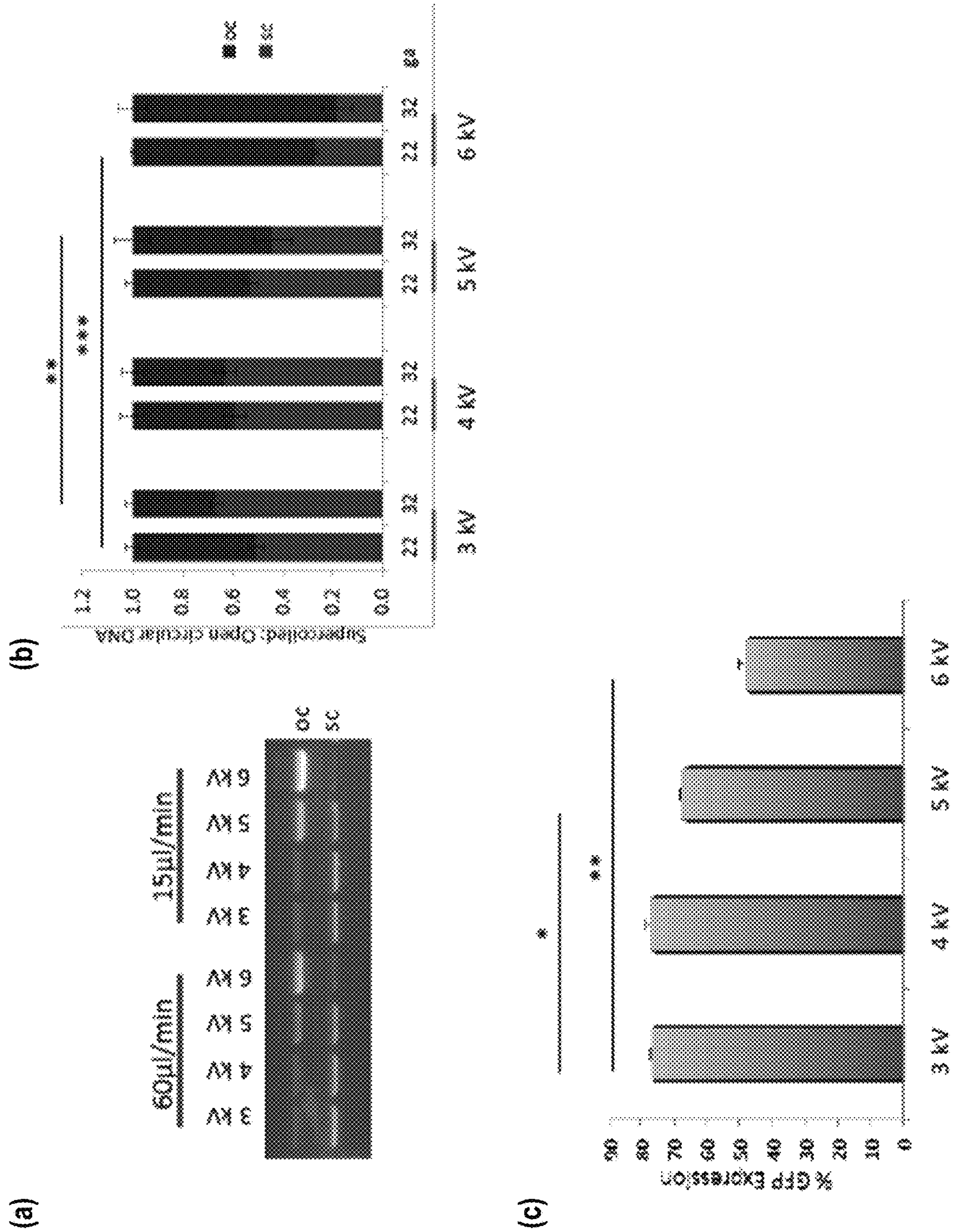
FIG. 23 illustrates effect of voltage on plasmid DNA nicking. (a) Plasmid DNA was electrosprayed in low salt solution through a 32 gauge emitter at 60 μl/min or 15 μl/min and DNA nicking was analysed by gel electrophoresis. Increases voltage caused an increase in the incidence of open circle (oc) structure compared with supercoiled (sc). (b) Emitter gauge did not affect the incidence of open circle structure. (c) GFP DNA was electropsrayed at varying voltages (emitter size 32 ga at flow rate 60 μl/min) and transfected with Lipofectamine 2000 into A549 cells. The efficiency of GFP transfection was reduced with increasing voltage.

Firstly, the effect of these parameters on spray mode was observed by eye (FIG. 23). At 3 kV the potential was not high enough to generate a spray at either flow rate or with either emitter gauge. At 4 kV, for both flow rates, a spray was generated with the 32 ga emitter but not the 22 ga emitter, which remained in drip mode. At 5 kV, for both flow rates, an unstable spray that alternated between drip and spray was observed with the 22 ga emitter while a stable spray was generated with the 32 ga emitter. At 6 kV the electrical potential was high enough to generate a continuous stable electrospray with both emitter sizes and both flow rates.

DNA nicking was next examined at each voltage, flow rate and emitter gauge. Firstly, using a 32 ga emitter, an increase in plasmid nicking was observed with increasing voltage at both 60 and 15 μl/min flow rates, as indicated by an increase in the level of open-circle plasmid DNA (FIG. 23*a*). When the flow rate was kept constant at 60 μl/min and the voltage was increased, there was no significant difference in supercoiled: open circular ratio between 22 ga or 32 ga emitters indicating that emitter gauge per se does not affect DNA integrity (FIG. 23*b*). However, there was increased plasmid nicking as the voltage increased. There was a significant increase in plasmid nicking using the 22 ga emitter at 6 kV compared to 3 kV ($p=0.0003$). There was also a significant increase in plasmid nicking using the 32 ga emitter at 5 kV compared to 3 kV ($p=0.002$). These results indicate that high voltage, or more specifically the higher current that this equates to, is the causative factor of DNA nicking during electrospray.

To determine the consequence of plasmid nicking on DNA expression, a plasmid encoding for green fluorescent protein (pGFP) was subjected to electrospray and subsequently transfected into A549 lung epithelial cells by lipofection. Equal concentrations of DNA were lipofected and the transfection efficiency was determined. Increased levels of DNA nicking correlated with decreased levels of GFP expression (FIG. 23*c*). This indicates that single strand nicking of plasmid DNA induced by high voltage leads to open-circular confirmation and ultimately a reduction in downstream protein expression.

Electrospray Delivery of Plasmid DNA, mRNA and siRNA to Cultured Porcine Tracheal Explants Having examined the effects of various electrospray parameters on integrity of nucleic acids, we then went on to assess the feasibility of delivery to airway tissue. Two ex vivo model systems were used: cultured porcine tracheal explants and whole porcine lung. Various reporter plasmids have been used in studies aimed at developing vectors for gene therapy for airway diseases. A secreted Gaussia princeps luciferase (GLuc) reporter gene has been shown to be a sensitive reporter in pre-clinical studies of gene transfer in cystic fibrosis models so this plasmid (pGLuc) was used for studies here (Griesenbach U, Vicente C C, Roberts M J, Meng C, Soussi S, Xenariou S, Tennant P, Baker A, Baker E, Gordon C, Vrettou C, McCormick D, Coles R, Green A M, Lawton A E, Sumner-Jones S G, Cheng S H, Scheule R K, Hyde S C, Gill D R, Collie D D, McLachlan G, Alton E W. Secreted Gaussia luciferase as a sensitive reporter gene for in vivo and ex vivo studies of airway gene transfer. *Biomaterials.* 2011 32(10):2614-24). Based on results above, the following parameters were deemed best for maintaining integrity of nucleic acid molecules: 20% ethanol/$H_2O$ as delivery solution, 32 ga emitter and low flow rates.

Figure 24:
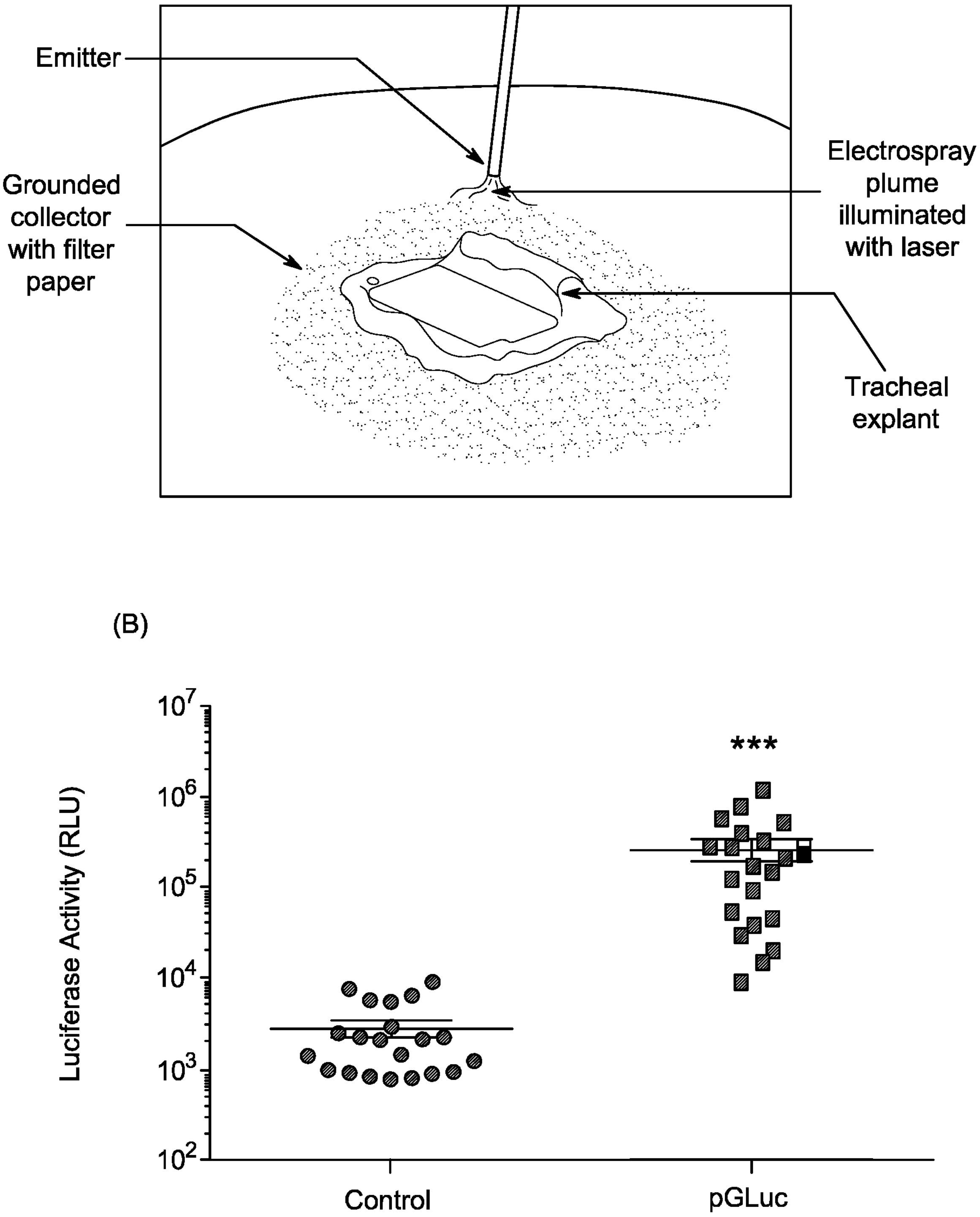
FIG. 24 illustrates electrospray delivery of plasmid DNA to porcine tracheal explants. (a) Electrospray plume visualised with a laser during delivery to tissue demonstrating emitter, electrospray plume, tissue explant and grounded collector. (b) Quantification of Gaussia luciferase activity following pGLuc transfection compared to negative control (pEGFP). n=21. *** $p<0.001$.

Porcine tracheal explants were electrosprayed with 5000 ng pGLuc (833 ng/μl; flow rate 3 μl/min; duration 2 min) once each day for 3 consecutive days and tissues were then cultured for a further 48 hr (FIG. 24*a*). 20 μl of culture media was sampled from each well and luciferase activity was quantified. There was a significant increase in luciferase activity ($p=0.0002$) in the media of pGLuc electrosprayed tissue compared to the media from electrosprayed controls (FIG. 24*b*).

Figure 25:
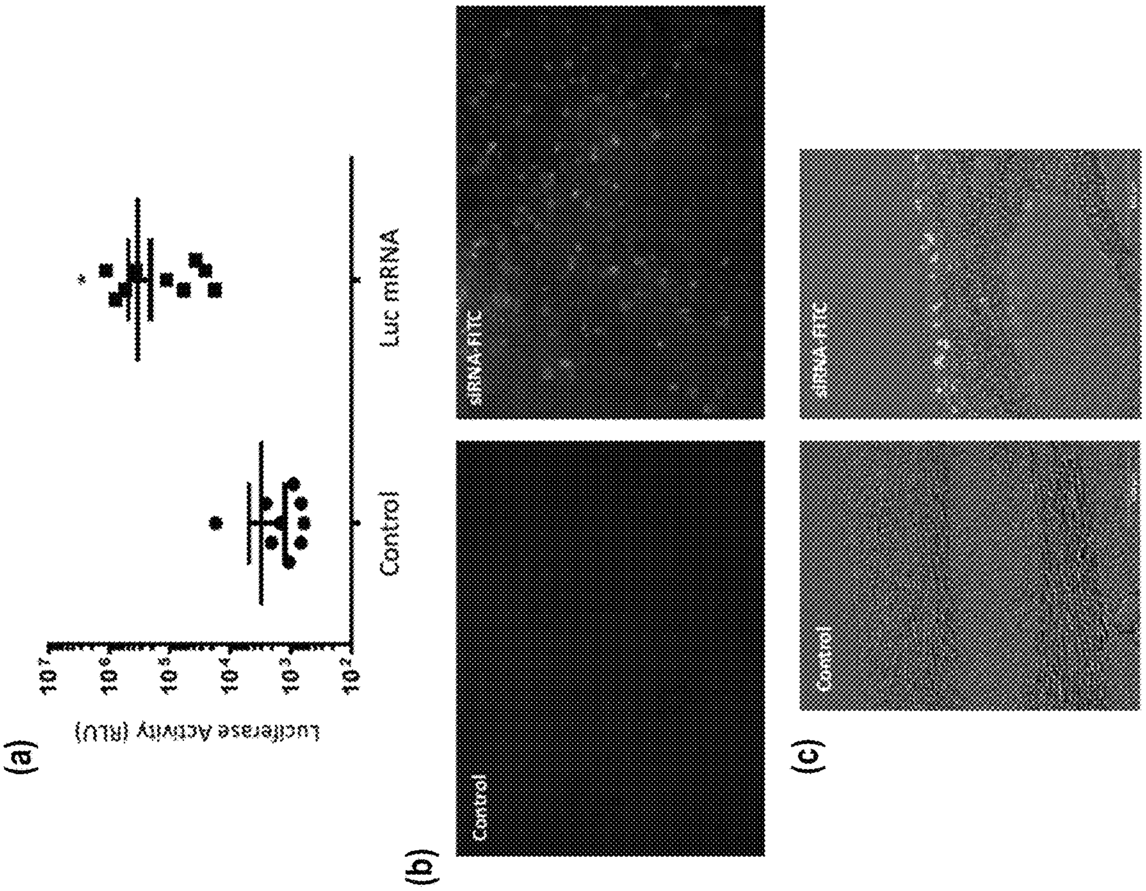
FIG. 25 illustrates electrospray delivery of RNA to porcine tracheal explants. (a) Quantification of luciferase activity following luciferase mRNA transfection compared to buffer-only control. n=9. * $p<0.05$. Representative fluorescence microscopy images of FITC localisation following siRNA-FITC delivery compared to buffer-only control are shown for (b) microdissected epithelial layer and (c) tracheal segments cryosectioned in the transverse plane, 20× magnification.

We next evaluated electrospray delivery of RNA molecules. mRNA encoding for luciferase was performed on porcine tracheal tissue. Luciferase mRNA (10 μg) was electrosprayed onto the trachea tissue (700 ng/μl; flow rate 4.8 μl/min; duration 3 min) and incubated for 48 hours. Delivery solution without mRNA was electrosprayed as a negative control. Quantification of luciferase activity showed a significant increase in luminescence expression ($p=0.023$) in the mRNA electrosprayed samples compared to control explants (FIG. 25*a*).

siRNA-FITC (20 μl 100 μM) was delivered to the trachea explant (100 μM; flow rate 10 μl/min; duration 2 min) and compared to a delivery solution-only negative control. Following delivery, the epithelial layer was microdissected and examined under a fluorescent microscope. FITC fluorescence was evident in tissue that were electrosprayed with siRNA but not in control tissue (FIG. 25*b*). In addition, tracheal segments were cryosectioned in the transverse plane, allowing visualisation of siRNA within the tissue (FIG. 25*c*).

Bronchoscopic Electrospray Delivery of mRNA to Whole Porcine Lung Ex Vivo

Figure 26:
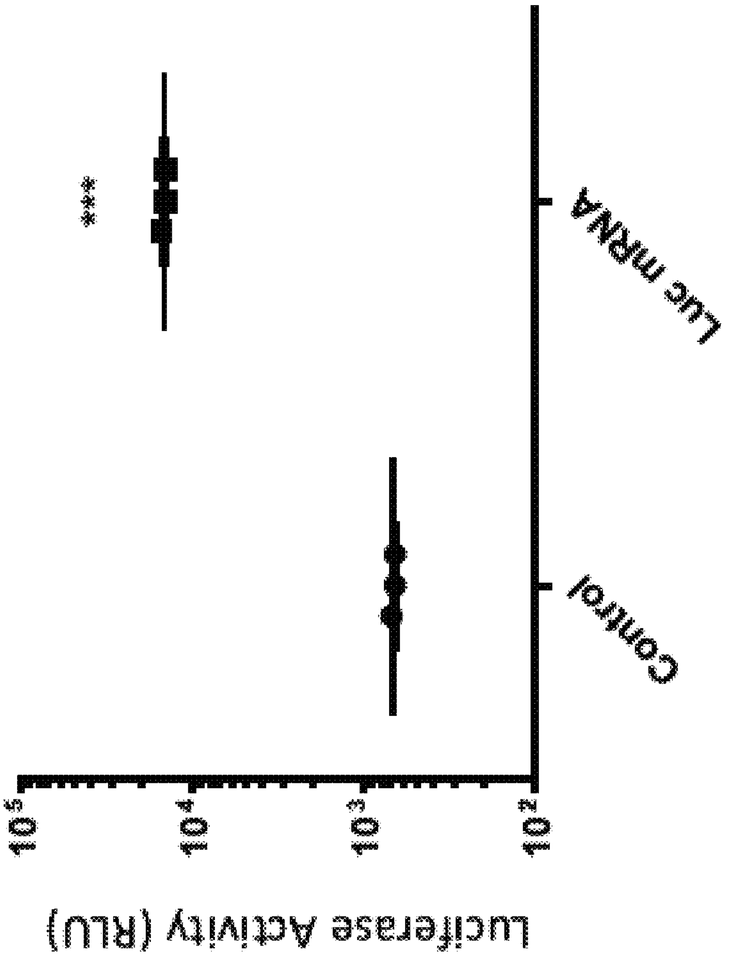
FIG. 26 illustrates Bronchoscopic electrospray delivery of mRNA to whole porcine lungs ex vivo. Quantification of luciferase activity following luciferase mRNA transfection, compared to buffer-only control. n=3. *** $P<0.001$.

We next examined whether electrospray could be used to deliver nucleic acids to the airways within whole lungs. An apparatus was set up comprising catheter, bronchoscope and electrospray equipment as before (FIG. 20). Dissected lungs were obtained and prior to bronchoscopic electrospray delivery, a target endobronchial area was selected and marked with 3 dots to form a target using SPOT endoscopic marker. The electrospray catheter was then inserted into the working port of a bronchoscope, positioned 15 mm from the premarked target and deliver solution containing mRNA was delivered to the centre of the dots. 10 μl (3 μg) mRNA-GLuc (300 ng/μl; flow rate 100 μl/sec; duration 0.1 sec) was delivered to target areas which were then resected, washed and cultured at air liquid interface. Luciferase activity was measured at 48 hr post-delivery. A significant ($p<0.0001$) increase in luciferase activity was detected in luciferase mRNA-treated samples compared to controls (FIG. 26).

Discussion

Nucleic acid based therapies have significant disease modifying potential. As such, there has been much interest in developing techniques that successfully deliver these molecules in vivo. Multiple viral and non-viral vectors have been utilised for this aim, but success has been limited to date. Challenges of cytotoxicity, immunogenicity and transfection inefficiency have hampered progress. Improved safety profiles with non-viral vectors have increased interest in these techniques. However, technologies to improve transfection efficacy are needed if non-viral vector therapies are to have a clinically meaningful effect. This study is the first, to our knowledge, to report the successful electrospray delivery of RNA or DNA molecules to lung tissue. Porcine lung was selected as a target for gene delivery in view of its extensive use in translational research and its close approximation of the human lung for bronchoscopic intervention (Rogers C S, Abraham W M, Brogden K a, Engelhardt J F, Fisher J T, McCray P B et al. The porcine lung as a potential model for cystic fibrosis. *Am J Physiol Lung Cell Mol Physiol* 2008; 295: L240-L263; and Judge E P, Hughes J M L, Egan J J, Maguire M, Molloy E L, O'Dea S. Anatomy and bronchoscopy of the porcine lung: A model for translational respiratory medicine. *Am. J Respir. Cell Mol. Biol.* 2014; 51: 334-343). Furthermore, the epithelial surface of the lung provides an accessible target for non-invasive (inhalation) and semi-invasive (bronchoscopy) drug delivery. Electrospray atomisation has the potential to be utilised as a drug delivery platform for both modalities.

Electrospray ionisation is a vector-free delivery system that has the potential to overcome multiple barriers associated with inefficient transfection. This technique has previously been reported to successfully transfect plasmid DNA in vitro and to mouse skin (Boehringer S, Ruzgys P, Tamo L, Satkauskas S, Geiser T, Gazdhar A, Hradetzky D. A new electrospray method for targeted gene delivery. *Scientific Reports* 2018; 8:4031; Ikemoto K, Sakata I, Sakai T. Collision of millimeter droplets induces DNA and protein transfection into cells. *Sci Rep* 2012; 2: 1-5; and Lee Y H, Wu B, Zhuang W Q, Chen D R, Tang Y J. Nanoparticles facilitate gene delivery to microorganisms via an electrospray process. *J Microbiol Methods* 2011; 84: 228-233). Here we report the successful electrospray ex vivo delivery of plasmid DNA, mRNA and siRNA molecules. In this study, protein expression following transfection was identified, indicating that biological integrity of nucleic acid solutions is maintained during the electrospray process.

Zeles-Hahn et al. failed to achieve transfection of luciferase DNA in the form of naked plasmid DNA, lipid/DNA complexes, polyethyleneimine/DNA complexes and poly L-lysine/DNA complexes into human airway epithelial cells (Zeles-Hahn M G, Lentz Y K, Anchordoquy T J, Lengsfeld C S. Effect of electrostatic spray on human pulmonary epithelial cells. *J Electrostat* 2011; 69: 67-77). They do not appear to have used a solvent and this may have necessitated high voltages in order to cause the solution to break up into a spray. Such voltages may damage the structure of the DNA plasmid and they report an increase in open circle and fragmented DNA at 6 kV and 7 kV.

The process of electrospray atomisation involves the generation of an electric field between a charged solution and a grounded collector. As the electromagnetic field overcomes surface tension, the solution is dispersed into nanosized particles that move towards a collector at high velocity. The characteristics of electrospray generated particles—size, charge, velocity and direction—may benefit delivery by potentially addressing factors that reduce the efficiency of nucleic acid delivery to tissue. Electrospray may create conditions where particles pass through a cell membrane by kinetic force, as happens with a 'gene gun' (Zhang D, Das D B, Rielly C D. Potential of microneedle-assisted microparticle delivery by gene guns: a review. *Drug Deliv* 2013; 7544: 571-587). This may also be achieved by the interaction of charged particles with membrane-bound voltage gates or ion channels. In addition, the electric field associated with an electrospray may induce the transient formation of pores within the cell membrane, known as electroporation (Lambricht L, Lopes A, Kos S, Sersa G, Préat V, Vandermeulen G. Clinical potential of electroporation for gene therapy and DNA vaccine delivery. *Expert Opin Drug Deliv* 2015; 5247: 295-310).

Delivery of plasmid DNA to tissue can be challenging because the large size of these molecules can negatively impact upon cellular uptake. In addition, cellular uptake of DNA does not guarantee protein expression as nucleolar relocation must occur before protein encoding can commence. We hypothesised that the delivery of smaller molecules, such as mRNA, would increase the efficacy of protein expression by removing barriers associated with molecular size and ribosomal transcription. mRNA may also have therapeutic advantages over DNA, where factors such as transient protein expression may be an important consideration in drug development. In our study, we did not directly compare transfection efficiency of mRNA to plasmid DNA, however a 2 log increase in luciferase activity was seen with both plasmid DNA and mRNA compared to controls.

Gene regulation, and therefore disease modulation, by siRNA molecules also have great potential for treating conditions such as cancer (Golan T, Khvalevsky E Z, Hubert A, Gabai R M, Hen N, Segal A et al. RNAi therapy targeting KRAS in combination with chemotherapy for locally advanced pancreatic cancer patients. *Oncotarget* 2015; 6: 24560-24570). We have shown that fluorescent labelled siRNA molecules can be delivered to the epithelial and mucosal layers of lung tissue by electrospray. While siRNA function was not assessed in the study, this therapeutic approach would have the potential to downregulate disease pathways during infection, inflammation or oncogenesis (Zamora M R, Budev M, Rolfe M, Gottlieb J, Humar A, DeVincenzo J et al. RNA interference therapy in lung transplant patients infected with respiratory syncytial virus. *Am J Respir Crit Care Med* 2011; 183: 531-538; Lomas-Neira J L, Chung C-S, Wesche D E, Perl M, Ayala A. In vivo gene silencing (with siRNA) of pulmonary expression of MIP-2 versus K C results in divergent effects on hemorrhage-induced, neutrophil-mediated septic acute lung injury. *J Leukoc Biol* 2005; 77: 846-53; and Davis M E, Zuckerman J E, Choi C H J, Seligson D, Tolcher A, Alabi C A et al. Evidence of RNAi in humans from systemically administered siRNA via targeted nanoparticles. *Nature* 2010; 464: 1067-1070).

REFERENCES

1. Duncan G A, Jung J, Hanes J, Suk J S. The Mucus Barrier to Inhaled Gene Therapy. *Mol Ther* 2016; 24: 2043-2053.
2. Gomes dos Reis L, Svolos M, Hartwig B, Windhab N, Young P M, Traini D. Inhaled gene delivery: a formulation and delivery approach. *Expert Opin Drug Deliv* 2017; 14: 319-330.1
3. Jaworek A, Sobczyk A T. Electrospraying route to nanotechnology: An overview. *J Electrostat* 2008; 66: 197-219.
4. Rosell-Llompart J, Fernández de la Mora J. Generation of monodisperse droplets 0.3 to 4 μm in diameter from electrified cone-jets of highly conducting and viscous liquids. *J Aerosol Sci* 1994; 25: 1093-1119.

5. Boehringer S, Ruzgys P, Tamo L, Satkauskas S, Geiser T, Gazdhar A, Hradetzky D. A new electrospray method for targeted gene delivery. *Scientific Reports* 2018; 8:4031.
6. Zeles-Hahn M G, Lentz Y K, Anchordoquy T J, Lengsfeld C S. Effect of electrostatic spray on human pulmonary epithelial cells. *J Electrostat* 2011; 69: 67-77.
7. McCrea, Z., Arnanthigo, Y., Cryan, S A., O'Dea, S. A novel methodology for bio-electrospraying mesenchymal stem cells that maintains differentiation, immunomodulatory and pro-reparative functions. *Journal of Medical and Biological Engineering*. 2017. https://doi.org/10.1007/s40846-017-0331-4.
8. Griesenbach U, Vicente C C, Roberts M J, Meng C, Soussi S, Xenariou S, Tennant P, Baker A, Baker E, Gordon C, Vrettou C, McCormick D, Coles R, Green A M, Lawton A E, Sumner-Jones S G, Cheng S H, Scheule R K, Hyde S C, Gill D R, Collie D D, McLachlan G, Alton E W. Secreted Gaussia luciferase as a sensitive reporter gene for in vivo and ex vivo studies of airway gene transfer. *Biomaterials*. 2011 32(10):2614-24.
9. Ikemoto K, Sakata I, Sakai T. Collision of millimeter droplets induces DNA and protein transfection into cells. *Sci Rep* 2012; 2: 1-5.
10. Lee Y H, Wu B, Zhuang W Q, Chen D R, Tang Y J. Nanoparticles facilitate gene delivery to microorganisms via an electrospray process. *J Microbiol Methods* 2011; 84: 228-233.
11. Rogers C S, Abraham W M, Brogden K a, Engelhardt J F, Fisher J T, McCray P B et al. The porcine lung as a potential model for cystic fibrosis. *Am J Physiol Lung Cell Mol Physiol* 2008; 295: L240-L263.
12. Judge E P, Hughes J M L, Egan J J, Maguire M, Molloy E L, O'Dea S. Anatomy and bronchoscopy of the porcine lung: A model for translational respiratory medicine. *Am. J. Respir. Cell Mol. Biol.* 2014; 51: 334-343.
13. Zhang D, Das D B, Rielly C D. Potential of microneedle-assisted micro-particle delivery by gene guns: a review. *Drug Deliv* 2013; 7544: 571-587.
14. Lambricht L, Lopes A, Kos S, Sersa G, Préat V, Vandermeulen G. Clinical potential of electroporation for gene therapy and DNA vaccine delivery. *Expert Opin Drug Deliv* 2015; 5247: 295-310.
15. Golan T, Khvalevsky E Z, Hubert A, Gabai R M, Hen N, Segal A et al. RNAi therapy targeting KRAS in combination with chemotherapy for locally advanced pancreatic cancer patients. *Oncotarget* 2015; 6: 24560-24570.
16. Zamora M R, Budev M, Rolfe M, Gottlieb J, Humar A, DeVincenzo J et al. RNA interference therapy in lung transplant patients infected with respiratory syncytial virus. *Am J Respir Crit Care Med* 2011; 183: 531-538.
17. Lomas-Neira J L, Chung C-S, Wesche D E, Perl M, Ayala A. In vivo gene silencing (with siRNA) of pulmonary expression of MIP-2 versus K C results in divergent effects on hemorrhage-induced, neutrophil-mediated septic acute lung injury. *J Leukoc Biol* 2005; 77: 846-53.
18. Davis M E, Zuckerman J E, Choi C H J, Seligson D, Tolcher A, Alabi C A et al. Evidence of RNAi in humans from systemically administered siRNA via targeted nanoparticles. *Nature* 2010; 464: 1067-1070.

Experiment 3—Porous Tip Emitter Head

To investigate the viability of using a porous tip, a felt tip part of a writing instrument (e.g., Copic markers) was tested. A high-voltage electrical connection was made with a copper washer. Testing equipment included the electrospray device base rig with a power supply, a flat plate counter electrode mounted on a lab jack. For performance diagnosis, a microscopic a VIMS videoscope was placed near the tip to provide illumination.

Figure 28:
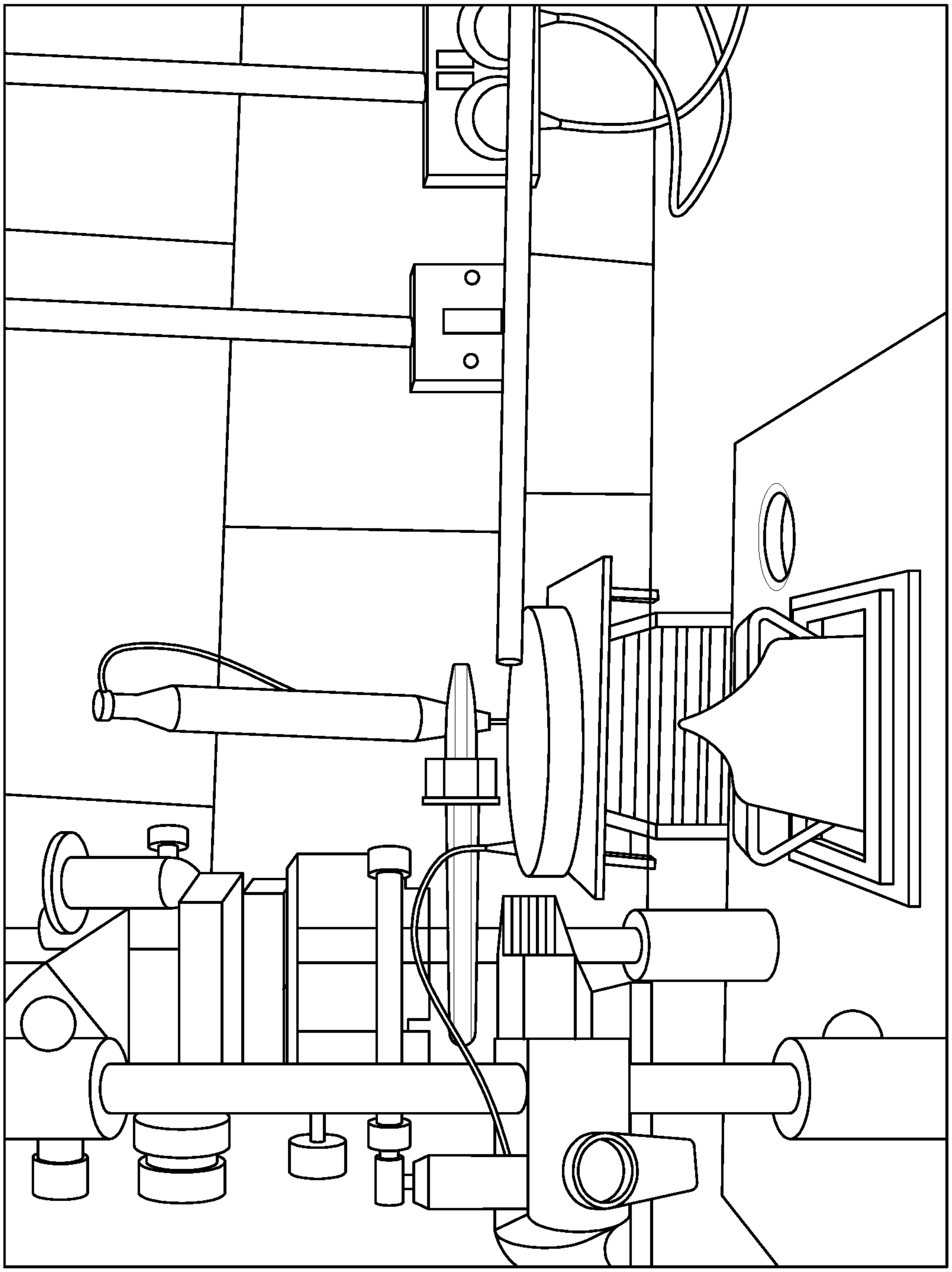
FIG. 28 illustrates a setup to test electrospray formation using an example porous tip of a writing instrument.
Figure 29:
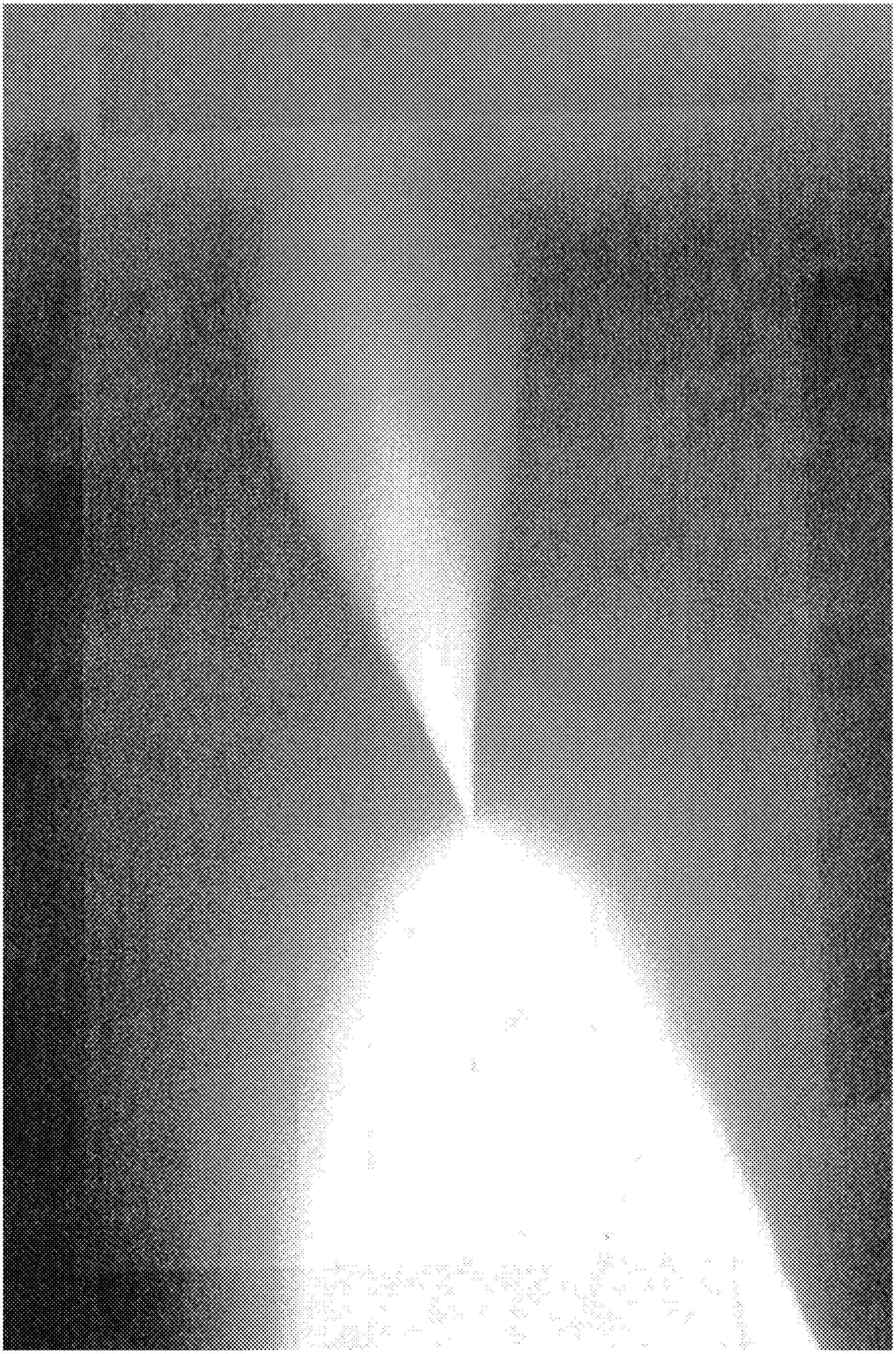
FIG. 29 illustrates a stable cone-jet mode spray formed at an example porous tip using 77% ethanol.
Figure 30:
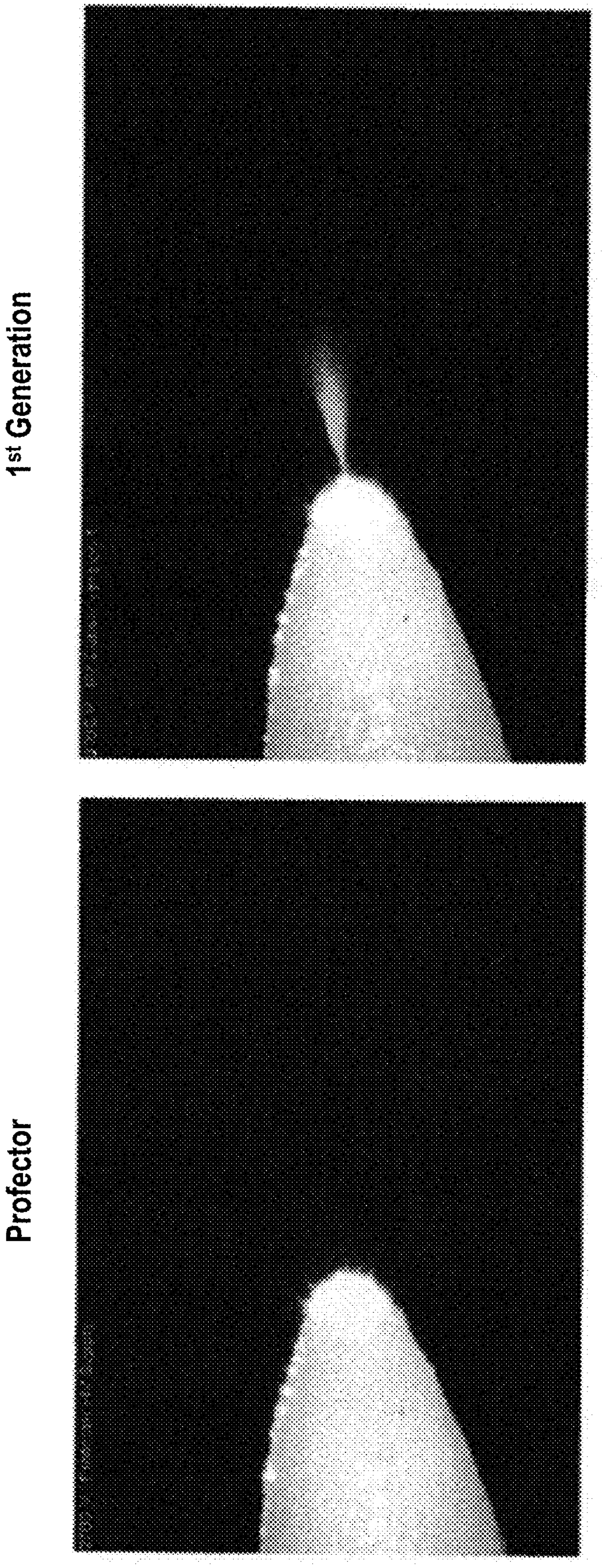
FIG. 30 illustrates electrospray formation at a porous tip using a two power supplies.

For an experiment, 77% ethanol was supplied from the proximal end of the writing instrument as illustrated in FIG. 28. FIGS. 29 and 30 show the electrospray formation using the porous tip. Experiment results show that the porous tip can establish a uniform and stable spray at supply voltages ranging from 2.0 to 2.9 kV at tip-to-plate distances of 10 to 15 mm. Above 2.9 kV, a multijet mode where two or more distinct jets are observed was established. The uniform spray was demonstrated by a clear deposition of the liquid on the counter electrode. Placing a plastic insert onto the flat plate collector showed similar behavior observed with the steel needle, i.e., the spray was deflected by the insert and deposited around it. A ring deposition pattern was observed indicating that the electric field lines were deflected by the plastic insert.

Figure 31:
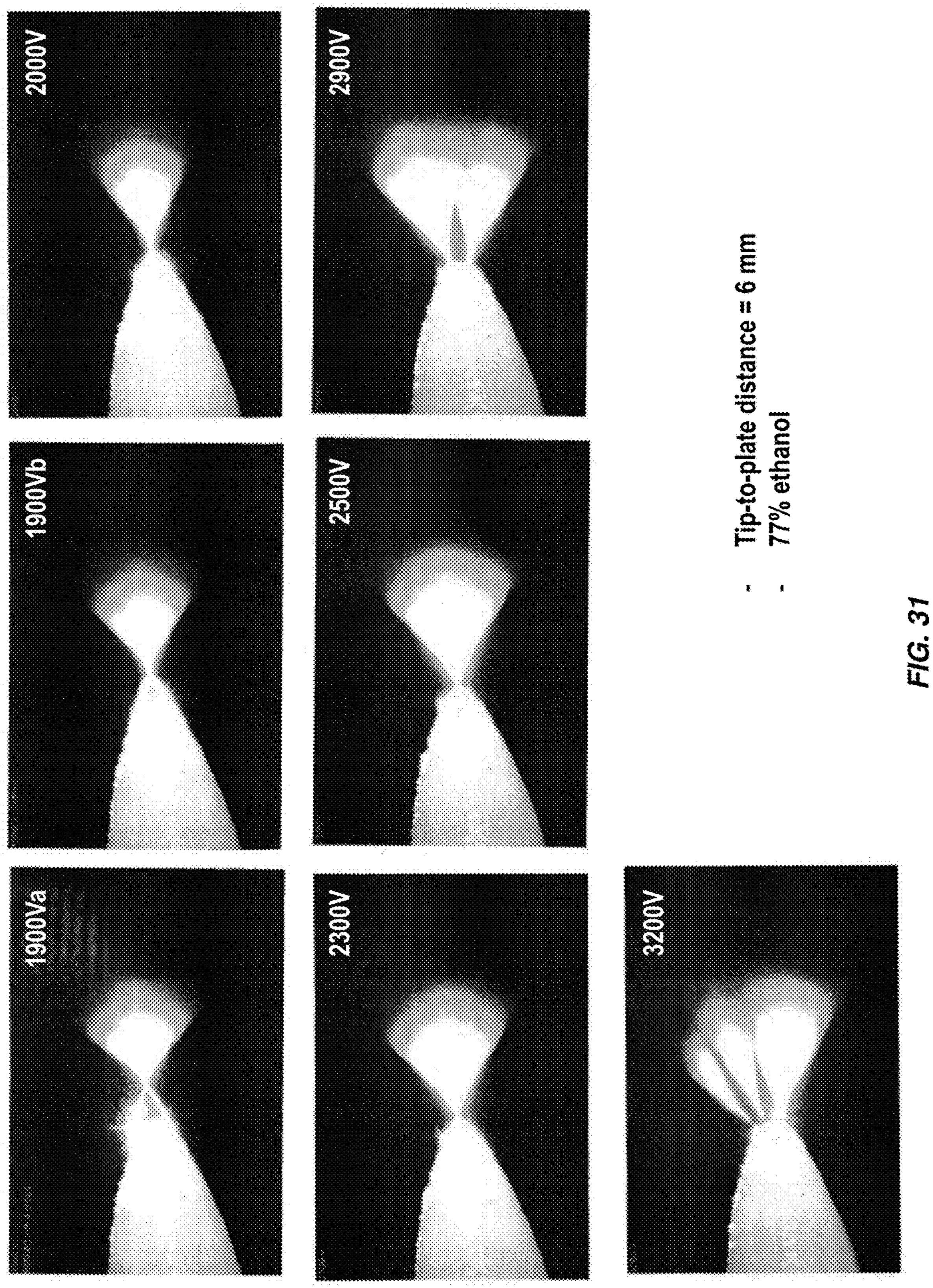
FIG. 31 illustrates electrospray formation at an example porous tip at various supply voltages using 77% ethanol with a tip-to-plate distance of 6 mm.
Figure 32:
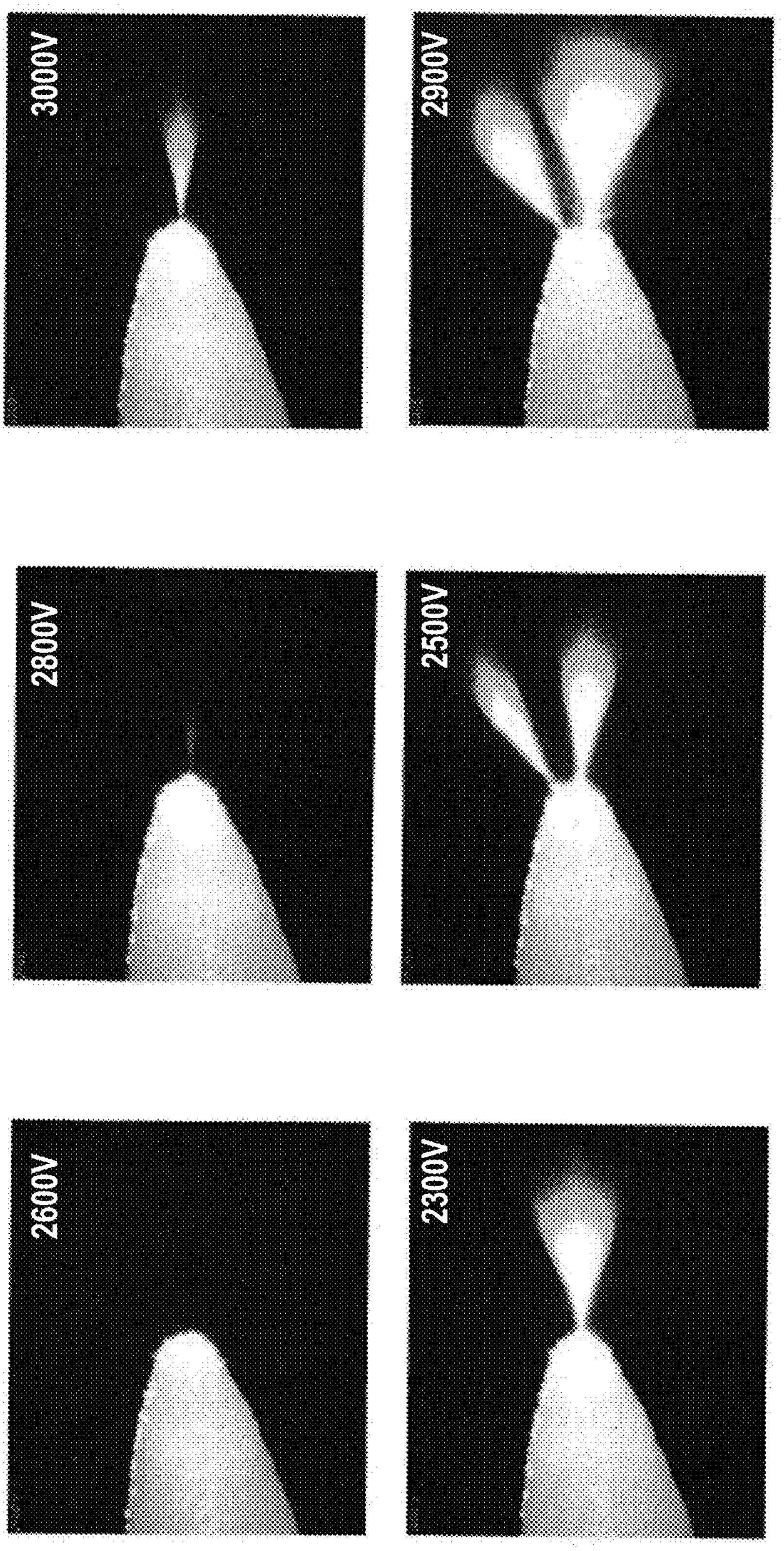
FIG. 32 illustrates electrospray formation at an example porous tip at various supply voltages using 77% ethanol with a tip-to-place distance of 26 mm.
Figure 33:
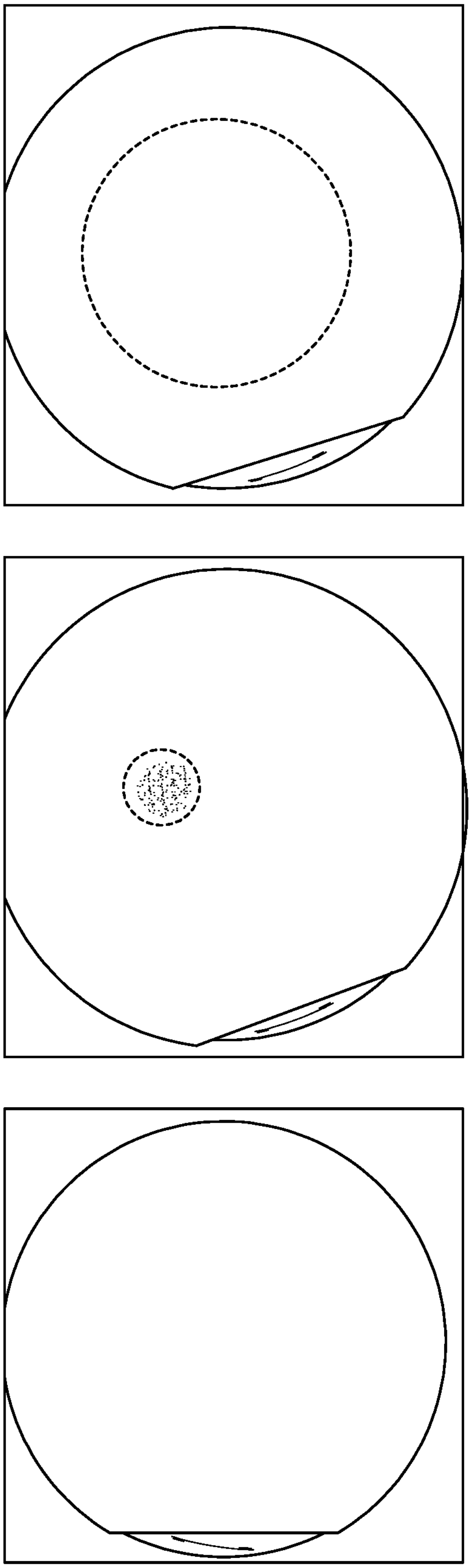
FIG. 33 illustrates electrospray pattern on the electrode plate obtained by using a porous tip for no spray, tip-to-plate distance of 6 mm, and tip-to-plate distance of 26 mm, respectively.

In another variation of the delivery platform with the porous tip, a class 2 laser light source may be used to illuminate the plume as the monochromatic and collimated light source can provide better illumination. In another experiment, it was demonstrated that the electrospray can supply a stable cone-jet mode spray for about 2 minutes and 52 seconds when filled with 100 μL of liquid and subject to a supply voltage of 2.7 kV with a tip-to-plate distance of 6 mm or about 5 minutes and 32 seconds with a tip-to-plate distance of 26 mm. At a tip-to-plate distance of 26 mm, stable cone-jet mode was observed from 2.8 kV to 3.4 kV while above 3.7 kV, multijet mode started to appear. Observation of the electrode plate showed that the coverage pattern had a larger diameter at a tip-to-place distance of 26 mm than at 6 mm. No coverage was observed with no spray. FIGS. 31-33 show experimental results for various supply voltages using the porous tip with 77% ethanol at different tip-to-plate distances.

Various porous tips with different configurations were also tested. Specifically, 4 different nibs from Copic writing instrument products: standard super brush, standard fine, brush, and multiliner were tested. The brush and multiliner nibs had metal connections, but the standard fine and super brush needed the connectors to be made. Among the ones that were tested, the standard fine demonstrated a stable con-jet formation. The testing procedure was saturating the nib and adding solution to induce a flow, and then setting voltage at about 2.5 kV and taking a picture to see the response.

Figure 34:
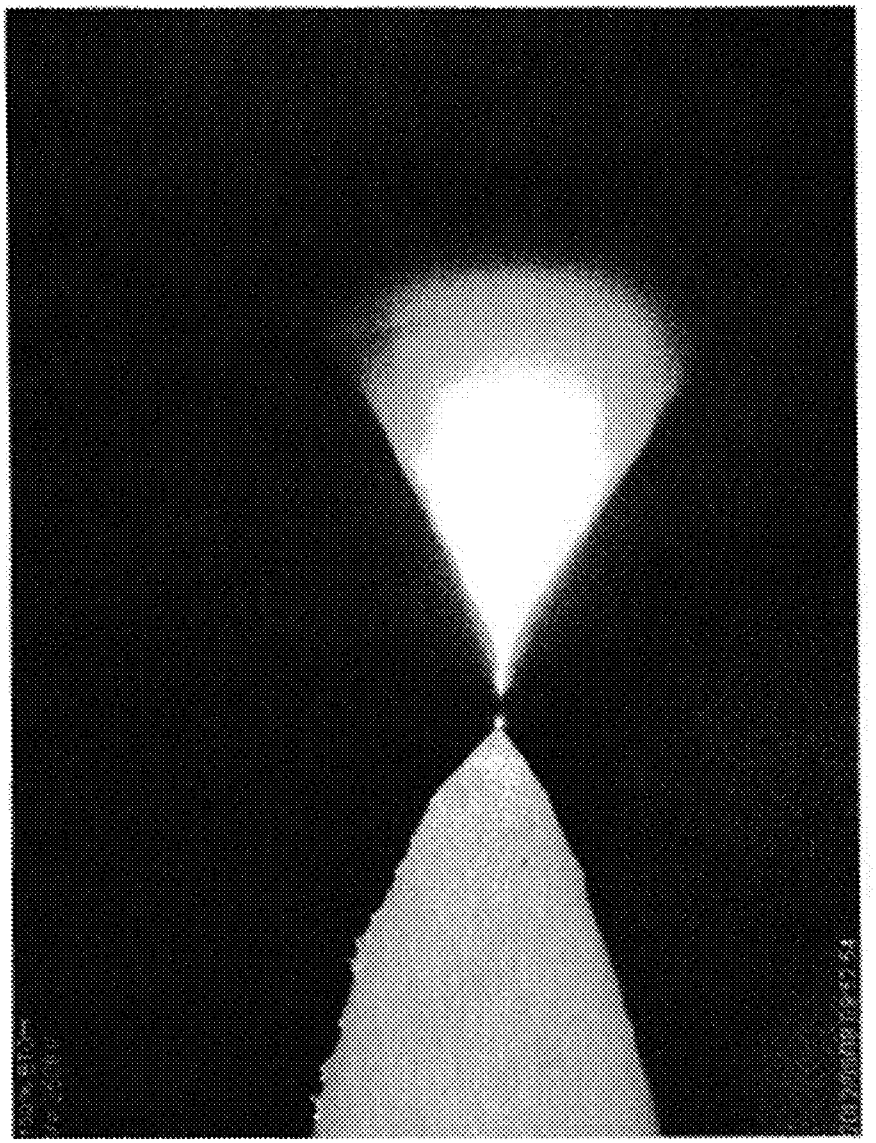
FIG. 34 illustrates electrospray formation with 100% ethanol using an example porous tip (standard fine brush).
Figure 35:
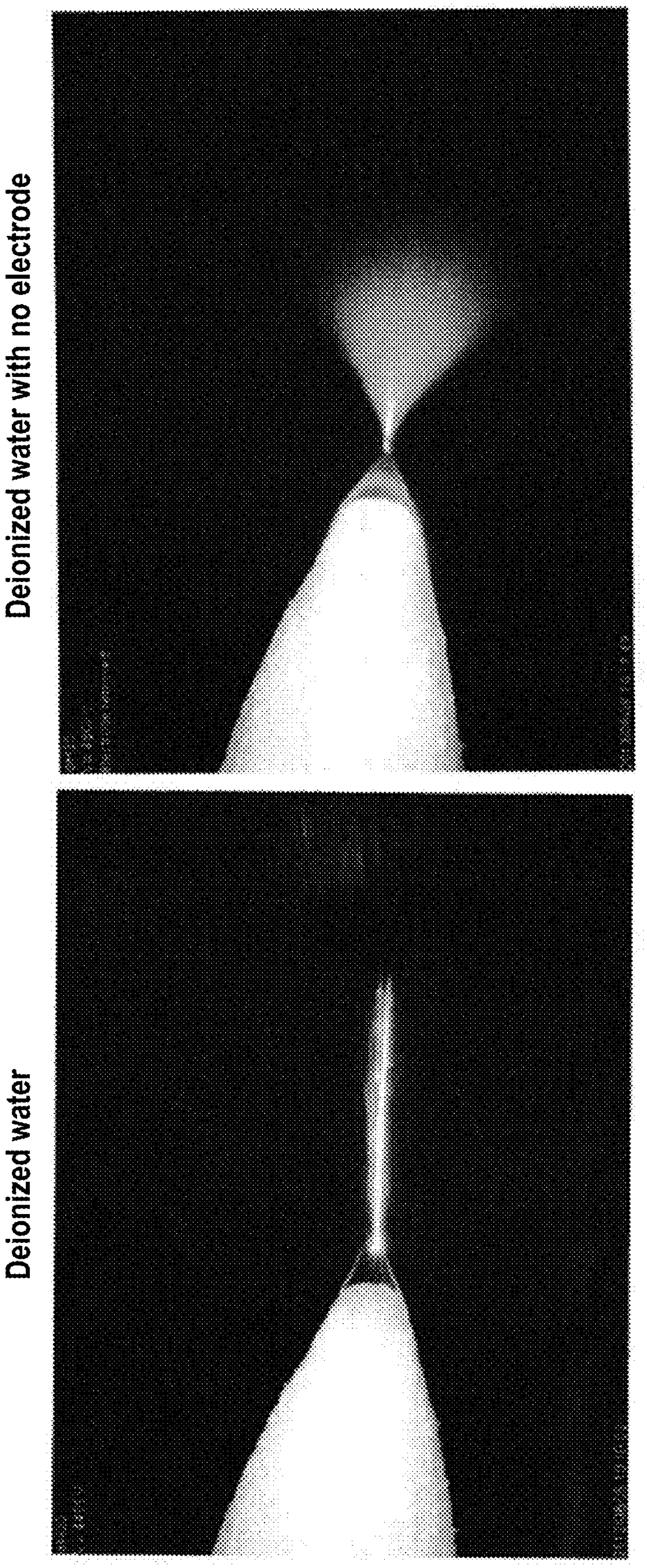
FIG. 35 illustrates electrospray formation using an example porous tip with deionized water at 4.4 kV, comparing when the electrode plate is present and not present. When the electrode plate is present, there is a jet ligament without a plume.
Figure 36:
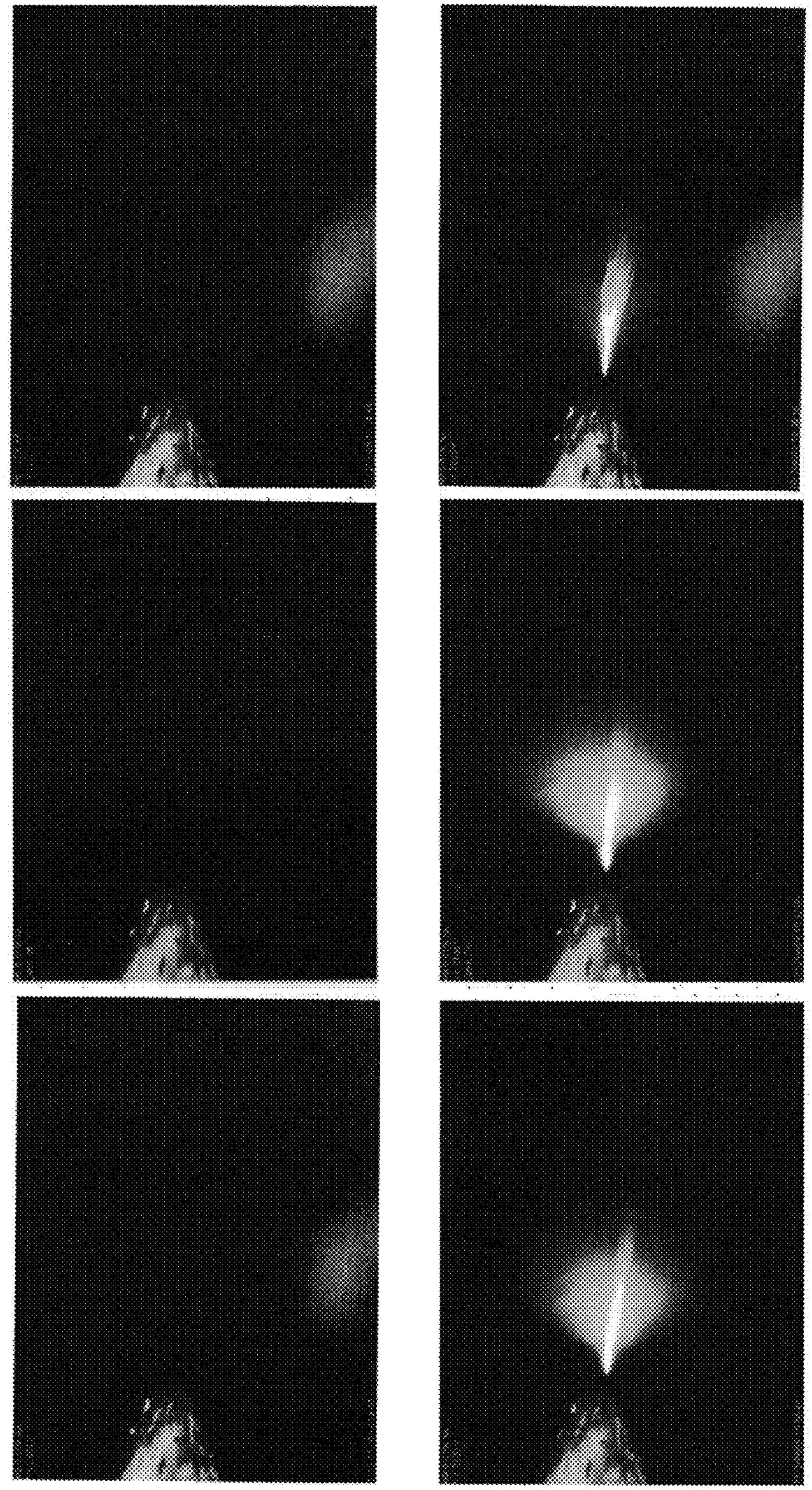
Figure 37:
FIG. 37 illustrates electrospray formation using an example porous tip with 0.25% methylene blue and 1% ethanol.

In this experiment, four different solutions were tested: a) 100% ethanol, b) deionized water, c) 0.25% methylene blue+0.01% ammonium acetate, and d) 0.25% methylene blue+1% ethanol. The test was made at a constant tip-to-plate distance of 11 mm. Summarizing the results, ethanol sprayed well as expected. The deionized water showed a jet ligament at 4.4 kV without a plume. However, when the counter electrode was removed and the solution sprayed into free space, an evidence of plume formation was observed for deionized water. The ethanol and deionized water tests are illustrated in FIGS. 34 and 35, respectively. The 0.25% methylene blue and 0.01% ammonium acetate solution demonstrated spray formation over a voltage range of 2.8 kV-3.1 kV. The observed spray pattern was a plume with a ligament at the center. Below 2.8 kV, there was not enough energy to draw the solution and no spray was observed. Above 3.1 kV, the spray appeared to pulsate or become sporadic with no sign of a stable plume. Within the spray voltage range, the spray can be controlled on and off by the foot switch as illustrated in FIG. 36. When the foot switch was latched off, the spray instantly stopped. When latched on, there was a delay as the system ramped up to the set voltage. Further, the spray range was sensitively affected by the position of the counter electrode, e.g., moving the position of the plate can require a small adjustment of the voltage to achieve a stable spray. Moreover, unlike deionized water, no spray was observed with no counter electrode for methylene blue. The 0.25% methylene blue and 1% ethanol solution was more difficult to spray. It showed signs of a plume, but unstable and pulsating at times as illustrated in FIG. 37. In addition, the 0.25% methylene blue and 0.01% ammonium acetate solution was tested with a super fine brush nib, but the configuration did not demonstrate a stable spray.

Figure 40:
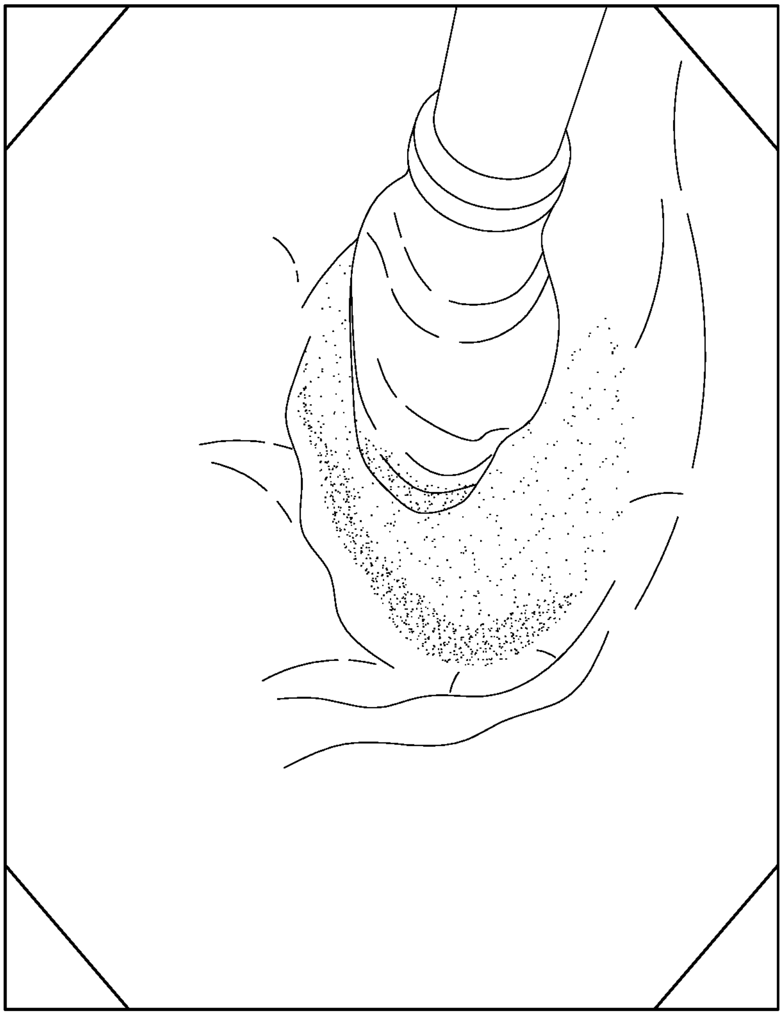
FIG. 40 illustrates the example electrospray catheter with parafilm that covers the metal shroud of the porous tip, tested to ex vivo ventilated porcine lungs.

In another experiment, the catheter coupled to a porous tip emitter head was tested with methylene blue and demonstrated a stable electrospray at 7.5 kV with the counter electrode present. The methylene blue delivery test was conducted within a bronchoscope onto the bench, and the spray delivery was achieved in dry and wet conditions for tip-to-plate distances from 9 to 16 mm. FIG. 38 illustrates an exemplary benchtop test setup of the catheter coupled to a porous tip emitter head. In addition, the methylene blue delivery test was conducted to ex vivo ventilated porcine lungs. FIGS. 39 and 40 show the ex vivo testing of the catheter with a porous tip to ventilated porcine lungs. To achieve stable spraying, the metal shroud was covered with parafilm as illustrated in FIG. 40. A tip-to-scope distance of 12 mm was used for this experiment. From this experiment, 100% (4 out of 4) effectiveness in trachea was observed.

In yet another experiment, the methylene blue delivery test was conducted to ex vivo ventilated porcine lungs with the tip-to-scope distance varying from 3 to 13 mm. 79% (29 out of 37) effectiveness in trachea was achieved, and comparable effectiveness was achieved in all tip-to-scope distances. It was observed that the spray consistently propelled in the forward direction with no wall attraction. A good electrical isolation was observed as well, and no current exceeding 100 μA was produced.

In the descriptions above and in the claims, phrases such as “at least one of” or “one or more of” may occur followed by a conjunctive list of elements or features. The term “and/or” may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases “at least one of A and B;” “one or more of A and B;” and “A and/or B” are each intended to mean “A alone, B alone, or A and B together.” A similar interpretation is also intended for lists including three or more items. For example, the phrases “at least one of A, B, and C;” “one or more of A, B, and C;” and “A, B, and/or C” are each intended to mean “A alone, B alone, C alone, A and B together, A and C together, B and C together, or A and B and C together.” In addition, use of the term “based on,” above and in the claims is intended to mean, “based at least in part on,” such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. An apparatus comprising:

a catheter defining a fluidic channel and having a distal opening, wherein the fluidic channel is configured to receive a metered volume of fluid, and wherein the fluid contains ethanol at greater than 5% concentration;

an electrode within the fluidic channel and spaced a distance from the distal opening of the catheter;

a porous tip disposed within the fluidic channel and disposed near the distal opening of the catheter, the porous tip comprising a material that is absorbent and fibrous, and wherein the porous tip is arranged in a cone shape geometry;

a protrusion disposed near the distal opening of the catheter and surrounding an outer surface of the catheter;

a thermoplastic wrap that encloses the protrusion to provide sealing and electrical isolation, such that the apparatus produces no current exceeding 100 μA; and a pump coupled to the catheter, wherein the pump is configured to provide the metered volume of fluid to the fluidic channel, wherein the metered volume of fluid is between 1 and 10 microliters of fluid per actuation of the pump, wherein the catheter is arranged to prevent direct contact between any electrode of the apparatus and tissue.

2. The apparatus of claim 1, further including a conductive sheath on an exterior of the catheter configured to couple to a ground, the catheter separating the fluidic channel and the conductive sheath.

3. The apparatus of claim 2, further including a biocompatible cover enclosing the conductive sheath between the biocompatible cover and the catheter.

4. The apparatus of claim 3, wherein the biocompatible cover extends less than an entire length of the catheter, and a distal end of the catheter is exposed.

5. The apparatus of claim 4, wherein the catheter has an inner diameter of about 0.5 mm and an outer diameter of about 1.4 mm; the distance between the electrode and the distal opening is about 100 mm; the biocompatible cover has an exterior diameter of about 2.05 mm, and the catheter extends about 50 mm beyond the biocompatible cover at the distal end.

6. The apparatus of claim 1, further including a wire extending through a portion of a length of the catheter and within the fluidic channel, the wire including an insulation layer and an exposed distal portion, the exposed distal portion forming the electrode.

7. The apparatus of claim 1, wherein the electrode, when carrying a charge, imparts the charge to fluid traveling through the fluidic channel, the charge imparted within the fluidic channel so that, when charged fluid reaches a fluid/air interface near the distal opening of the catheter, the charged fluid forms charged droplets that disperse.

8. The apparatus of claim 1, wherein the porous tip includes a felt material.

* * * * *